(12) United States Patent
Willey et al.

(10) Patent No.: US 8,304,192 B2
(45) Date of Patent: Nov. 6, 2012

(54) METHODS AND COMPOSITIONS FOR ASSESSING NUCLEIC ACIDS AND ALLELES

(75) Inventors: James C. Willey, Toledo, OH (US); Erin L. Crawford, Rossford, OH (US); David A. Weaver, Perrysburg, OH (US)

(73) Assignee: University of Toledo, Toledo, OH (US)

( * ) Notice: Subject to any disclaimer, the term of this patent is extended or adjusted under 35 U.S.C. 154(b) by 988 days.

(21) Appl. No.: 11/072,700

(22) Filed: Mar. 4, 2005

(65) Prior Publication Data
US 2006/0194216 A1    Aug. 31, 2006

Related U.S. Application Data

(60) Provisional application No. 60/550,279, filed on Mar. 5, 2004.

(51) Int. Cl.
*C12Q 1/68* (2006.01)

(52) U.S. Cl. ................................ 435/6.12; 435/6.11

(58) Field of Classification Search .............. None
See application file for complete search history.

(56) References Cited

U.S. PATENT DOCUMENTS

| | | | |
|---|---|---|---|
| 5,496,699 A | 3/1996 | Sorenson | |
| 5,712,125 A | 1/1998 | Uhlen | |
| 5,747,251 A | 5/1998 | Carson et al. | |
| 5,888,740 A | 3/1999 | Han | |
| 6,027,889 A | 2/2000 | Barany et al. | |
| 6,060,288 A * | 5/2000 | Adams et al. | 435/91.2 |
| 6,174,670 B1 | 1/2001 | Wittwer et al. | |
| 6,194,147 B1 * | 2/2001 | Baxter-Lowe et al. | 435/6 |
| 6,197,520 B1 | 3/2001 | Wittwer et al. | |
| 6,235,504 B1 | 5/2001 | Zhang et al. | |
| 6,245,514 B1 | 6/2001 | Wittwer | |
| 6,268,148 B1 | 7/2001 | Barany et al. | |
| 6,312,913 B1 * | 11/2001 | Wang et al. | 435/6 |
| 6,355,431 B1 | 3/2002 | Chee et al. | |
| 6,534,269 B2 | 3/2003 | Liu et al. | |
| 2002/0132244 A1 | 9/2002 | Li-Sucholeiki | |
| 2003/0077611 A1 | 4/2003 | Slepnev | |
| 2003/0082616 A1 | 5/2003 | Tomita et al. | |
| 2003/0092051 A1 | 5/2003 | Liu et al. | |
| 2003/0143584 A1 | 7/2003 | Li-Sucholeiki | |
| 2003/0148335 A1 | 8/2003 | Shen et al. | |

(Continued)

FOREIGN PATENT DOCUMENTS

EP    1092782    4/2001

(Continued)

OTHER PUBLICATIONS

PNAS—Table of Contents—Mar. 18, 2003, 100(6) [online] retrieved on Jul. 7, 2008 from: http://www.pnas.org/content/100/6 (20 pages).*

(Continued)

*Primary Examiner* — Samuel Woolwine
(74) *Attorney, Agent, or Firm* — MacMillan, Sobanski & Todd, LLC

(57) ABSTRACT

The present invention is directed to methods and compositions for evaluating allelic variations with improved quality controls, methods of preparing such compositions, and applications employing such compositions and methods. In particular, the present invention provides methods and compositions for reducing false positives and/or false negatives in nucleic acid measurements.

39 Claims, 31 Drawing Sheets

U.S. PATENT DOCUMENTS

| | | | |
|---|---|---|---|
| 2003/0186246 A1 | 10/2003 | Willey et al. | |
| 2003/0207295 A1 | 11/2003 | Gunderson et al. | |
| 2003/0211489 A1 | 11/2003 | Shen et al. | |
| 2003/0215821 A1 | 11/2003 | Gunderson et al. | |
| 2004/0018491 A1 | 1/2004 | Gunderson et al. | |
| 2004/0081993 A1 | 4/2004 | Cantor et al. | |
| 2004/0157238 A1* | 8/2004 | Quinn et al. | 435/6 |
| 2005/0165558 A1* | 7/2005 | Becker et al. | 702/20 |
| 2005/0239116 A1 | 10/2005 | Willey et al. | |

FOREIGN PATENT DOCUMENTS

| | | |
|---|---|---|
| EP | 1179600 | 2/2002 |
| EP | 1270738 A1 | 1/2003 |
| WO | WO 93/15229 A2 | 8/1993 |
| WO | WO 94/09156 | 4/1994 |
| WO | WO 94/23023 | 10/1994 |
| WO | WO 93/15229 A3 | 3/1995 |
| WO | WO 97/46707 | 12/1997 |
| WO | WO 98/58083 | 12/1998 |
| WO | WO 99/14376 | 3/1999 |
| WO | WO 99/51773 | 10/1999 |
| WO | WO 99/63109 A1 | 12/1999 |
| WO | WO 00/40755 | 7/2000 |
| WO | WO 00/63437 | 10/2000 |
| WO | WO 01/14539 | 3/2001 |
| WO | WO 01/16352 | 3/2001 |
| WO | WO 01/55454 | 8/2001 |
| WO | WO 01/62975 | 8/2001 |
| WO | WO 01/84146 A2 | 11/2001 |
| WO | WO 01/84146 A3 | 4/2002 |
| WO | WO 03/006677 | 1/2003 |
| WO | WO 03/035841 | 5/2003 |
| WO | WO 2004/001062 | 12/2003 |
| WO | WO 2004/007755 | 1/2004 |

OTHER PUBLICATIONS

Buetow et al. High-throughput development and characterization of a genomewide collection of gene-based single nucleotide polymorphism markers by chip-based matrix-assisted laser desorption/ionization time-of-flight mass spectrometry. PNAS 98(2):581-584, Jan. 16, 2001.*

Allen, et al. Enhanced insulin-like growth factor binding protein-related protein 2 (Connective tissue growth factor) expression in patients with idiopathic pulmonary fibrosis and pulmonary sarcoidosis. Am J Respir Cell Mol Biol. 1999; 21(6): 693-700.

Amabile, et al. Real-time quantification of different types of bcr-abl transcript in chronic myeloid leukemia. Haematologica. 2001; 86(3): 252-9.

Apostolakos, et al. Measurement of gene expression by multiplex competitive polymerase chain reaction. Anal Biochem. 1993; 213(2): 277-84.

Cell et al. A rapid and versatile method to synthesize internal standards for competitive PCR. Nucleic Acids Res. 1993; 21(4): 1047.

Crawford, et al. Multiplex standardized RT-PCR for expression analysis of many genes in small samples. Biochem Biophys Res Commun. 2002; 293(1): 509-16.

Crawford, et al. Normal bronchial epithelial cell expression of glutathione transferase P1, glutathione transferase M3, and glutathione peroxidase is low in subjects with bronchogenic carcinoma. Cancer Res. 2000; 60(6): 1609-18.

Crawford, et al. Quantitative end-point RT-PCR expression measurement using the Agilent 2100 Bioanalyzer and standardized RT-PCR. Agilent Application. 2001; 1-8.

Crawford, et al. Reproducible gene expression measurement among multiple laboratories obtained in a blinded study using standardized RT (StaRT)-PCR. Mol Diagn. 2001; 6(4): 217-25.

Demuth, et al. The gene expression index c-myc x E2F-1/p21 is highly predictive of malignant phenotype in human bronchial epithelial cells. Am J Respir Cell Mol Biol. 1998; 19(1): 18-24.

Devereux, et al. A comprehensive set of sequence analysis programs for the VAX. Nucleic Acids Res. 1984; 12(1 Pt 1): 387-95.

Ding, et al. A high-throughput gene expression analysis technique using competitive PCR and matrix-assisted laser desorption ionization time-of-flight MS. Proc Natl Acad Sci USA. 2003; 100(6): 3059-64.

Giulietti, et al. An overview of real-time quantitative PCR: applications to quantify cytokine gene expression. Methods. 2001; 25(4): 386-401.

Hedenfalk, et al. Gene-expression profiles in hereditary breast cancer. N Engl J Med. 2001; 344(8): 539-48.

Lee, et al. Seven-color, homogeneous detection of six PCR products. Biotechniques. 1999; 27(2): 342-9.

Loitsch, et al. Reverse transcription-competitive multiplex PCR improves quantification of mRNA in clinical samples—application to the low abundance CFTR mRNA. Clin Chem. 1999; 45(5): 619-24.

Meijerink, et al. A novel method to compensate for different amplication efficiencies between patient DNA samples in quantitative real-time PCR. J Mol Diagn. 2001; 3(2): 55-61.

Meksem, et al. A high-resolution map of the vicinity of the R1 locus on chromosome V of potato based on RFLP and AFLP markers. Mol Gen Genet. 1995; 249(1): 74-81.

Mollerup, et al. Sex differences in lung CYP1A1 expression and DNA adduct levels among lung cancer patients. Cancer Res. 1999; 59(14): 3317-20.

Ross, et al. Quantitative approach to single-nucleotide polymorphism analysis using MALDI-TOF mass spectrometry. Biotechniques. 2000; 29(3): 620-4, 626, 628-9.

Rots, et al. Circumvention of methotrexate resistance in childhood leukemia subtypes by rationally designed antifolates. Blood. 1999; 94(9): 3121-8.

Rots, et al. mRNA expression levels of methotrexate resistance-related proteins in childhood leukemia as determined by standardized competitive template-based RT-PCR method. Leukemia. 2000; 14(12): 2166-75.

Siebert, et al. PCR MIMICS: competitive DNA fragments for use as internal standards in quantitative PCR. Biotechniques. 1993; 14(2): 244-9.

Vondracek, et al. Transcript profiling of enzymes involved in detoxification of xenbiotics and reactive oxygen in human normal and simian virus 40 T antigen-immortalized oral keratinocytes. Int J Cancer. 2002; 99(6): 776-82.

Willey, et al. Expression measurement of many genes simultaneously by quantitative RT-PCR using standardized mixtures of competitive templates. Am J Respir Cell Mol Biol. 1998; 19(1): 6-17.

Willey, et al. Quantitative RT-PCR measurement of cytochromes p450 1A1, 1B1, and 2B7, microsomal epoxide hydrolase, and NADPH oxidoreductase expression in lung cells of smokers and nonsmokers Am J Respir Cell Mol Biol. 1997; 17(1): 114-24.

Adler, et al. A real-time immuno-PCR assay for routine ultrasensitive quantification of proteins. Biochem Biophys Res Commun. Aug. 22, 2003;308(2):240-50.

Supplementary European Search Report dated May 14, 2008 for EP 05777370.7.

Alexandre, et al. Quantitative determination of CMV DNA using a combination of competitive PCR amplification and sandwich hybridization. Biotechniques. Oct. 1998;25(4):676-83.

Hayashi, et al. A competitive nucleic acid sequence-based amplification assay for the quantification of human MDR1 transcript in leukemia cells. Clin Chim Acta. Apr. 2004;342(1-2):115-26.

* cited by examiner

Positions A & B: Oligo specific to Reference gene NT and CT
Positions 1 - 7: Oligo specific to Target gene NT and CT Standardized Mixtures

| A Mix |
| ACTB 600,000 Molecules/uL |
| *Targets 6,000,000 Molecules/uL* |

| B Mix |
| ACTB 600,000 Molecules/uL |
| *Targets 600,000 Molecules/uL* |

| C Mix |
| ACTB 600,000 Molecules/uL |
| *Targets 60,000 Molecules/uL* |

| D Mix |
| ACTB 600,000 Molecules/uL |
| *Targets 6,000 Molecules/uL* |

| E Mix |
| ACTB 600,000 Molecules/uL |
| *Targets 600 Molecules/uL* |

| F Mix |
| ACTB 600,000 Molecules/uL |
| *Targets 60 Molecules/uL* |

Figure 14

METHODS AND COMPOSITIONS FOR ASSESSING NUCLEIC ACIDS AND ALLELES

CROSS REFERENCE TO RELATED APPLICATIONS

This application claims the benefit of U.S. Provisional Patent Application No. 60/550,279, filed Mar. 5, 2004.

GOVERNMENT INTERESTS

Certain embodiments of the present invention were made under Research Grant No. CA 85147 and CA 95806 from the National Cancer Institute, who may have certain rights thereto.

BACKGROUND OF THE INVENTION

With the sequencing of the human genome comes the hope of accelerating drug development and discovering better diagnostic tests. This hope has engendered a need to develop improved methods for multi-gene expression measurement, as well as for assessing differential expression between alleles. Methods amenable to appropriate quality control, for example, to meet regulatory guidelines, are particularly needed. The present invention relates to compositions and methods directed to addressing these hopes and needs.

Other methods and compositions directed thereto are provided in U.S. patent application Ser. No. 10/109,349, filed Mar. 28, 2002, and Ser. No. 10/471,473; International Applications PCT/US03/09428, filed Mar. 27, 2003; and U.S. Provisional Application Ser. Nos. 60/368,288 and 60/368,409, filed Mar. 28, 2002; 60/561,841, filed Apr. 12, 2004; and 60/646,157, filed Jan. 21, 2005, each of which are herein incorporated by reference, as is U.S. Provisional Application Ser. No. 60/550,279, filed Mar. 5, 2004.

BRIEF DESCRIPTION OF THE FIGURES

The novel features of the invention are set forth with particularity in the appended claims. A better understanding of the objects, features and advantages of the present invention will be obtained by reference to the following detailed description that sets forth illustrative embodiments, in which the principles of the invention are utilized, and the accompanying drawings of which:

FIG. 14 illustrate a series of serially-diluted standardized mixtures A-F comprising a series of concentrations of competitive templates for target nucleic acids (6,000,000; 600,000; 60,000; 6,000; 600 and 60 molecules/µL, respectively) relative to a given concentration of competitive template for a β-actin (600,000 molecules/µL).

Figure 1:
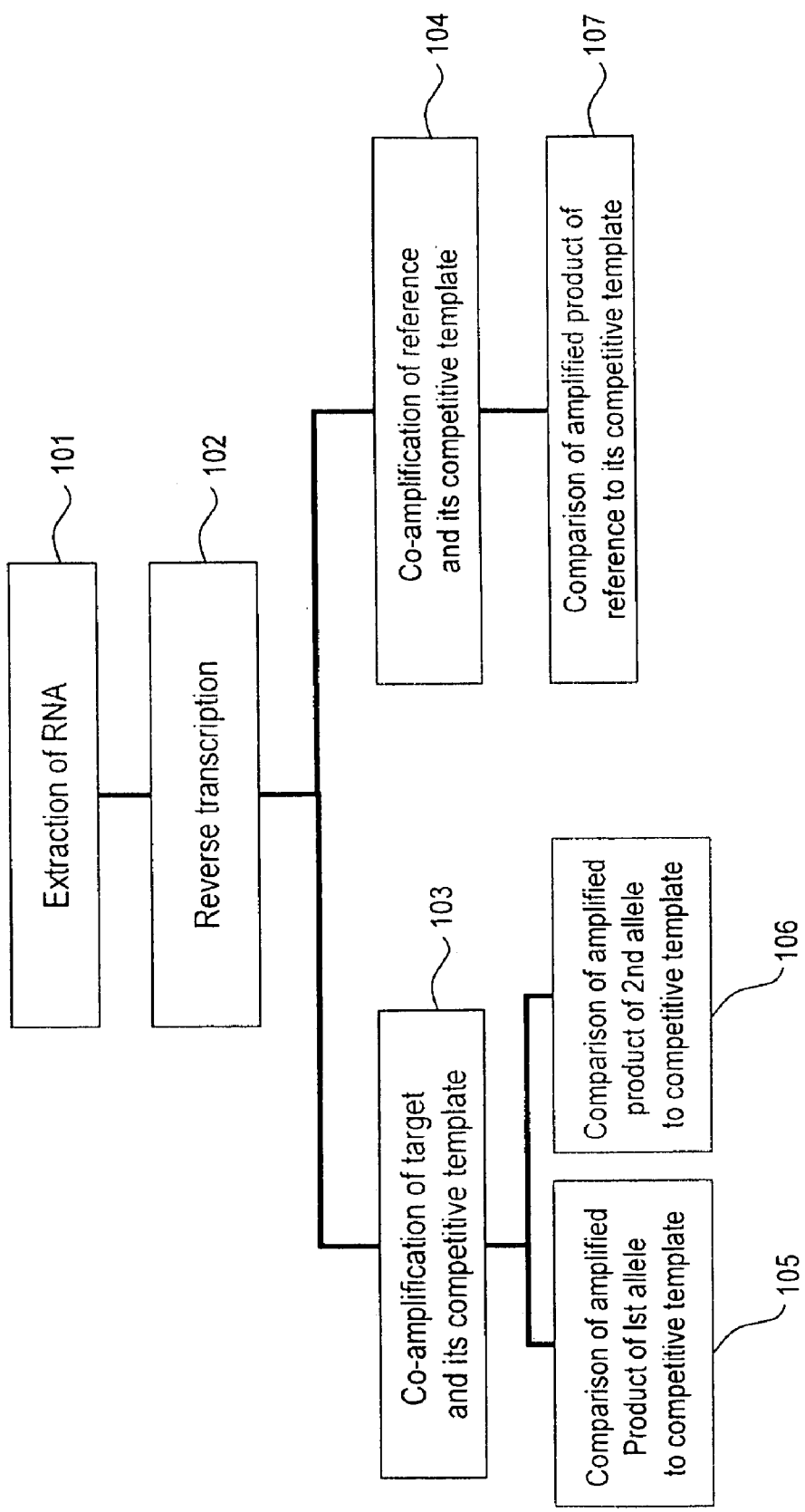
FIG. 1 illustrates an overall process for assessing allele frequency in accordance with some embodiments of the instant invention.

Each of these figures provides an illustration only, and is in no way intended to be limiting with respect to the present invention. For example, those skilled in the art will readily appreciate variations and modifications of the schemes illustrated based on the teachings provided herein.

DETAILED DESCRIPTION OF THE INVENTION

The present invention is directed to methods and compositions for evaluating allelic nucleic acids, methods of preparing such compositions, and applications employing such compositions and methods. Some aspects of the present invention relate to improvements upon the Willey and Willey et al. U.S. Pat. Nos. 5,639,606; and 5,876,978.

I. Methods for Assessing Nucleic Acids

One aspect of the present invention relates to methods for assessing amounts of a nucleic acid in a sample. In some embodiments, the invention allows measurement of small amounts of a nucleic acid, for example, where the nucleic acid is expressed in low amounts in a specimen, where small amounts of the nucleic acid remain intact and/or where small amounts of a specimen are provided. In particular, the method allows for assessing relative representation of allelic variations of nucleic acids, including rare alleles that are present in low amounts. For example, in some embodiments, practice of the invention assesses allelic frequency in small samples of biological specimens.

"Specimen" as used herein can refer to material collected for analysis, e.g., a swab of culture, a pinch of tissue, a biopsy extraction, a vial of a bodily fluid e.g., saliva, blood and/or urine, etc. that is taken for research, diagnostic or other purposes from any biological entity. "Biological entity" as used herein can refer to any entity capable of harboring a nucleic acid, including any species, e.g., a virus or other pathogen, a cell, a tissue, an in vitro culture, a plant, an animal, and/or a subject participating in a clinical trial. "Sample" as used herein can refer to specimen material used for a given assay, reaction, run, trial, and/or experiment. For example, a sample may comprise an aliquot of the specimen material collected, up to and including all of the specimen. As used herein the terms assay, reaction, run, trial and/or experiment can be used interchangeably. Some embodiments of the present invention can be practiced using small starting amount of nucleic acid to yield quantifiable amounts.

In some embodiments, the specimen collected may comprise less than about 100,000 cells, less than about 10,000 cells, less than about 5,000 cells, less than about 1,000 cells, less than about 500 cells, less than about 100 cells, less than about 50 cells, or less than about 10 cells. In some embodiments, methods of the present invention are capable of assessing the amount of a nucleic acid present in a sample comprising less than about 100,000 cells. For example, a sample from a biopsy may comprise less than about 100,000 cells. In some embodiments, the method is capable of assessing the amount of a nucleic acid in less than about 10,000 cells, less than about 5,000 cells, less than about 1,000 cells, less than about 500 cells, less than about 100 cells, less than about 50 cells, or less than about 10 cells. Small biological specimen can also refer to amounts typically collected in biopsies, e.g., endoscopic biopsies (using brush and/or forceps), needle aspirate biopsies (including fine needle aspirate biopsies), as well as amounts provided in sorted cell populations (e.g., flow-sorted cell populations) and/or micro-dissected materials (e.g., laser captured micro-dissected tissues). For example, biopsies of suspected cancerous lesions in the lung, breast, prostate, thyroid, and pancreas, commonly are done by fine needle aspirate (FNA) biopsy, bone marrow is also obtained by biopsy, and tissues of the brain, developing embryo, and animal models may be obtained by laser captured micro-dissected samples.

In some embodiments, assessing, evaluating and/or measuring a nucleic acid can refer to providing a measure of the amount of a nucleic acid in a specimen and/or sample, e.g., to determine the level of expression of a gene. In some embodiments, providing a measure of an amount refers to detecting a presence or absence of the nucleic acid of interest. In some embodiments, providing a measure of an amount can refer to quantifying an amount of a nucleic acid can, providing a measure of concentration or degree of the amount of the nucleic acid present. In some embodiments, providing a measure of the amount of a nucleic acid refers to enumerating the amount of the nucleic acid, e.g., indicating a number of molecules of the nucleic acid present in a sample. The nucleic acid of interest may be referred to as a target nucleic acid, and a gene of interest, e.g., a gene being evaluated, may be referred to as a target gene. As used herein, the term "gene" can refer to nucleic acid molecules comprising an open reading frame. In some embodiments, relative amounts of one or more alleles of a nucleic acid can be assessed.

In some embodiments, methods of the present invention are capable of enumerating less than about 1,000 molecules of a nucleic acid in a sample, e.g., about 800, about 600, or about 400 molecules of the nucleic acid. In some embodiments, less than about 100 molecules, e.g., about 60 molecules, preferably less than about 10 molecules, e.g., about 6 molecules, or more preferably less than about 1 molecule of a nucleic acid can be enumerated in a sample. For example, in preferred embodiments, a single molecule of nucleic acid template can give rise to detectable amplified product. In some embodiments, methods of the instant invention can measure less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of a nucleic acid in a sample. The number of molecules of a nucleic acid can also be referred to as the number of copies of the nucleic acid found in a sample and/or specimen.

The practice of some embodiments of the present invention permits rare transcripts to be measured with statistical significance. For example, in some embodiments, the number of copies of a nucleic acid corresponding to a gene transcript can be determined, e.g., the number of copies/cell, where the gene is expressed in low copy number. In some embodiments, the number of copies of a nucleic acid corresponding to an expressed allele can be determined where the allele is rarely expressed.

Enumerating less than about 10,000, less than about 1,000 or less than about 100 molecules can allow measurement of less than about 10 copies/cell of at least about 100 different gene transcripts in a small biological specimen, e.g., from the amount of material typically used to obtain one gene measurement, e.g., to measure that few copies of a nucleic acid corresponding to one gene or to one allele of a gene. In some embodiments, methods of the instant invention are capable of measuring and/or enumerating less than about 10 copies/cell of at least about 100 different gene transcripts in a small biological specimen, e.g., from the amount of material typically used to obtain one gene measurement.

In still some embodiments, more measurements can be obtained from a given specimen and/or sample, e.g., of the size typically used to measure that few copies of a nucleic acid corresponding to one gene or to one allele of a gene. For example, practice of some embodiments of the invention disclosed herein can measure and/or enumerate less than about 100, less than about 50, less than about 20, less than about 10, less than about 8, or less than about 5 copies/cell of at least about 20, at least about 50, at least about 80, at least about 100, at least about 120, at least about 150, or at least about 200 different nucleic acids in a sample, e.g., corresponding to different gene transcripts.

The expressed material may be endogenous to the biological entity, e.g., transcripts of a gene naturally expressed in a given cell type, or the expressed material to be measured may be of an exogenous nature. For example, in some embodiments, methods of the present invention can be used to quantify transfected genes following gene therapy and/or a reporter gene in transient transfection assays, e.g., to determine the efficiency of transfection (Morales, M. J., and Gottlieb, D. I., A polymerase chain reaction-based method for detection and quantification of reporter gene expression in transient transfection assays, Analytical Biochemistry, 210, 188-194 (1993)).

As used herein, "nucleic acid" can refer to a polymeric form of nucleotides and/or nucleotide-like molecules of any length. In preferred embodiments, the nucleic acid can serve as a template for synthesis of a complementary nucleic acid, e.g., by base-complementary incorporation of nucleotide units. For example, a nucleic acid can comprise naturally occurring DNA, e.g., genomic DNA, RNA, e.g., mRNA, and/or can comprise a synthetic molecule, including but not limited to cDNA and recombinant molecules generated in any manner. For example the nucleic acid can be generated from chemical synthesis, reverse transcription, DNA replication or a combination of these generating methods. The linkage between the subunits can be provided by phosphates, phosphonates, phosphoramidates, phosphorothioates, or the like, or by nonphosphate groups as are known in the art, such as peptide-type linkages utilized in peptide nucleic acids (PNAs). The linking groups can be chiral or achiral. The polynucleotides can have any three-dimensional structure, encompassing single-stranded, double-stranded, and triple helical molecules that can be, e.g., DNA, RNA, or hybrid DNA/RNA molecules. A nucleotide-like molecule can refer to a structural moiety that can act substantially like a nucleotide, for example exhibiting base complementarity with one or more of the bases that occur in DNA or RNA and/or being capable of base-complementary incorporation. The terms "polynucleotide," "polynucleotide molecule," "nucleic acid molecule," "polynucleotide sequence" and "nucleic acid sequence," can be used interchangeably with "nucleic acid" herein

A. Assessing Allele Frequency

In some embodiments, the present invention provides a method of assessing allele frequency of a first allele and a second allele of a target nucleic acid in a sample. As used herein, alleles, e.g., first and second alleles, is used interchangeably with allelic variation and can refer to any variation between homologous regions of nucleic acid sequences, including for example, between maternally- and paternally-derived genes. For example, an allele may be one of a group of genes which occur alternatively at a given genetic locus. The variation may be due to, e.g., to spontaneous mutation, inherited mutation, viral infection, gene therapy or other genetic phenomena resulting in such variation.

For example, diploid cells can have one allele derived from one parent and another derived from another parent. Various differences can occur in nucleic acid sequences between such alleles, as well as between individuals and between populations. Allele frequencies that can be assessed by the instant invention include non-pathological differences, generally referred to as DNA polymorphisms or nucleotide sequence polymorphisms, as well as mutations resulting in and/or associated with abnormal or non-desirable conditions, such as a disease phenotype. For example, allelic variations that occur in exon regions of genes can be expressed in mRNA and may correlate with a particular biological state. In addition, variations that affect RNA expression levels may exist in regulatory or control sequences, and may be detected by assessing amounts of the nucleic acid(s) under their control.

In some preferred embodiments, practice of the present invention assesses allele frequency of single nucleotide polymorphisms (SNPs). SNPs can refer to nucleotide sequence polymorphisms that arise from the substitution of a single nucleotide pair, e.g., resulting in a single base change in expressed RNA. The substitution can include a missense mutation, e.g., resulting in substitution of one amino acid for another in the corresponding protein; or a nonsense mutation, e.g., where the altered sequence creates as stop codon, resulting in a shortened protein that may function improperly or not at all. SNPs occur on average in more than one in about every thousand base pairs in human DNA, and can serve as markers for regions of a genome, e.g., covering an entire human genome.

In some other embodiments, the practice of the instant invention assesses breakpoint mutations. Breakpoint mutations can result from chromosomal translocations and/or other rearrangement. In some cases, the translocation can result in deregulation of expression of a gene located at the breakpoint of the chromosome. Some embodiments of the instant invention do not detect aneuploidy.

Other types of alleles can also be assessed. Examples include microsatellite polymorphisms, e.g., due to differences in the number of repetitions of short repeat sequences of about 2 to about 4 base pairs; VNTR (Variable Number of Tandem Repeat) polymorphisms, e.g., that can differ in terms of number of repeats and/or the number of nucleotide sequences in units of several tens of base pairs; insertions, e.g., which add to a sequence and can result in the corresponding protein not functioning properly; and/or deletions, e.g., which remove part of a sequence. Small deletions may remove one or a few base pairs within a gene, e.g., altering the function of the corresponding protein, while larger deletions can remove an entire gene or several neighboring genes. Other types of alleles that may be assessed include duplications, e.g., where a nucleic acid sequence is abnormally copied one or more times; frame-shift mutations, e.g., where the addition and/or loss of bases changes a gene's reading frame; and/or repeat expansions, e.g., where short nucleic acid sequences are repeated an increased number of times in a row.

FIG. 1 schematically illustrates some embodiments of the overall process for assessing allele frequency, including the frequency of any of the alleles provided above. "Allele frequency" as used herein can refer to the relative representation of one allele compared to one or more other alleles in a biological entity or population of biological entities. For example, the allele frequency may be assessed in a sample comprising nucleic acid from one subject or in a sample comprising pooled nucleic acid from different subjects. Allele frequency can refer to the occurrence of one allele compared to another in DNA, e.g. genomic and/or mitochondrial DNA. Allele frequency can also refer to the occurrence of one allele compared to another in RNA, e.g., expressed mRNA, tRNA, rRNA, snRNA, and the like. In some embodiments, the specimen collected comprises RNA to be measured, e.g., mRNA expressed in a tissue culture. In some embodiments the specimen collected comprises DNA to be measured, e.g., cDNA reverse transcribed from transcripts. In some embodiments, the nucleic acid to be measured is provided in a heterogeneous mixture of other nucleic acid molecules.

FIG. 1 illustrates an embodiment using RNA. Step 101 of FIG. 1 illustrates extracting RNA from specimen cells or tissues. When an allelic variation occurs in an exon of a gene, for example, mRNA expressed from the two alleles can be used to assess allelic frequency. Messenger RNA may be transcribed from the two alleles in equal amounts, so that the allele frequency assessed using RNA reflects or substantially reflects the allele frequency present in genomic DNA. The invention also contemplates the situation where mRNA is differentially transcribed form the two alleles, so that the allele frequency assessed using RNA is different for that present in DNA. For example, upstream nucleotide sequence polymorphisms or mutations may affect regulatory sequences controlling gene expression; and/or mRNA species may have different stabilities, e.g., due to differences in the 3' terminal sequence of the mRNA.

Step 102 of FIG. 1 illustrates reverse transcribing extracted RNA to provide cDNA. In other embodiments, the amplified nucleic acid is a nucleic acid other than cDNA, as described above, including genomic DNA.

Step 103 of FIG. 1 illustrates co-amplifying the target nucleic acid cDNA and a known amount of a competitive template for the target nucleic acid. For example, the cDNA may be serially diluted and one or more serial dilutions then amplified. The target nucleic acid cDNA preferably comprises sequence corresponding to a first allele and sequence corresponding to a second allele. Target nucleic acid sequences corresponding to further alleles, e.g., third, fourth, fifth alleles, etc., are also contemplated, where target nucleic acid corresponding to the various alleles can be co-amplified with a competitive template for the target nucleic acid.

Various nucleic acids and corresponding competitive templates may be amplified in a given vessel. For example, in some embodiments, more than one nucleic acid (each with its corresponding competitive template) are co-amplified in a given vessel. The vessel used may be any object capable of allowing a reaction mixture to exist therein and/or thereon. For example, the vessel may comprise a well, tube, nano and/or microfluidic reservoir and/or channel, capillary, groove, surface, and/or other container.

Step 104 of FIG. 1 illustrates co-amplifying a second nucleic acid and a known amount of a competitive template for the second nucleic acid, which can be carried out in the same or different vessel as used in step 103. In preferred embodiments, the second nucleic acid can serve as a reference for the target nucleic acid being amplified. "Reference nucleic acid" as used herein can refer to a nucleic acid that is amplified as well as the target nucleic acid. The target nucleic acid can be "normalized" to a reference nucleic acid. In some embodiments, the reference nucleic acid serves as a control for loading, e.g., to control for cDNA loaded into the reaction. For example, in some preferred embodiments, the reference nucleic acid comprises a nucleic acid that is not expected to vary (or to vary significantly) among given biological specimen and/or in response to certain stimuli. For example, mRNA from a constitutively expressed gene may provide the reference nucleic acid. In some embodiments, known or potential housekeeping genes may provide the reference nucleic acid, including but not limited to human, mouse and/or rat glyceraldehydes-3-phosphate dehydrogenase (GAPD or GAPDH), β-actin, 28S RNA, 18S RNA, and/or other ribonuclear protein genes. Other housekeeping genes that have been used as internal standards in Northern analyses of gene expression may also be used. See, e.g., Devereux et al., Nucleic Acids Res. 12:387 (1984); Barbu et al., Nucleic Acids Res. 17:7115 (1989).

Where genomic DNA is used, a reference nucleic acid can comprise a sequence corresponding to a gene whose representation in a genome is not expected to vary, e.g., β-actin has been shown to occur about 16 times per genome. In preferred embodiments, a gene known to be present in only two copies in the genome and that has no known pseudogenes may be used, e.g., a gene other than the β-actin gene. The number of copies assessed is important for determining the sensitivity and specificity of the test and ensuring quality control. In some embodiments, a sequence corresponding to a gene that appears only once in a genome can also be used, e.g. a single genomic DNA copy reference gene. In still some embodiments, one of the alleles of the target nucleic acid can be used as the reference nucleic acid, e.g., the more common or normal allele may be used as a reference for the other allele.

Many other genes can provide reference nucleic acids. The choice of reference nucleic acid may depend on the tissues to be assayed and/or the biological states being studied. For example, β-actin varies little among different normal bronchial epithelial cell samples (see, e.g., Crawford, E. L., Khuder, S. A., Durham, S. J., et al. (2000) Normal bronchial epithelial cell expression of glutathione transferase P1, glutathione transferase M3, and glutathione peroxidase is low in subjects with bronchogenic carcinoma. *Cancer Res.* 60, 1609-1618), but it may vary over about 100-fold in samples from different tissues, such as bronchial epithelial cells compared to lymphocytes.

In preferred embodiments, the competitive templates of the target and reference nucleic acids are at known concentrations relative to one another. "Competitive template" as used herein can refer to a nucleic acid that competes with a nucleic acid during an amplification reaction. That is, when present in a reaction mixture for amplifying a target nucleic acid, the competitive template competes to serve as the template for such amplification. In some embodiments, for example, the competitive template for a given nucleic acid has a structure allowing its amplification to the same or substantially the same extent as the given nucleic acid. For example, primers can be designed to amplify a target nucleic acid and its corresponding competitive template, as known in the art and/or provided herein. The term "primer" generally refers to a nucleic acid capable of acting as a point of initiation of synthesis along a complementary strand when conditions are suitable for synthesis of a primer extension product.

In preferred embodiments, a competitive template for a given nucleic acid can be amplified using one or more of the same primers as that of the given nucleic acid and/or amplifies with the same or substantially the same efficiency as the given nucleic acid. In preferred embodiments, a competitive template for a given nucleic acid is amplified using the same primers, shares sequence homology, and/or amplifies with the same or substantially similar efficiency as the given nucleic acid. In some embodiments, competitive templates are referred to as internal standards or as competitive template internal standards. For example, competitive template for the reference nucleic acid may comprise a nucleic acid having a sequence similar to either strand of cDNA of a housekeeping gene, but having a distinguishable feature as described below.

For assessing allelic variation, primers can be designed to span the site or sites of the target nucleic acid comprising allelic variations. In such embodiments, a given primer pair can amplify target nucleic acid corresponding to both alleles represented in a sample, as well as a competitive template for that target nucleic acid. In some embodiments, methods of the instant invention do not use allele-specific primers, e.g., primers that can amplify the first allele but not the second allele, or vice versa, of a given target nucleic acid. Rather, a given pair of primers can amplify target nucleic acid corresponding to either allele. Still, in some embodiments, the methods of the instant invention do not use a universal priming sequence. Rather, the given pair of primers used amplifies target nucleic acid corresponding to both alleles as well as the competitive template for the target nucleic acid, but does not amplify other nucleic acids, like the reference nucleic acid, in some embodiments.

The target and reference nucleic acids can be referred to as "native templates." The term "native template" as used herein can refer to nucleic acid obtained directly or indirectly from a specimen that can serve as a template for amplification. For example, it may refer to cDNA molecules, corresponding to a gene whose allelic frequency is to be measured, where the cDNA is amplified and quantified.

The competitive template can have a distinguishing feature from the native template, e.g., allowing its amplified product to be distinguished from the amplified product of the nucleic acid to be assessed. In preferred embodiments, the competitive template for the target nucleic acid can be distinguished from target nucleic acid corresponding to either the first and/or second allele. For example, in some embodiments, the competitive template can comprise mutants of the target nucleic acid that are different from the mutations providing the first and second alleles. Mutations can be point mutations, insertions, inversions, deletions or the like. For example, in some embodiments, a competitive template comprises at least one nucleotide that is different from the corresponding nucleotide in the first allele and different from the corresponding nucleotide in the second allele of the target nucleic acid. In some embodiments, the competitive template comprises at least about two, at least about three, at least about 5, at least about 10, at least about 15, or at least about 20 nucleotides that are different. Longer deletions, insertions, inversions, substitutions and/or other alterations are provided in some embodiments.

In preferred embodiments, a target nucleic acid sequence is artificially shortened to provide its corresponding competitive template. Some methods of producing artificially shortened competitive templates are known in the art, e.g., and may be generated according to the method described by Celi et al., Nucleic Acids Res. 21:1047 (1993). In more preferred embodiments, the shorted competitive template no longer includes the allelic region(s) of its corresponding target. For example, the competitive template may be shortened so as to be missing regions expected to have variations, e.g., a mutation or nucleotide sequence polymorphism. This can facilitate detection and/or quantification of the different species (competitive template, target nucleic acid corresponding to a first allele, and nucleic acid corresponding to a second allele) as will be detailed below.

In still some embodiments, the competitive template comprises an alteration that causes a loss and/or a gain of one or more cleavage sites in the competitive template compared to its corresponding nucleic acid. For example, a base may be substituted in a competitive template sequence to result in the gain and/or loss of a restriction endonuclease recognition site, chemical cleavage site, or other specific cleavage site. Various programs may be used to identify and match one or two or more base mismatch sequences for known recognition sites. For example, the Map program within Genetics Computer Group software package (Devereux et al., supra, 1984) may be used. In this program, cDNA sequences are obtained for a given nucleic acid, and then the sequence is evaluated for the presence of one or two base pair mismatches for known restriction endonucleases. In preferred embodiments, the gain and/or loss of restriction site occurs in a region other than at an allelic difference to be assessed.

In some embodiments, the competitive template comprises an alteration that causes a loss and/or a gain of one or more specific recognition sites in the competitive template compared to its corresponding nucleic acid. For example, a base may be substituted in a competitive template sequence to result in the gain and/or loss of a protein binding site such as a transcription factor binding site, preferably where the change occurs in a region other than at an allelic difference to be measured. Other structural changes for distinguishing amplified product of a competitive template from amplified product of its corresponding nucleic acid will be apparent to those of skill in the art and are also within the scope of the instant invention.

Amplification can be achieved by any methods known in the art and/or disclosed herein for amplifying nucleic acid molecules. When polymerase chain reaction (PCR) amplification is used, conditions can include the presence of ribonucleotide and/or deoxyribo-nucleotide di-, tri-, tetra-, penta- and/or higher order phosphates; primers for PCR amplification for at least one nucleic acid and its corresponding competitive template; and at least one polymerization-inducing agent, such as reverse transcriptase, RNA polymerase and/or DNA polymerase. Examples of DNA polymerases include, but are not limited to, *E. coli* DNA polymerase, Sequenase 2.0®, T4 DNA polymerase or the Klenow fragment of DNA polymerase 1, T3, SP6 RNA polymerase, AMV, M-MLV, and/or Vent polymerase, as well as ThermoSequenase™ (Amersham) or Taquenase™ (ScienTech, St Louis, Mo.). Further examples include thermostable polymerases isolated from *Thermus aquaticus, Thermus thermophilus, Pyrococcus woesei, Pyrococcus furiosus, Thermococcus litoralis*, and *Thermotoga maritima*. The polymerization-inducing agent and nucleotides may be present in a suitable buffer, which may include constituents which are co-factors or which affect conditions such as pH and the like at various suitable temperatures. PCR primers used are preferably single stranded, but double-, triple- and/or higher order stranded nucleotide molecules can be practiced with the present invention. Amplification may be carried out for a number of cycles of PCR, e.g., at least about 10, at least about 20, at least about 30, at least about 35, at least about 40, or at least about 50 cycles in some embodiments.

In some embodiments, more than one nucleic acid (and its corresponding competitive template) are co-amplified, e.g., more than one target nucleic acid and/or more than one other nucleic acid that serves as a reference nucleic acid. In some embodiments, the number of other nucleic acids is at least one. In some embodiments, the number is at least about 50 other nucleic acids, at least 100 other nucleic acids, at least about 200 other nucleic acids, at least about 300 other nucleic acids, at least about 500 other nucleic acids, at least about 800 other nucleic acids, at least about 1,000 other nucleic acids, at least about 5,000 other nucleic acids, at least about 10,000 other nucleic acids, at least about 50,000 other nucleic acids, or at least about 100,000 other nucleic acids. A competitive template can be used for each additional nucleic acid to be evaluated and, in preferred embodiments, a plurality of nucleic acids in a sample can be measured simultaneously.

Other amplification techniques known in the art, described herein, and/or that may be developed, can also be used in some embodiments of the instant invention. For example, amplified fragment length polymorphism ("AFLP") technology may be used. AFLP can bring about selective amplification of restriction fragments from a total digest of genomic DNA. See, e.g., Janssen, et al., "Evaluation of the DNA Fingerprinting Method AFLP as an New Tool in Bacterial Taxonomy," Microbiology, 142(Pt 7):1881-93 (1996); Thomas, et al., "Identification of Amplified Restriction Fragment Polymorphism (AFLP) Markers Tightly Linked to the Tomato Cf-9 Gene for Resistance to *Cladosporium fulvum*,". Plant J, 8(5):785-94 (1995); Vos, et al., "AFLP: A New Technique for DNA Fingerprinting," Nucleic Acids Res, 23(21):4407-14 (1995); Bachem, et al., "Visualization of Differential Gene Expression Using a Novel Method of RNA Fingerprinting Based on AFLP: Analysis of Gene Expression During Potato Tuber Development," Plant J, 9(5):745-53 (1996); and Meksem, et al., "A High-Resolution Map of the Vicinity of the R1 Locus on Chromosome V of Potato Based on RFLP and AFLP Markers," Mol Gen Genet, 249(1); 74-81 (1995).

The ligase detection reaction ("LDR") and/or the ligase chain reaction ("LCR") provide addition methods that may be used in some embodiments of the instant invention. See, e.g., Barany, F., et al., "Cloning, Overexpression, And Nucleotide Sequence Of A Thermostable DNA Ligase Gene," Gene, 109:1-11 (1991), Barany, F., "Genetic Disease Detection And DNA Amplification Using Cloned Thermostable Ligase," Proc. Natl. Acad. Sci. USA, 88:189-193 (1991), and Barany, F., "The Ligase Chain Reaction (LCR) In A PCR World," PCR Methods and Applications, 1:5-16 (1991)). In some embodiments, more than one amplification method may be used, e.g., PCR amplification followed by LDR detection or LCR. See, e.g., Grossman, P. D., et al., "High-Density Multiplex Detection Of Nucleic Acid Sequences: Oligonucleotide Ligation Assay And Sequence-Coded Separation," Nucleic Acids Res., 22:4527-4534 (1994) and Eggerding, F. A., et al., "Fluorescence-Based Oligonucleotide Ligation Assay For Analysis Of Cystic Fibrosis Transmembrane Conductance Regulator Gene Mutations," Human Mutation, 5:153-165 (1995) (detecting 61 cystic fibrosis alleles); Feero, W. T., et al., "Hyperkalemic Periodic Paralysis: Rapid Molecular Diagnosis And Relationship Of Genotype To Phenotype In 12 Families," Neurology, 43:668-673 (1993) (detecting 6 hyperkalemic periodic paralysis alleles); Day, D., et al., "Detection Of Steroid 21 Hydroxylase Alleles Using Gene-Specific PCR And A Multiplexed Ligation Detection Reaction," Genomics, 29:152-162 (1995) and Day, D. J., et al., "Identification Of Non-Amplifying CYP21 Genes When Using PCR-Based Diagnosis Of 21-Hydroxylase Deficiency In Congenital Adrenal Hyperplasia (CA14) Affected Pedigrees," Hum Mol Genet, 5(12):2039-48 (1996) (detecting 20 21-hydroxylase deficiency alleles); White, P. C., et al., "Structure Of Human Steroid 21-Hydroxylase Genes," Proc. Natl. Acad. Sci. USA, 83:5111-5115 (1986) (describing that most of mutations causing 21-hydroxylase deficiency result from recombination between an inactive pseudogene (CYP21P) and a normally-active gene (CYP21), as the two genes share about 98% homology); Day, D., et al., "Detection Of Steroid 21 Hydroxylase Alleles Using Gene-Specific PCR And A Multiplexed Ligation Detection Reaction," Genomics, 29:152-162 (1995) (distinguishing insertion of a single T nucleotide into a $(T)_7$ tract); and Day, D. J., et al., "Identification Of Non-Amplifying CYP21 Genes When Using PCR-Based Diagnosis Of 21-Hydroxylase Deficiency In Congenital Adrenal Hyperplasia (CAH) Affected Pedigrees," Hum Mol Genet, 5(12):2039-48 (1996) (combining PCR/LDR and microsatellite analysis to reveal some unusual cases of PCR allele dropout).

Amplified products can be distinguished; assessed and compared. Step 105 of FIG. 1 illustrates comparing amplified product of target nucleic acid corresponding to a first allele to amplified product of the competitive template for the target nucleic acid; step 106 illustrates comparing amplified product of target nucleic acid corresponding to a second allele to amplified product of the competitive template for the target nucleic acid; and step 107 illustrates comparing amplified product of a reference nucleic acid to amplified product of competitive template for the reference nucleic acid. As used herein "amplified product" can refer to any nucleic acid synthesized at least partly by base-complementary incorporation using another nucleic acid as template. An amplified product may also be referred to an amplicon and/or amplimer herein.

In some embodiments, comparison involves obtaining a relation or relationship, e.g., a first relation reflecting the amplified amounts of target nucleic acid corresponding to a first allele compared with the amplified amounts of competitive template for the target nucleic acid; a second relation reflecting the amplified amounts of target nucleic acid corresponding to a second allele compared with the amplified amounts of competitive template for the target nucleic acid; and a third relation reflecting the amplified amounts of reference nucleic acid compared with amplified amounts of its competitive template. In preferred embodiments, the relation or relationship is provided as a ratio, e.g., a first ratio of the amount of amplified product of target nucleic acid corresponding to the first allele to the amount of amplified product of competitive template for the target nucleic acid; a second ratio of the amount of the amplified product of target nucleic acid corresponding to the second allele to the amount of amplified product of competitive template for the target nucleic acid; and a third ratio of the amount of amplified product of reference nucleic acid to the amount of amplified product of its competitive template.

The adjectives "first," "second," "third" and so forth, as used herein, do not necessarily indicate any order of preference, importance, chronology, or degree of a quality, concentration, and/or amount. Rather the terms are used to differentiate nouns qualified by the adjectives, e.g., a first and a second ratio can mean two different ratios; and a second nucleic acid can mean a different nucleic acid to that referred to as the first nucleic acid. The terms "relation" and "relationship" are used interchangeably, and can refer to any method for comparing values, such as mathematical, computational, statistical, graphical, or other approaches as known in the art.

In some embodiments, obtaining the comparisons, e.g., between the first, second, and/or third ratios, involves measuring the amounts of amplified product of nucleic acid(s) corresponding to various alleles, the competitive template for the nucleic acid(s), the reference nucleic acid(s) and the competitive template(s) for the reference nucleic acid(s). Any method capable of quantifying nucleic acids having a distinguishable feature (e.g., having different sizes, sequences and/or labels) can be used. Quantifying methods may involve separating and/or isolating the amplified product, for example, by use of electrophoresis, solid phase hybridization such as arrays, mass spectrometry, chromatography, HPLC and/or other methods known in the art for separating different nucleic acid molecules. Some embodiments of the instant invention do not use gel electrophoresis and/or some embodiments of the instant invention do not use pyrophosphorolysis.

The electrophoresis used may be one or more of gel electrophoresis (e.g., agarose and/or polyacrylamide gel electrophoresis), capillary electrophoresis (e.g., using a capillary electrophoresis device like PE 310 or a microfluidic CE device like Agilent 2100 or Calipertech AMS 90 high-throughput system), and/or other types of electrophoresis devices known in the art. See, e.g., (G. Gilliland, S. Perrin, K. Blanchard and H. F. Bunn, Proc Natl. Acad. Sci. USA 87, 2725-2729 (1990); M. J. Apostolakos, W. H. Schuermann, M. W. Frampton et al., Analytical Biochemistry 213, 277-284 (1993)). Further, capillary electrophoresis (CE), in particular, microfluidic CE technology can allow measurement of nucleic acid in very small volumes. See, e.g., T. S. Kanigan et al., in Advances in Nucleic Acid and Protein Analyses, Manipulation, and Sequencing, P. A. Limbach, J. C. Owicki, R. Raghavachari, W. Tan, Eds. Proc. SPIE 3926: 172, (2000). Other electrophoresis devices that may be used include, for example, Agilent or AB1 310. In some embodiments, separation of amplified product on agarose gel, a PerkinElmer 310 CE (ABI Prism 310 Genetic Analyzer), and a 2100 Bioanalyzer microfluidic CE (Agilent, Santa Clara, Calif., USA) were shown to provide statistically similar and reproducible results. E. L. Crawford, L. A. Warner, D. A. Weaver and J. C. Willey, *Quantitative end-point RT-PCR expression measurement using the Agilent* 2100 *Bioanalyzer and standardized RT-PCR*. Agilent Application Sep. 2001, 1-8.

Where amplified products are to be separated by electrophoresis, the size of the competitive templates and/or reference nucleic acid(s) can be selected to differ from that of the target nucleic acid. For example, in some embodiments, amplified product generated from the reference nucleic acid and the target nucleic acid are of sufficiently different sizes to be separated by electrophoresis. Further, in some embodiments, amplified product generated from the competitive template for a given nucleic acid and the given nucleic acid are of sufficiently different sizes to be separated by electrophoresis.

In some embodiments, a size difference is achieved by using a competitive template for a given nucleic acid that is longer or shorter that the given nucleic acid, e.g., as described above. In some embodiments, this size differential can be achieved by restriction endonuclease digestion of the amplified product where the competitive template differs from its corresponding nucleic acid by the addition or lack of a restriction endonuclease site. For example, in a specific embodiment, GAPD competitive templates were prepared that separate from native GAPD on the basis of EcoRI or BamHI digestion. Separation on the basis of other restriction endonuclease digestion may also be used. Further, in some embodiments, the same recognition site can be used for both the reference nucleic acid and the nucleic acid to be assessed.

In addition, in some embodiments, the length of the amplified product after restriction endonuclease digestion is a factor to be considered. For example, in certain embodiments, greater nucleic acid size differences are preferred for adequate separation on agarose gels, e.g., preferably about 40, about 50, about 80, about 100 or about 120 base pair differences.

Separated products may be quantified by any methods known in the art and/or described herein, including, for example, use of radiolabeled probes, autoradiography, spectrophotometry and/or densitometry, e.g., densitometry of ethidium bromide stained gels. Quantification methods used may depend on the separation technique employed. For example, other methods that may be used to quantify amplified product include techniques associated with chromatography, e.g., high-performance liquid chromatography (HPLC); gas chromatography; and/or mass spectrometry, e.g., matrix-assisted laser desorption ionization-time-of-flight mass spectrometry (MALDI-TOF-MS) (An economic forecast for the gene expression market http://www.researchandmarkets.com/reports/5545).

In preferred embodiments, nucleic acids and/or amplified products are assessed using immobilization to a support or substrate, e.g., as in an array. Some embodiments, for example, comprise obtaining the first, second, third, etc., relations using an array. "Array" can refer to a substrate or support upon which more than one nucleic acid molecule can be immobilized. Arrays can include, for example, oligonucleotide arrays, including cDNA, DNA, and/or RNA oligonucleotide arrays and high density oligonucleotide arrays. Such arrays may comprise one or more dimensions in the order of macro, micro and or nanometers, providing, e.g., a macroarray, a microarray (e.g., a microfluidic array), and/or a nanoarray. The substrate or support may comprise at least one of a solid support (e.g., glass such as a glass slide, silica, or plastic), a semi-solid support (e.g., a polymeric material, a gel or other matrix), and/or a porous support (e.g., a filter, a nylon membrane or other membrane). The surface of the substrate or support may be planar, curved, pointed, or any suitable two-dimensional or three-dimensional shape on which nucleic acid molecules may be immobilized, including, e.g., beads or microbeads, microwells, a tissue culture dish, pin heads, chips prepared by photolithography, etc. In some embodiments, the surface is UV-analyzable, e.g., UV-transparent, e.g., to facilitate detection of nucleic acids immobilized thereon. Used with some embodiments of the instant invention, such arrays can provide standardized, numerical and/or reproducible measurements of nucleic acids.

Figure 2:
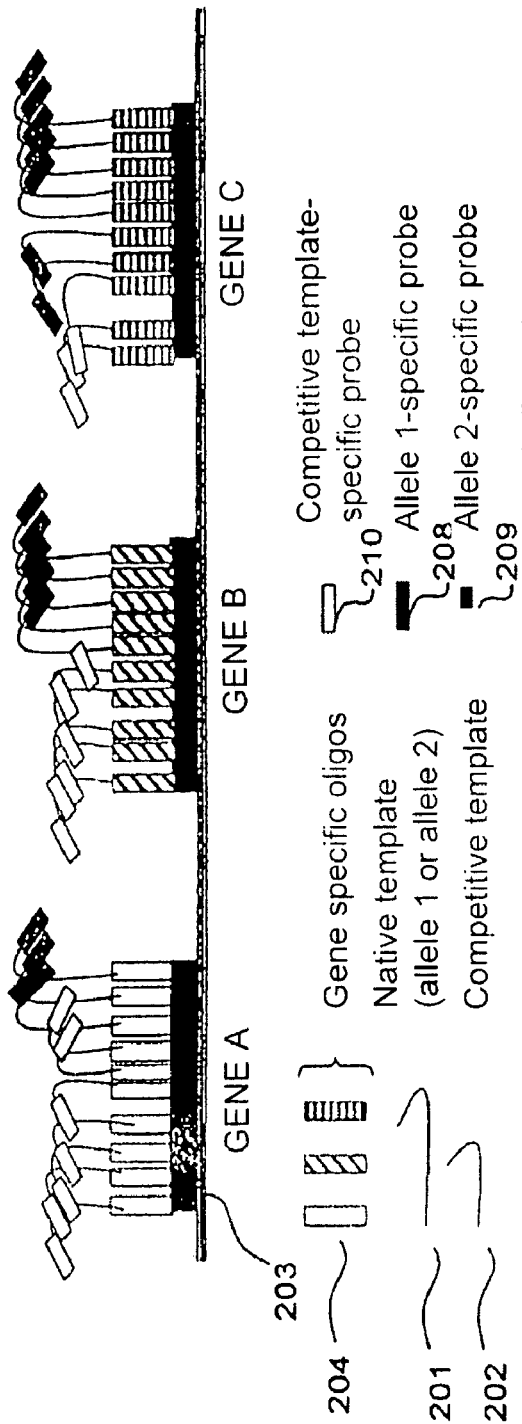
FIG. 2 illustrates microarrays (FIG. 2a) and microbeads (FIG. 2b) used in some embodiments of the instant invention.
Figure 2:
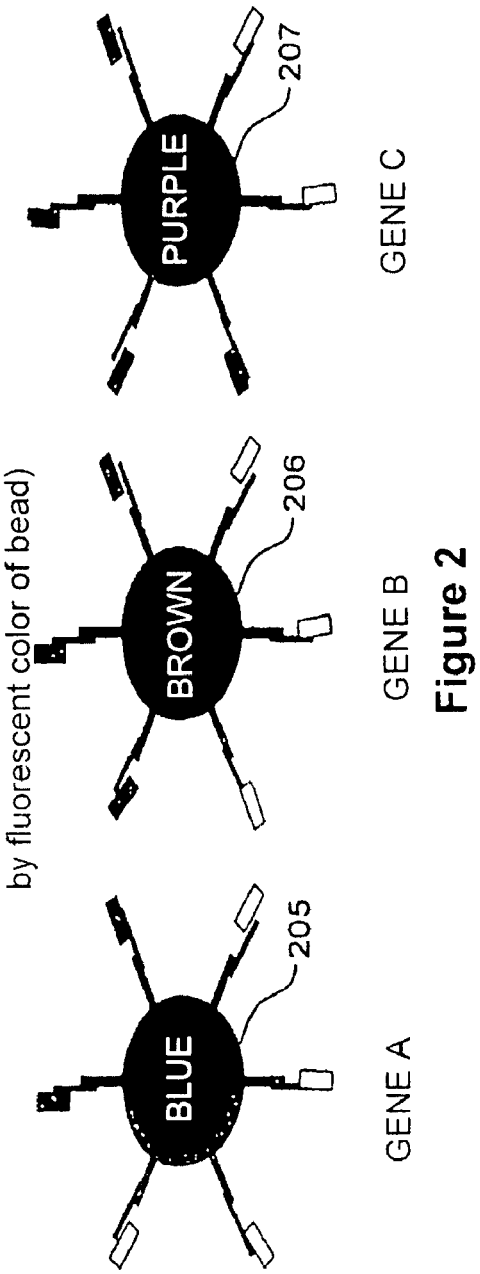

FIG. 2 schematically illustrates microarrays (FIG. 2a) and microbeads (FIG. 2b) used in the practice of some embodiments of the instant invention. In the embodiments illustrated, amplified products of target nucleic acid 201, corresponding to either a first allele (allele 1) or a second allele (allele 2), along with competitive template 202 for the target nucleic acid, are immobilized to a support 203. Immobilization may be achieved in any number of ways, known in the art, described herein, and/or as can be developed. In some embodiments, for example, immobilizing may occur via anchoring a primer, a target nucleic acid, a target nucleic acid-primer complex, and/or a polymerization-inducing agent to a surface. In some embodiments, for example, immobilizing an amplified product can comprise anchoring a primer to a support, e.g., via its 3' end, via its 5' end, via an internal sequence, and/or along its length, anchoring the target nucleic acid to a support, e.g., via its 3' end, via its 5' end, via an internal sequence, and/or along its length, and/or anchoring the amplified product to a support, e.g., via its 3' end, via its 5' end, via an internal sequence, and/or along its length.

Anchoring may involve any technique resulting in direct and/or indirect association of the nucleic acid molecule with the surface, including any means that at least temporarily prevents or hinders its release into a surrounding solution or other medium. The means can be by covalent bonding, non-covalent bonding, ionic bonding, Hydrogen bonding, van der Waals forces, hydrophobic bonding, or a combination thereof. The anchoring may utilize one or more binding-pairs, including, but not limited to, an antigen-antibody binding pair, a streptavidin-biotin binding pair, photoactivated coupling molecules, and a pair of complementary nucleic acids. The anchoring may also involve other physical forces, e.g., an electric and/or magnetic field, centripetal forces, absorbance, capillary action, and the like.

In some embodiments, amplified products are anchored via a capture moiety. A "capture moiety" can be defined as a moiety facilitating immobilization e.g., a moiety that can help anchor a primer, template and/or amplified product to a support. FIGS. 2a and 2b illustrate anchoring using gene-specific oligonucleotides 204 as capture moieties. "Oligonucleotide" is used interchangeably herein with "oligo." The oligonucleotides used may be any length, depending on the desired specificity and hybridization conditions. Preferably the oligonucleotide to be used as the common capture moiety can anchor specific amplified products with high affinity. The oligonucleotide may comprise at least about 30, at least about 50, at least about 60, or at least about 70 bases. In some embodiments, the oligonucleotide used as a common capture moiety may comprise no more than about 80, no more than about 90, no more than about 100, or no more than about 110 bases. In some embodiments, an oligonucleotide with high melting temperature, e.g., greater than about 20 degrees centigrade, greater than about 30 degrees centigrade, greater than about 50 degrees centigrade, greater than about 70 degrees centigrade, or greater than about 80 degrees centigrade, can be used.

The gene-specific oligonucleotides are coupled to the support 203 at one end and hybridize to amplified product of a nucleic acid corresponding to a given gene at the opposite end, thereby facilitating immobilization. Other approaches can be used, e.g., as known in the art, described herein, or as can be developed. Also, other capture moieties may be used in some embodiments of the instant invention. Examples include polypeptides and proteins, e.g., immobilized enzymes, such as transcription factors or restriction endonucleases, which and recognize and couple to specific nucleic acid sequences; protein-nucleic acid complexes e.g., ribonuclear complexes, and/or other moieties that can capture one or more nucleic acid sequences.

In some embodiments, more than one type of nucleic acid is recognized by a common capture moiety. For example, a common capture moiety can anchor both native and competitive templates and/or amplified products thereof to a support, e.g., by recognizing and hybridizing to a common sequence and/or feature in the different nucleic acids. In preferred embodiments, amplified products of target nucleic acid corresponding to a first allele, of target nucleic acid corresponding to a second allele, and of competitive template for the target nucleic acid are immobilized by a common capture moiety.

FIG. 2a, for example, illustrates microarrays comprising gene-specific oligonucleotides 204 that recognize and hybridize to amplified products of nucleic acids corresponding to a given gene, including amplified products of target nucleic acid corresponding to allele 1, of target nucleic acid corresponding to allele 2, and of competitive template for the target nucleic acid. In FIG. 2, a first common capture moiety (gene-specific oligonucleotide) anchors nucleic acids corresponding to gene A (open bars), a second common capture moiety anchors nucleic acids corresponding to gene B (slashed bars); and a third common capture moiety anchors nucleic acids corresponding to gene C (striped bars). As one of skill in the art will appreciate, more or less than three common capture moieties may be used, e.g., to assess more or less than three target nucleic acids, e.g., corresponding to more or less than 3 genes.

Common capture moieties that immobilize amplified products of nucleic acids corresponding to different genes can be localized in different positions on an array, e.g., anchored to the substrate or support at different locations. "Different positions" on an array can refer to different regions, areas, spots, locations or addresses that are spatially distinguishable, e.g. by being spotted at different positions on a filter, slide surface, or other substrate or support as known in the art and/or provided herein. Different positions on an array may also indicate localization in different vessels, including micro-wells or other depressions on an array; or localization on different microbeads (or on different batches of microbeads) that are themselves spatially and/or spectrally distinguishable.

FIG. 2a, for example, illustrates that the 3 different common capture moieties anchor nucleic acids corresponding to the 3 different genes (genes A, B, and C) in different positions on the surface of the array. Accordingly, amplified products corresponding to different genes may be grouped in different regions, areas, spots, locations or addresses that are spatially distinguishable. Other approaches for distinguishing amplified product corresponding to different genes may also be used, e.g., in other embodiments.

FIG. 2b illustrates an approach where the 3 different common capture moieties anchor nucleic acids corresponding to the 3 different genes (genes A, B, and C) on different microbeads. The microbeads may themselves be distinguished spatially (e.g., by being located in different positions) and/or spectrally (e.g., by being labeled with different detection moieties). FIG. 2b illustrates the situation where nucleic acids corresponding to gene A are anchored to a "blue" microbead 205; nucleic acids corresponding to gene B are anchored to a "brown" microbead 206; and nucleic acids corresponding to gene C are anchored to a "purple" microbead 207, e.g., where the different colors represent distinguishable detection moieties. A detection moiety can be any moiety that facilitates detection in a detection system, including, but not limited to, fluorescent moieties, enzyme moieties (e.g., ELISA, as well as enzyme-based histochemical assays), radioactive moieties, chromophore, quantum dots, and luminescent systems.

In some embodiments, immobilized amplified products corresponding to a given target nucleic acid are also distinguished using different detection moieties. FIGS. 2a and 2b further illustrate the use of different detection moieties to distinguish different amplified products corresponding to a given gene. FIGS. 2a and 2b illustrate, e.g., a detection moiety specific for a first allele (allele 1 specific probe) 208, a detection moiety specific for a second allele (alle 2 specific probe) 209, and a detection moiety specific for the competitive template for the target gene (competitive template specific probe) 210.

A detection moiety is said to be specific for an amplified product when it allows detection of that amplified product preferentially over one or more other available amplified products. Detection moieties specific for an amplified product may comprise, e.g., a fluorescent probe and/or labeled enzyme that recognizes and couples, binds, hybridizes, attaches and/or otherwise becomes adhered to a specific sequence. For example, the competitive template specific probe may be complementary to sense sequences of the competitive template that span the 3' end of the reverse primer. The term "probe" generally refers to an oligonucleotide, whether occurring naturally as in a purified restriction digest or produced synthetically, recombinantly or by PCR amplification, which is capable of hybridizing to another nucleic acid of interest. A probe can be single-stranded, double-stranded, and the like, and may comprise either sense or anti-sense sequences, e.g., complementary and specific to either anti-sense or sense sequences of amplified products, respectively. A probe may be of any length depending on the desired specificity and hybridization conditions, such as at least about 10 bases, at least about 15 bases, at least about 20 bases, at least about 25 bases, at least about 30 bases, and the like. In some embodiments, a probe with high melting temperature, e.g., greater than about 70 degrees centigrade, can be used.

A probe specific for an allelic variation is generally complementary to a sequence including the locus of the allele and of sufficient length to facilitate desired specificity. For example, a probe specific for a point mutation may comprise about 10 to about 20 bases complementary to about 10 to about 20 bases of the sequence including the point mutation.

Detection moieties for more than one target nucleic acid (e.g., multiple genes) can be mixed in known amounts. The amounts of different amplified products may be obtained by detecting different detection moieties at different positions on the array, e.g., as discussed in more detail below. Amplified products corresponding to different genes may be co-amplified separately and applied to the array separately, or may be co-amplified separately and then pooled before being applied to the array, or may be co-amplified in the same vessel.

In some embodiments, the different amplified products may be directly labeled with a detection moiety, e.g., to distinguish amplified product corresponding to different target nucleic acids and/or to distinguish amplified product of target nucleic acid corresponding to various alleles and/or amplified product of competitive template for the target nucleic acid. For example, one or more of the nucleotides in an amplification reaction may be labeled with a detection moiety. Where a target nucleic acid and its competitive template are co-amplified in a given vessel, including different detection moieties in different vessels can produce amplified products corresponding to different target nucleic acids that are distinguishably labeled. In still some embodiments, amplified product of target nucleic acid corresponding to various alleles and/or amplified product of competitive template for the target nucleic acid can be distinguished by being anchored to different positions, e.g., different location on a microarray, and/or to different microbeads. One of skill in the art will appreciate that the approach used may depend on the type of alleles being measured, available samples, intended application, and the like. However, some embodiments of the instant invention do not use two-color labeling, e.g., where two-color labeling refers to a situation where a given molecule of an amplified product is labeled with two colors, e.g., with two different fluorescent labels hybridized or otherwise attached to the given molecule.

FIG. 3 schematically illustrates assessing allele frequency of SNPs in preferred-embodiments of the instant invention. In the illustrated embodiment, the competitive template for the target nucleic acid comprises a shortened sequence, omitting the allelic SNP region of the corresponding target, e.g., as described above. An oligonucleotide anchored to a support along its length is used as a common capture moiety for amplified products corresponding to the target nucleic acid, including amplified products of the target nucleic acid corresponding to a first allele, of said target nucleic acid corresponding to a second allele and of the competitive template for the target nucleic acid. For example, a region of the competitive template between its forward primer and the 3' end of its reverse primer can be evaluated for homology with the corresponding native template of the target nucleic acid.

In the illustrated embodiment, the oligonucleotide comprises a 70-mer sequence homologous to a region shared by the anti-sense strand of amplified products of target nucleic acid corresponding to both alleles and of amplified product of the competitive template. The oligonucleotide common capture moieties are localized in different positions on an array, e.g., at first, second, and third positions on a slide surface.

Other approaches may be used, e.g., using an oligonucleotide homologous to a region shared by the sense stand of amplified products, using an oligonucleotide of a different length, using an oligonucleotide anchored via its 5' or 3' end, and/or using other types of common capture moieties, e.g., enzymes, as known in the art and/or as provided herein. Further, in some embodiments, common capture moieties may be present on different microbeads, e.g., as described above.

Products obtained from co-amplifying target nucleic acid and its corresponding competitive template may be applied to the array, e.g., at the positions of capture moieties, under conditions facilitating hybridization. After washing to remove un-hybridized products, the immobilized amplified products can be distinguished using fluorescent probes as detection moieties, again followed by allowing for hybridization and removing un-hybridized products by washing.

Figure 3A:
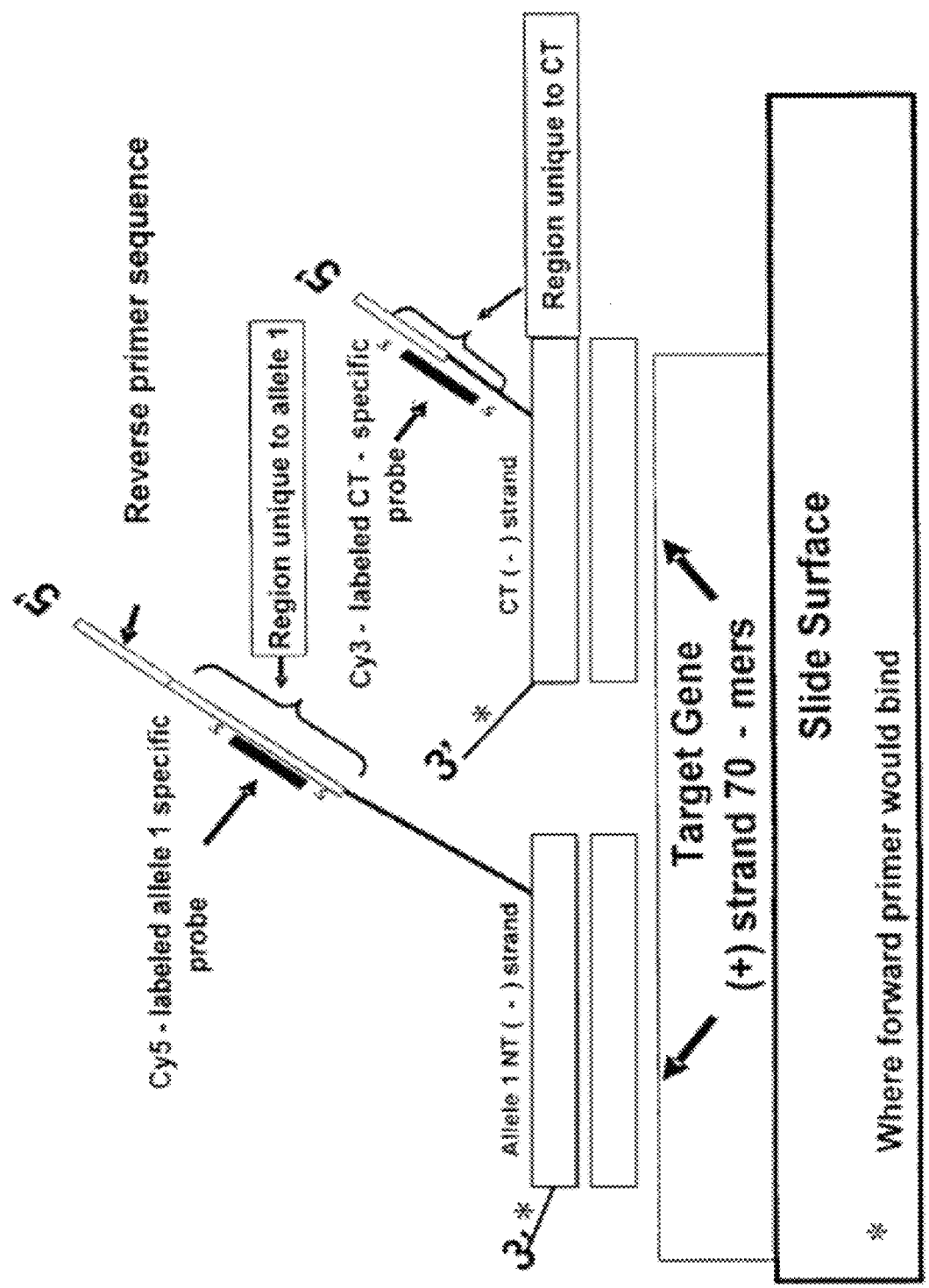
FIG. 3a-d illustrates assessing allele frequency of SNPs in some embodiments of the instant invention.

FIG. 3a illustrates a first position where amplified products are immobilized and distinguished using an allele 1 specific probe and a competitive template specific probe. In the illustrated embodiment, e.g., the allele 1 specific probe comprises a Cy5-labeled sense oligonucleotide complementary to an antisense sequence in the amplified product of target nucleic acid corresponding to the first allele, but not present in amplified product corresponding to the second allele, nor the competitive template. For example, a region 3' to the region homologous to the reverse primer can provide a sequence unique to the first allele. The competitive template specific probe comprises a Cy3-labeled sense oligonucleotide complementary to an antisense sequence in the amplified product of the competitive template, but not present in amplified products of target nucleic acid corresponding to first or to second alleles. For example, a sequence at a juncture between the native sequence and the region homologous to the reverse primer can provide a sequence unique to the competitive template.

After allowing for hybridization and washing, amplified products are assessed by detecting Cy5 and Cy3 fluorescence. That is, measuring and comparing the fluorescence due to Cy5 (allele 1 specific probe) with that due to Cy3 (competitive template specific probe) permits a comparison of the amount of amplified product of target nucleic acid corresponding to the first allele to the amount of amplified product of the competitive template for the target nucleic (Step 105 of FIG. 1). In preferred embodiments, neither of the two probes added at the first position binds or binds substantially to amplified product of target nucleic acid corresponding to the second allele, so that no or substantially no amplified products of target nucleic acid corresponding to the second allele contribute to the fluorescent measurements at this first position.

Figure 3B:
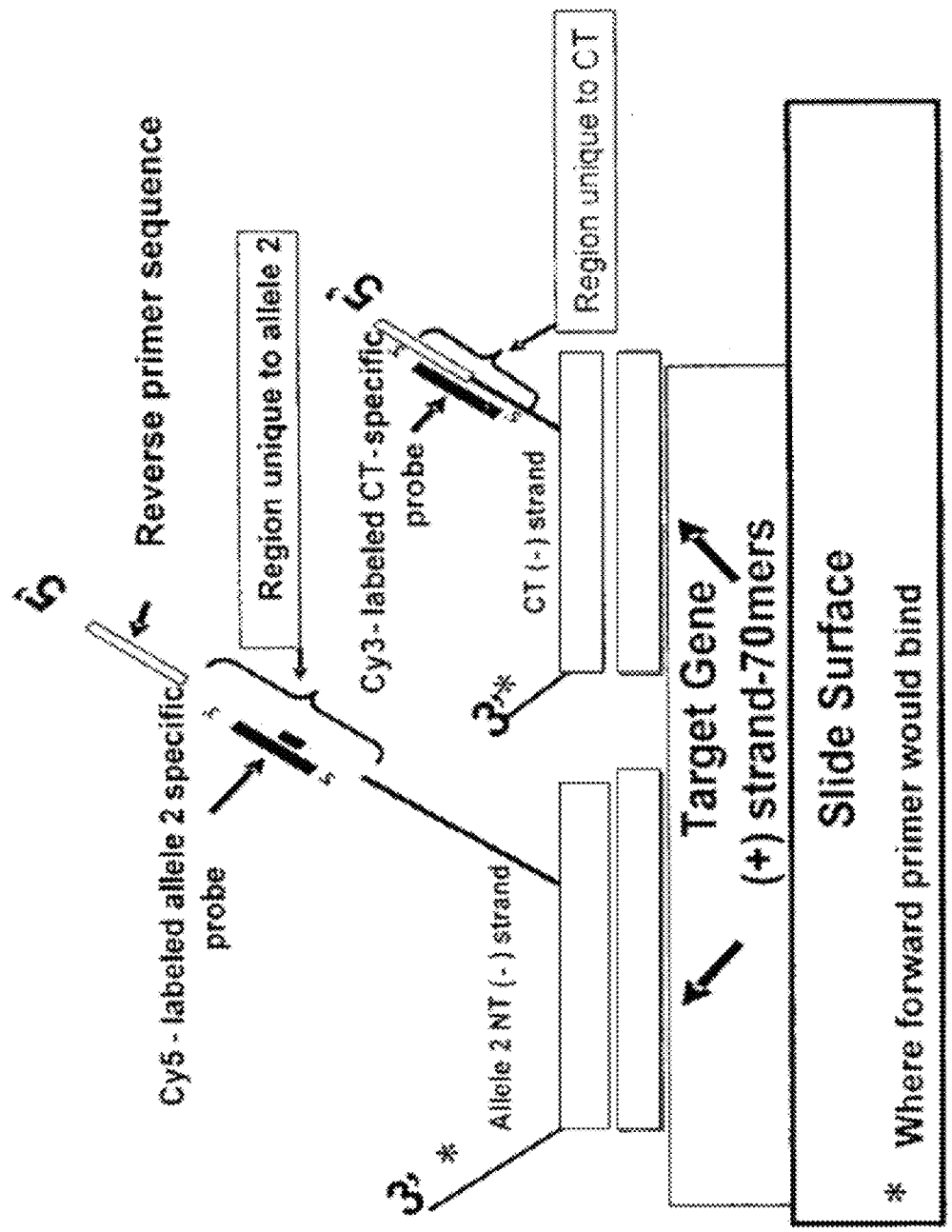

FIG. 3b illustrates a second position where amplified products are immobilized and distinguished using an allele 2 specific probe and a competitive template specific probe. In the illustrated embodiment, e.g., the allele 2 specific probe comprises a Cy5-labeled sense oligonucleotide complementary to an antisense sequence in the amplified product of target nucleic acid corresponding to the second allele, but not present in amplified product corresponding to the first allele, nor in the competitive template (that is, a sequence unique to the second allele).

This probe, along with the competitive template specific probe of FIG. 3a, can be applied to the second position, and amplified products assessed by detecting Cy5 and Cy3 fluorescence (preferably after allowing for hybridization and washing). Measuring and comparing the fluorescence due to Cy5 (allele 2 specific probe) with that due to Cy3 (competitive template specific probe) permits a comparison of the amount of amplified product of target nucleic acid corresponding to the second allele to the amount of amplified product of the competitive template for the target nucleic (Step 106 of FIG. 1). In preferred embodiments, neither of the two probes added at the second position binds or binds substantially to amplified product of target nucleic acid corresponding to the first allele, so that no or substantially no amplified product of target nucleic acid corresponding to the first allele contributes to the fluorescent measurements at this second position.

Figure 3C:
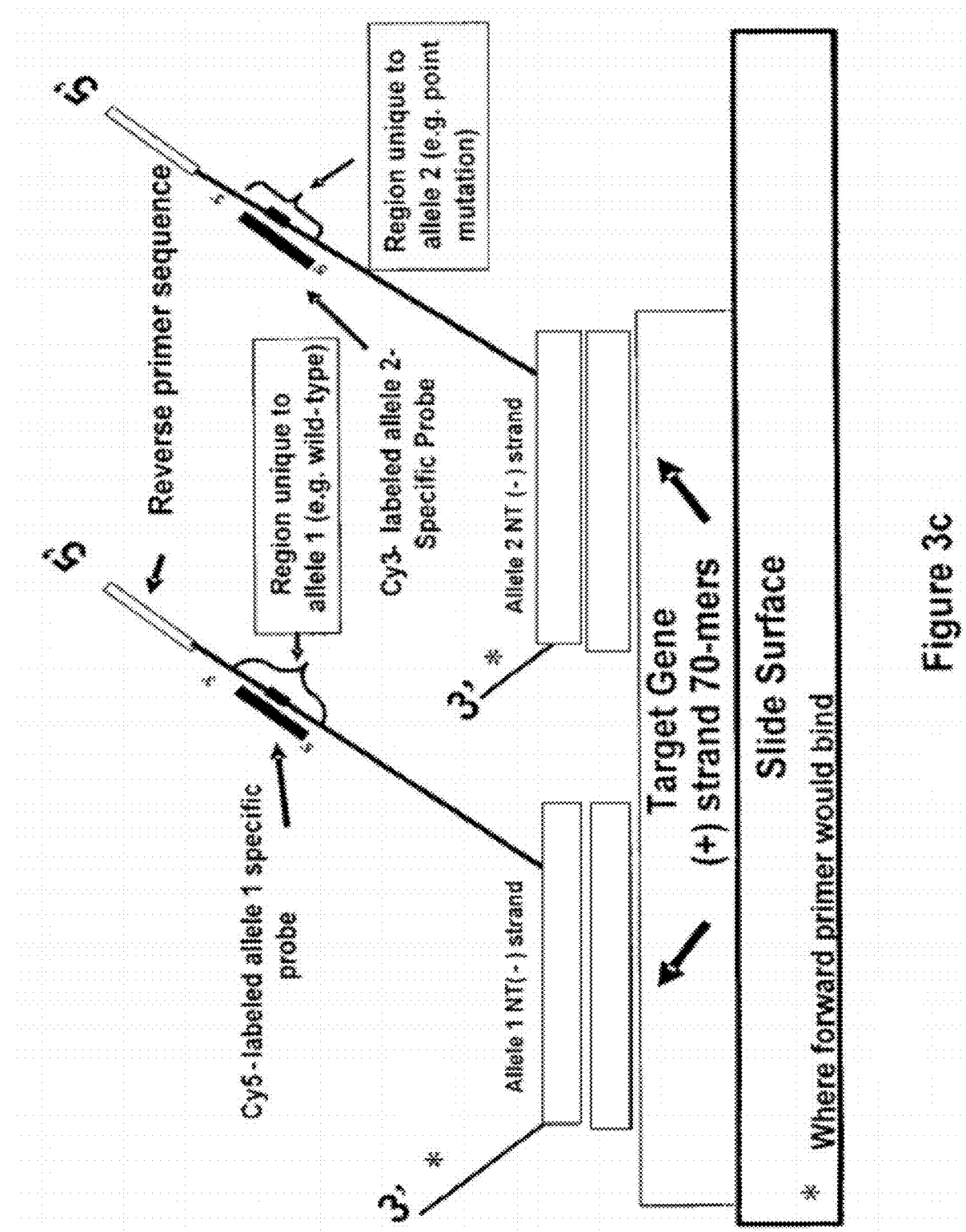

FIG. 3c illustrates a third position where amplified products are immobilized and distinguished using allele 1 specific and allele 2 specific probes. In the illustrated embodiment, e.g., the Cy5-labeled allele 1 specific probe of FIG. 3a is used with a Cy3-labeled allele 2 specific probe. Measuring and comparing the fluorescence due to Cy5 (allele 1 specific probe) with that due to Cy3 (allele 2 specific probe) permits a comparison of the amount of amplified product of target nucleic acid corresponding to the first allele to the amount of amplified product of target nucleic acid corresponding to the second allele. The ratio can provide a measure of the ratio of the first allele to the second allele before amplification and can provide a quality control for allelic frequency measurements using measurements obtained at the first and second positions, as described in more detail below. In preferred embodiments, neither of the two probes added at this third position binds or binds substantially to amplified product of competitive template for the target nucleic and/or no or substantially no amplified products of the competitive template for the target nucleic acid contributes to the fluorescent measurements at this third position.

Figure 3D:
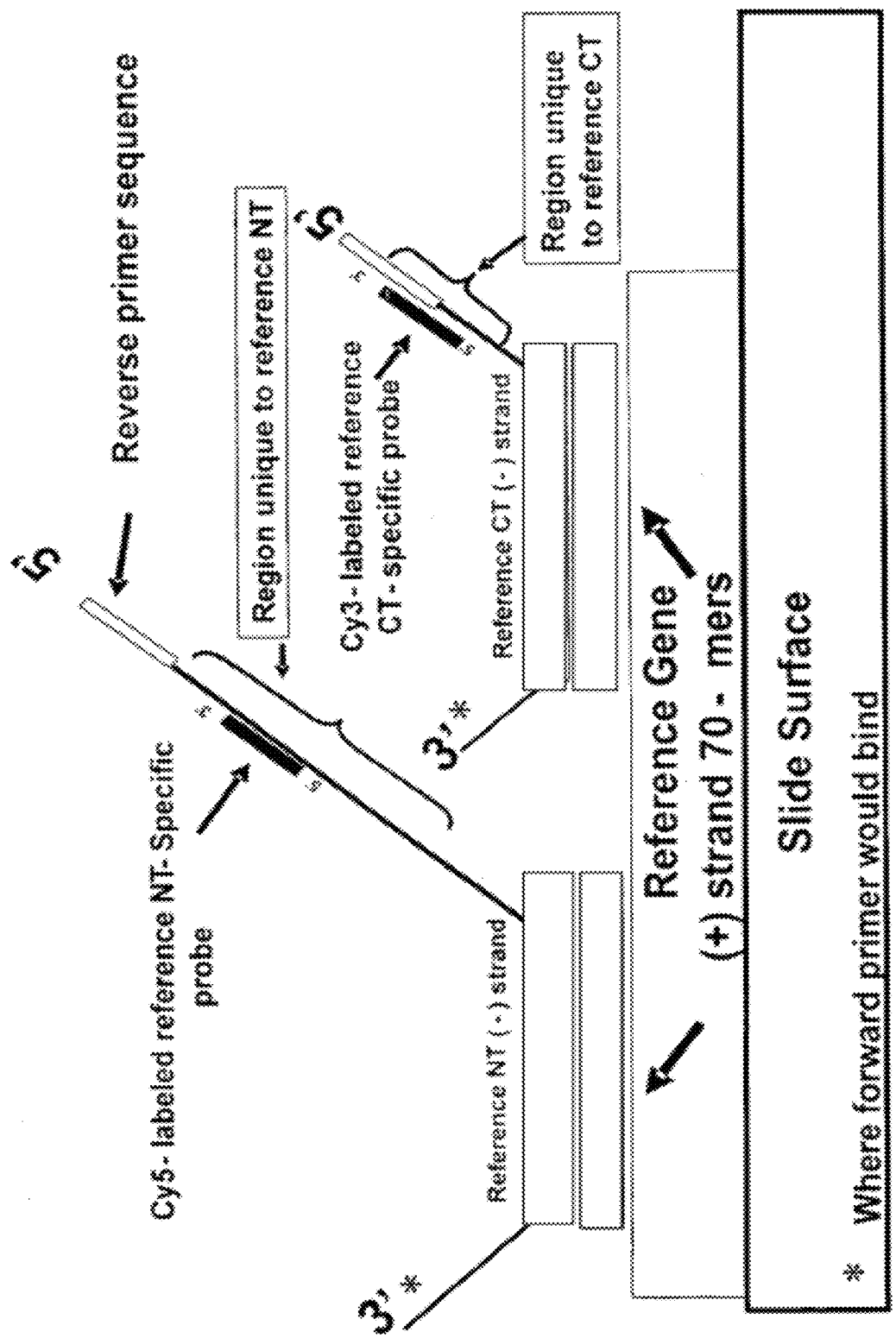

FIG. 3d illustrates assessing amplified product of a reference nucleic acid and its competitive template, e.g., to normalize measurements of the target nucleic acid, e.g., as described above. FIG. 3d, for example, illustrates a position where amplified products of a reference nucleic acid and its competitive template are immobilized. In the illustrated embodiment, a 70-mer oligonucleotide anchored to the support along its length serves as the common capture moiety for amplified products of the reference nucleic acid and its competitive template. Reference nucleic acid-specific oligonucleotides may be localized at one or more positions on a slide surface. Products obtained from co-amplifying the reference nucleic acid and its competitive template may be applied to the array, e.g., at positions of the reference nucleic acid-specific oligonucleotides, under conditions facilitating hybridization. Again, after washing to remove un-hybridized products, the immobilized amplified products can be distinguished using fluorescent probes as detection moieties, preferably again followed by hybridization and washing.

In the illustrated embodiment, e.g., the immobilized amplified products are distinguished using a Cy5-labeled reference native template specific probe and a Cy3-labeled reference competitive template specific probe. Measuring and comparing the fluorescence due to Cy5 with that due to Cy3 permits a comparison of the amount of amplified product of reference nucleic acid to the amount of amplified product of its competitive template (Step 107 of FIG. 1). The comparisons obtained in steps 105, 106, and 107 of FIG. 1 can provide first, second and third relations, respectfully, as described above. Example I provides additional details for assessing allelic frequency of a catalase gene mutation.

In some embodiments, the relations themselves can be compared, e.g., to assess either or both alleles and/or obtain allelic frequency. For example, in some embodiments allelic frequency can be obtained by comparing one of the first, second, or third relations described above to one or both of the other two relations. In preferred embodiment, one of the first, second or third relations describe-above is compared to the other two relations, as described in more detail below.

In preferred embodiments, the amount of amplified product of target nucleic acid corresponding to a given allele is compared to reference nucleic acid, e.g., where the reference nucleic acid is itself compared to its competitive template. For example, the first relation comparing amplified product of target nucleic acid corresponding to a first allele to amplified product of competitive template for the target nucleic acid can be compared to the third relation, comparing amplified product of reference nucleic acid to amplified product of its competitive template. Similarly, the second relation comparing amplified product of target nucleic acid corresponding to a second allele to amplified product of competitive template for the target nucleic acid can be compared to the third relation, comparing amplified product of reference nucleic acid to amplified product of its competitive template.

In some embodiments, a relation reflecting how the first and/or second relation compares with the third relation can be obtained. In some embodiments, a pair of relations is obtained, comparing each of the first and second ratios to the third ratio, e.g., providing a pair of "ratios of ratios." Each of the pair of ratio of ratios can provide to a numerical value, preferably corresponding to an absolute number of copies of each allele in the sample. In preferred embodiments, each of the pair of ratio of ratios can be compared to each other, e.g., to provide allelic frequency. Further, allelic frequency can be (more directly) obtained, e.g., using the measurements obtained at the third position (FIG. 3c). This can provide a quality control for allelic frequency measurements using measurements obtained at the first and second positions. In some embodiments, this provides a quality control for SNP analyses. Further, in some embodiments, the first relation is compared with the second and third relations. In some embodiments, the second relation is compared with the first and third relations. Those of skill in the art will appreciate that a number of other comparisons may be used to assess amount of each allele and/or determine allelic frequency, as well as to provide quality controls for other measurements. In some embodiments, numerical values and/or allelic frequencies for various measured alleles are provided as a database, as described in more detail below. For example, such a database can be used with gene expression data in clinical diagnostic testing.

In more preferred embodiments, the relation obtained by comparing two or more other relations, e.g., by comparing the first or second ratios to the third ratio, remains substantially constant beyond the exponential phase of amplification of the target nucleic acid. Substantially constant can refer to variations of +/− about 1%, about 5%, about 10%, about 15%, or about 20% of an absolute constant number. Accordingly, comparing first, second and third relations, as discussed above, can provide a measure of the relative representation of first and second alleles before amplification, even where amplification extended to the end point and/or plateau phase.

One of skill in the art will appreciate other approaches for assessing amounts of amplified products. For example, in some embodiments of the instant invention, amounts of amplified products can be assessed using mass spectrometry. Such embodiments can provide reagents for assessing allele frequency using mass spectrometry, such as matrix-assisted laser desorption ionization time-of-flight (MALDI-TOF) analysis.

Amplified products themselves can be distinguished by mass and/or the different detection moieties can be distinguished by mass. In such embodiments, for example, detection moieties can comprise probes that are mass labeled and/or are amenable to mass labeling. Mass labels include any moiety that facilitates separation and/or quantification based on mass, including, e.g., one or more incorporated dNTPs, ddNTPs, and/or other chain terminators that produce a detectable mass difference. For example, in some embodiments, dye-labeled ddNTPs are used.

FIG. 4 illustrates assessing allele frequency of SNPs using mass labeled probes in some embodiments of the instant invention. The mass labeled probes are used to assess amplified products that correspond to amplified products discussed in FIG. 3, and are similarly immobilized on an array. In this approach, however, the probes used need not be labeled before addition to the immobilized amplified products. Rather, the probes can be mass labeled by an extension method following hybridization to the amplified products, where extension occurs in presence of mass-labeled nucleotides. In such embodiments, the hybridized probe can serve as a primer so that, under conditions allowing polymerization, a polymerization-inducing agent incorporates nucleotides to the 3' end of the probe. Where ddNTP and/or other chain terminators are used, polymerization can be terminated upon the incorporation of one or more such bases.

Figure 4A:
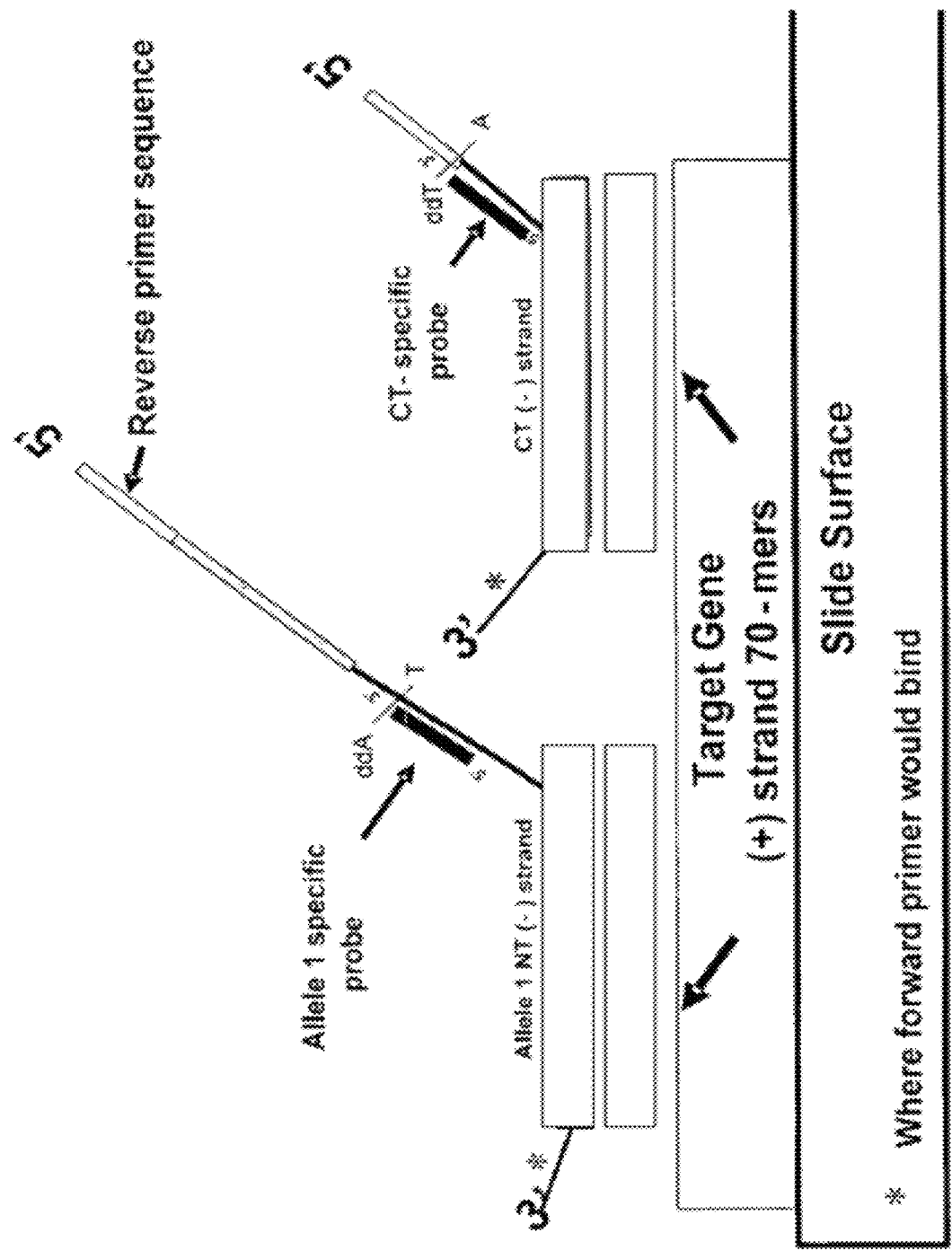
FIG. 4a-d illustrates assessing allele frequency of SNPs using mass labeled probes in some embodiments of the instant invention.

FIG. 4a illustrates a first position where amplified products are immobilized and a probe is added that hybridizes amplified product of both the first allele and competitive template for the target nucleic acid. The probe can be designed to hybridize 3' to a distinguishing feature between the target and its competitive template, so that upon polymerization, different nucleotides bearing distinguishable mass labels are incorporated.

FIG. 4a illustrates an oligonucleotide probe, e.g., that hybridizes amplified product of competitive template immediately 3' to the region of the competitive template complementary to its reverse primer. Under conditions facilitating polymerization, a base corresponding to the 3' base of the reverse primer will be incorporated, e.g., a T in the embodiment illustrated. Rather than a T, the probe hybridized to the corresponding sequence in the amplified product of the target nucleic acid corresponding to the first allele will be extended by an A, corresponding to the next native base immediately 5' to the region of hybridization. At this first position, the A and T nucleotides provided are distinguishably labeled, e.g., with detection moieties sufficiently different in mass to permit separation of the probes by MALDI-TOF. In the illustrated embodiment, ddATP and ddTTP are used, preventing incorporation of further nucleotides. Measuring and comparing the amounts of the ddA-extended probe with that of the ddT-extended probe permits a comparison of the amount of amplified product of target nucleic acid corresponding to the first allele to the amount of amplified product of the competitive template for the target nucleic acid (Step 105 of FIG. 1).

Figure 4B:
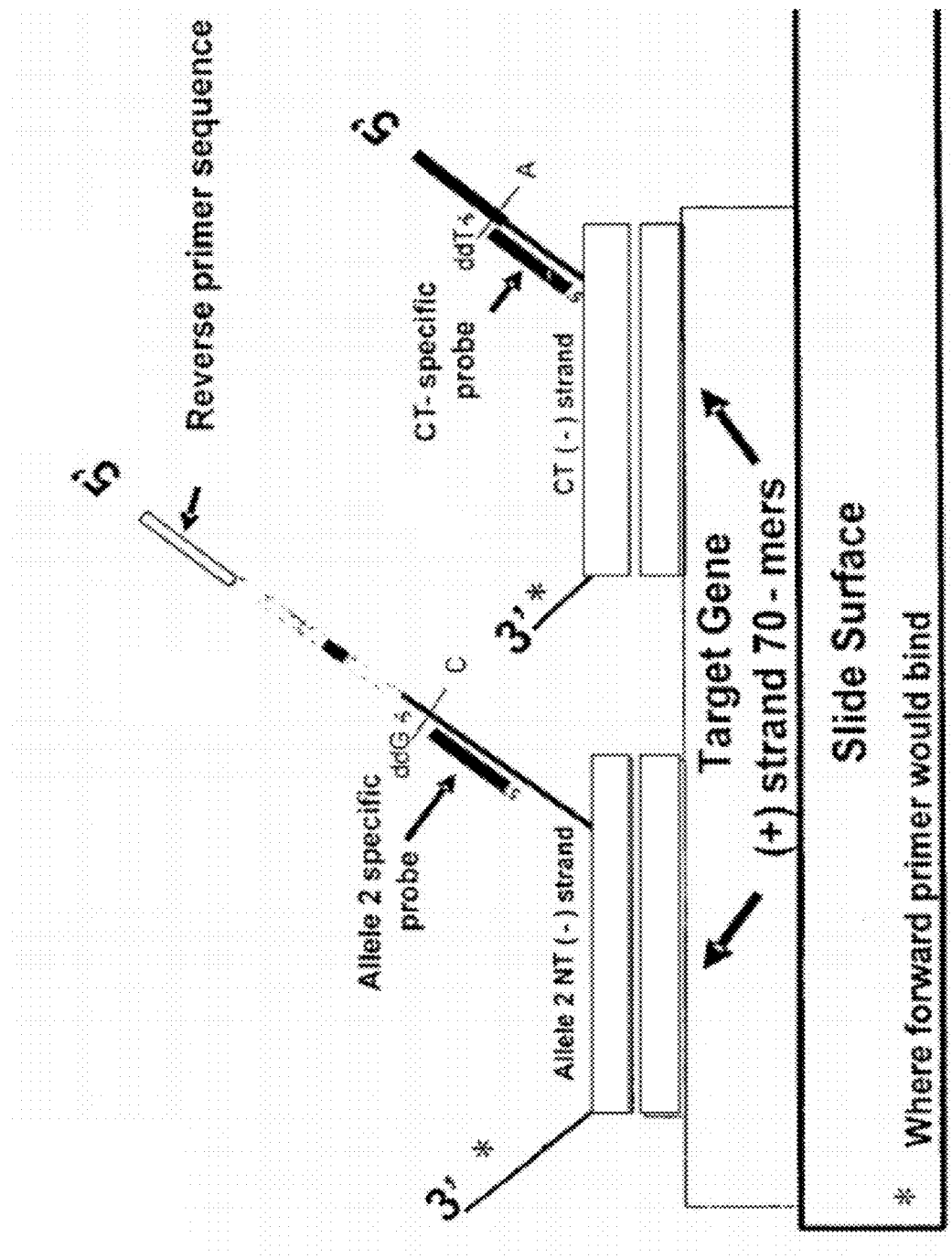

FIG. 4b illustrates a second position where amplified products are immobilized and a probe is added that hybridizes amplified product of both the second allele and competitive template for the target nucleic acid. The probe that hybridizes to amplified product of competitive template is extended by a T; while the probe that hybridizes to the corresponding sequence in the amplified product of the target nucleic acid corresponding to the second allele is extended by a G, instead of T and instead of an A. At this second position, the G and T nucleotides provided can be distinguishably labeled, e.g., with detection moieties sufficiently different in mass to permit separation of the probes by MALDI-TOF. In the illustrated embodiment, ddGTP and ddTTP are used, preventing incorporation of further nucleotides Measuring and comparing the amounts of the ddG-extended probe with that of the ddT-extended probe permits a comparison of the amount of amplified product of target nucleic acid corresponding to the second allele to the amount of amplified product of the competitive template for the target nucleic (Step 106 of FIG. 1).

Figure 4C:
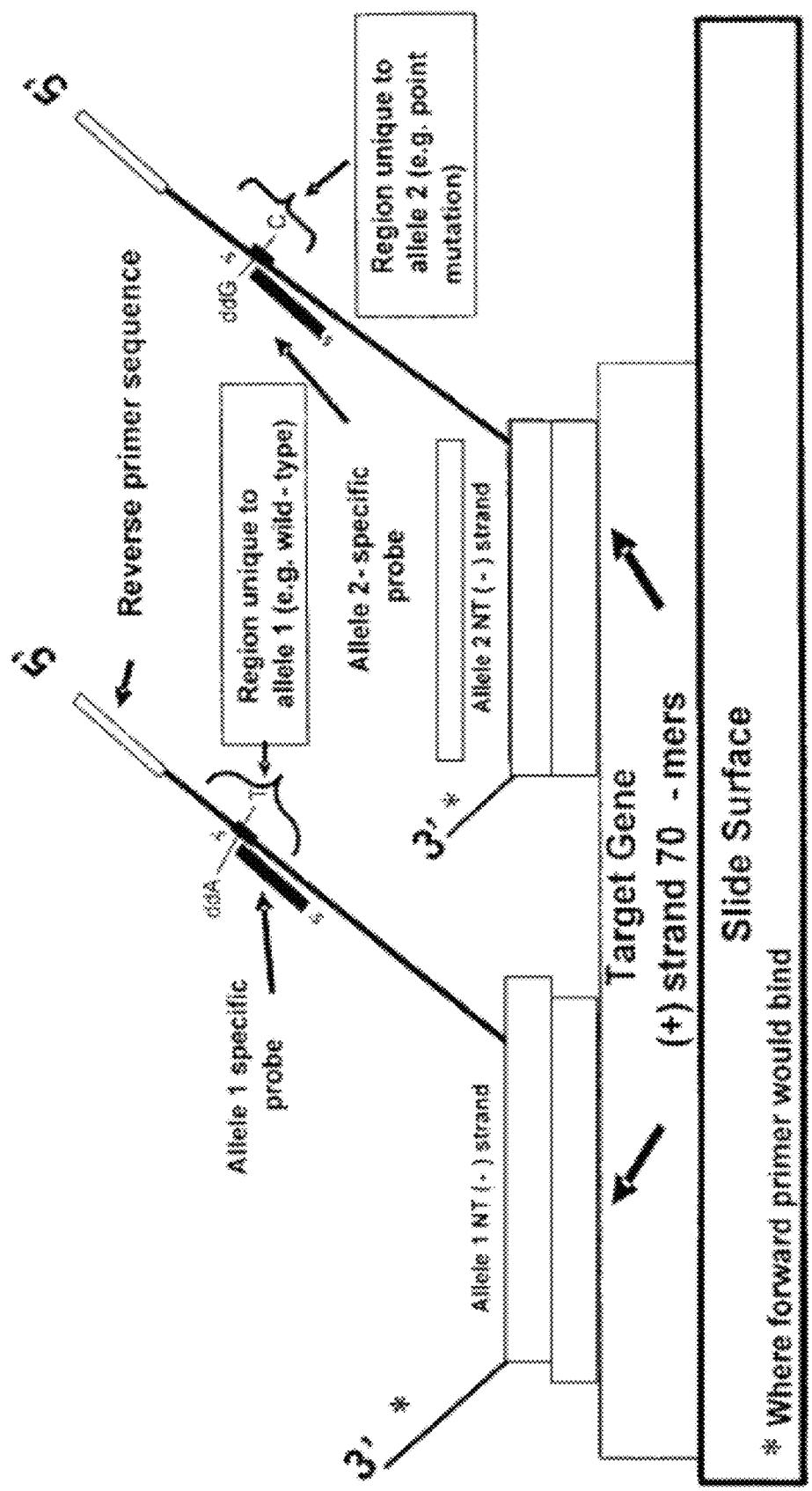

FIG. 4c illustrates a third position where amplified products are immobilized and a probe is added that hybridizes amplified product of both the first and second alleles of the target nucleic acid. The probe can be designed to hybridize 3' to a region of allelic variation, e.g., 3' to a point mutation where the first allele comprises a T and the second allele comprises a C. Under conditions facilitating hybridization, the probe that hybridizes to amplified product of target nucleic acid corresponding to the first allele is extended by an A; while the probe that hybridizes to the corresponding sequence in the amplified product of the target nucleic acid corresponding to the second allele is extended by a G. At this third position, the G and T nucleotides provided can be distinguishably labeled, e.g., with detection moieties sufficiently different in mass to permit separation of the probes by MALDI-TOF. In the illustrated embodiment, ddATP and ddGTP are used, preventing incorporation of further nucleotides. Measuring and comparing the amounts of the ddA-extended probe with that of the ddG-extended probe permits a comparison of the amount of amplified product of target nucleic acid corresponding to the first allele to the amount of amplified product of target nucleic acid corresponding to the second allele. The ratio can provide a measure of the ratio of the first allele to the second allele before amplification and can provide a quality control for allelic frequency measurements using measurements obtained at the first and second positions, as described in more detail below. In some embodiments, the first, second, and third positions of FIG. 4 can be collapsed into two positions or one position, e.g., one position where distinguishably labeled ddA, ddT, and ddG nucleotides are provided.

Figure 4D:
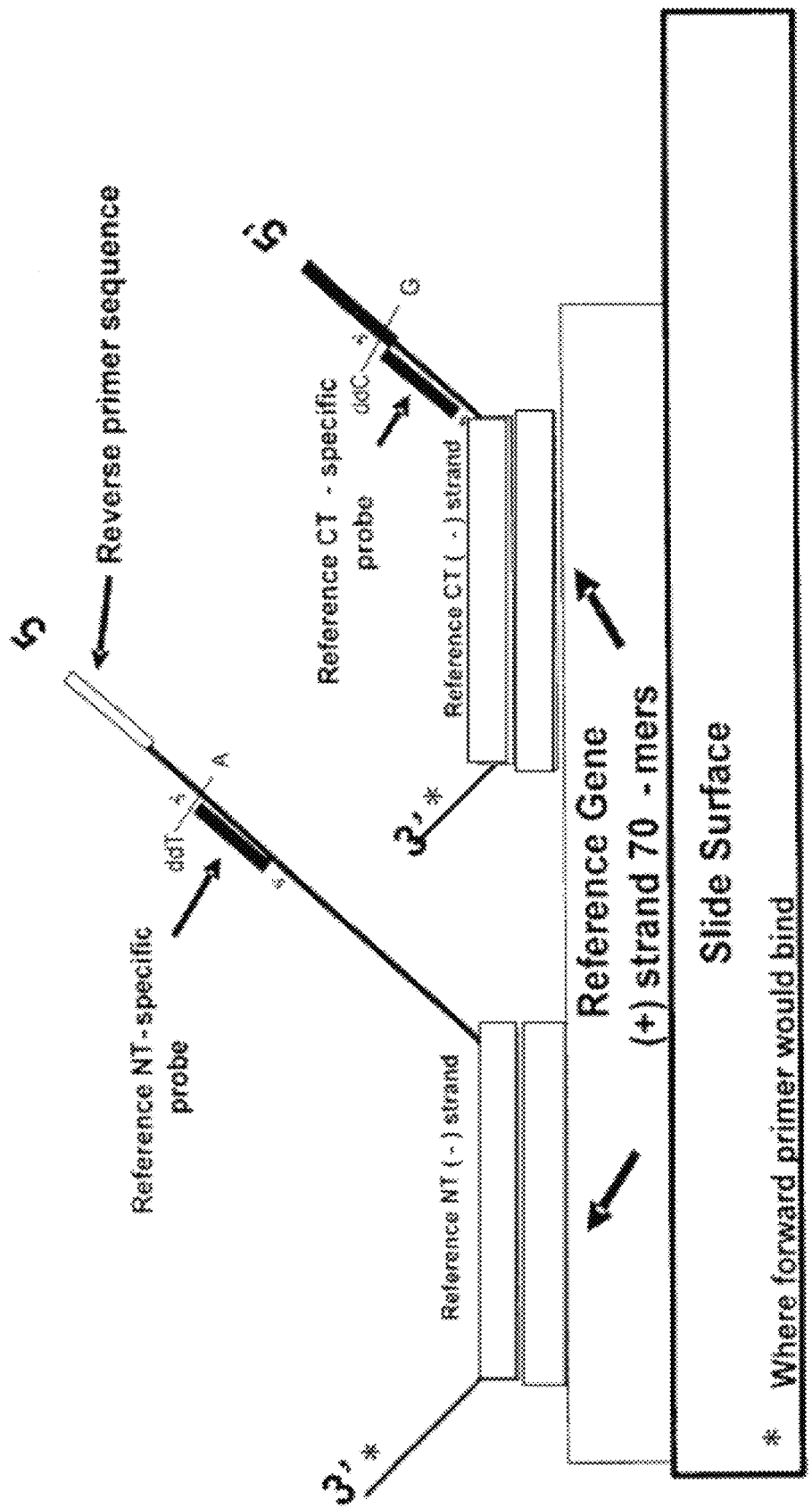

FIG. 4d illustrates a mass labelling approach for distinguishing reference nucleic acid from its competitive template. Here amplified products are immobilized and a probe is added that hybridizes amplified product of both the reference nucleic acid and its competitive template. The probe can be designed to hybridize 3' to a distinguishing feature between the reference and its competitive template, so that upon polymerization, different nucleotides bearing distinguishable mass labels are incorporated.

FIG. 4d illustrates an oligonucleotide probe, e.g., that hybridizes amplified product of reference competitive template immediately 3' to the region of the reference competitive template complementary to its reverse primer. Under conditions facilitating polymerization, a base corresponding to the 3' base of the reverse primer will be incorporated, e.g., a C in the embodiment illustrated. Rather than a C, the probe hybridized to the corresponding sequence in the amplified product of the reference nucleic acid will be extended by a T, corresponding to the next native base immediately 5' to the region of hybridization. Here, the T and C nucleotides provided are distinguishably labeled, e.g., with detection moieties sufficiently different in mass to permit separation of the probes by MALDI-TOF. In the illustrated embodiment, ddTTP and ddCTP are used, preventing incorporation of further nucleotides. Measuring and comparing the amounts of the ddT-extended probe with that of the ddC-extended probe permits a comparison of the amount of amplified product of reference nucleic acid to the amount of amplified product of the its competitive template (Step 107 of FIG. 1).

Any other technique for mass labeling probes known in the art and/or described herein can also be used, e.g., the extension method used in solid-phase minisequencing. Hultman et al. 1988, Nucl. Acid. Res., 17: 4937-4946; Syvanen et al., 1990, Genomics, 8: 684-692. See also other methods provided in Ding and Cantor, (2004) A high-throughput gene expression analysis technique using competitive PCR and matrix-assisted lase desorption ionization time-of-flight MS. Proc Natl Acad Sci, 100: 3059-3064; and/or U.S. Application Publication 2004/0081993.

For example, pairs of probes extended in FIGS. 4a-4d can be separated by mass using MALDI-TOF.

The invention further contemplates situations where there are more than two alleles for a given region of a nucleic acid. In such embodiments, additional relations comparing amplified products of target nucleic acid corresponding to these additional alleles to amplified products of competitive template for the target nucleic acid can be determined, and compared to each other and/or to reference nucleic acid relations.

In some embodiments, another one of the nucleic acids amplified can serve as a second reference nucleic acid. In such embodiments, assessing the amount of target nucleic acid corresponding to a given allele can comprise obtaining a relation that compares amplified product of this second reference nucleic acid to amplified product of competitive template for the second reference nucleic acid; and comparing it to the first and/or second relations described above. Also, in some embodiments, data calculated using a first reference nucleic acid can be re-calculated relative to that of another reference nucleic acid.

In some embodiments, using two or more reference nucleic acids can provide an understanding of inter-specimen and/or inter-sample variation among the reference nucleic acids. In some embodiments, for example, β-actin and GAPD can be used as first and second reference nucleic acids. For example, there is a significant correlation between the ratio of β-actin/GAPD expression and cell size (Willey, J. C., Crawford, E. L., and Jackson, C. M. (1998) Expression measurement of many genes simultaneously by quantitative RT-PCR using standardized mixtures of competitive templates. *Am. J. Respir. Cell Mol. Biol.* 19, 6-17), which may make use of these 2 reference nucleic acids preferred in some embodiments. In some embodiments, any assessed nucleic acid or combination of nucleic acids, including all assessed nucleic acids, can be used as a reference. The number of genes that must be quantitated for normalization to any of the nucleic acids measured to result in adequate normalization may vary depending on the samples being studied.

In still some embodiments, a competitive template for each of the alleles may be used. FIG. 5, e.g., schematically illustrates assessing allele frequency of a breakpoint mutation in some embodiments. In the illustrated embodiment, two shortened competitive templates are used, one that co-amplifies with the normal allele (where no breakpoint mutation has occurred) and one that co-amplifies with the breakpoint allele. As used herein, "breakpoint" and "breakpoint lesion" are used interchangeably.

Suitable competitive templates for the normal allele and the breakpoint allele may be designed as follows. For the normal allele, a shortened competitive template can be prepared containing the normal allele sequence, but stopping short of the breakpoint locus. For the breakpoint allele, a shortened competitive template can be prepared that includes at least a part of the breakpoint locus. The competitive template for the target nucleic acid corresponding to the breakpoint allele can have two breakpoints relative to the target nucleic acid corresponding to the normal allele, e.g., one the occurred naturally and one introduced to make the shortened competitive template.

One of skill in the art will recognize various approaches for designing primers that amplify target nucleic acid corresponding to the normal allele and its competitive template but that do not amplify target nucleic acid corresponding to the breakpoint allele nor its competitive template; as well as primers that amplify target nucleic acid corresponding to the breakpoint allele and its competitive template but that do not amplify target nucleic acid corresponding to the normal allele nor its competitive template. In one approach, primers for amplifying target nucleic acid corresponding to the normal allele and its competitive template comprise a pair that span the same locus of the breakpoint and continue into the normal sequence not represented in the breakpoint allele; while primers for amplifying target nucleic acid corresponding to the breakpoint allele and its competitive template comprise a pair that span the locus of the breakpoint. For example, the primer pair for the normal allele (and its competitive template) can span the same locus of the breakpoint lesion on the sense 5' end and continue into the normal sequence at least about 30, at least about 40, at least about 50, at least about 60, and/or no more than about 80, no more than about 100, no more than about 120, no more than about 130, or no more than about 150 base pairs into the normal sequence not represented in the breakpoint lesion allele. In some embodiments, the primer pair for the breakpoint allele (and its competitive template) can span the locus of the breakpoint lesion to produce amplified product of at least about 100, at least about 120, at least about 130, at least about 150, at least about 200, and/or no more than about 250, no more than about 300, no more than about 350, or no more than about 400 base pairs.

Those of skill in the art will recognize additional suitable approaches for designing primers and competitive templates, based on the teachings and examples provided herein. The competitive templates, e.g., the competitive templates for the target nucleic acid corresponding to the alleles and for the reference nucleic acid(s), can be provided as a standardized mixture of reagents, as provided herein, e.g., where the competitive templates are at known concentrations relative to each other. In certain embodiments, reference nucleic acid in a sample to be assessed can be calibrated with the amount of its competitive template in a standardized mixture, again as elaborated herein. A PCR master mixture can be prepared (containing balanced amount of reference nucleic acid), the nucleic acids can each be co-amplified with their corresponding competitive templates, again as described herein, and aliquots of amplified products can be applied to an array.

Amplified products can be immobilized using a common capture moiety, e.g., where a common capture moiety anchors amplified product of the target nucleic acid corresponding to the normal allele and amplified product of its competitive template, and/or amplified product of the target nucleic acid corresponding to the breakpoint allele and amplified product of its competitive template. In the illustrated embodiment, an oligonucleotide is used comprising a 70-mer sequence complementary to a region shared by the anti-sense strand of the amplified product of the target nucleic acid corresponding to both alleles and of amplified products of both corresponding competitive templates; The olignucleotide is anchored to a support along its length and can be localized at two or more positions on a slide surface.

Products obtained from co-amplifying target nucleic acid corresponding to the normal allele with its corresponding competitive template and/or target nucleic acid corresponding to the breakpoint allele and its corresponding competitive template may be applied to the array, e.g., at the positions of the capture moieties, under conditions facilitating hybridization. After washing to remove un-hybridized products, the immobilized amplified products can be distinguished using fluorescent probes as detection moieties, again followed by hybridization and washing.

Figure 5A:
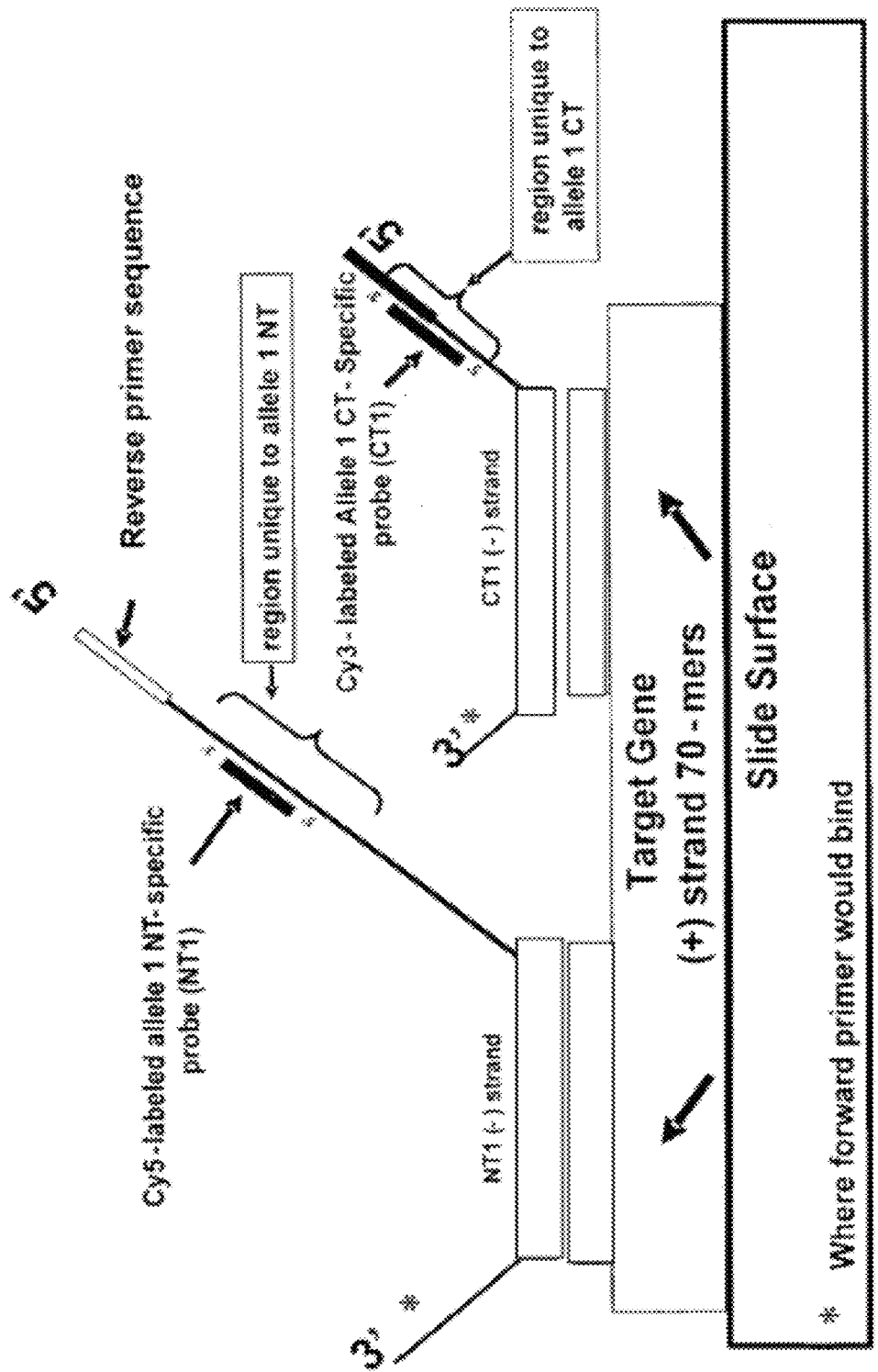
FIG. 5a-b illustrates assessing allele frequency of a breakpoint mutation in some embodiments.

FIG. 5a illustrates a position where amplified products are immobilized and distinguished using an allele 1 specific probe (NT1) and an allele 1 competitive template specific probe (CT1). In the illustrated embodiment, e.g., NT1 comprises a Cy5-labeled sense oligonucleotide complementary to an antisense sequence in the amplified product of target nucleic acid corresponding to the normal allele, but not present amplified product corresponding to in the breakpoint allele, nor either competitive template. CT1 comprises a Cy3-labeled sense oligonucleotide complementary to an antisense sequence in the amplified product of the competitive template for the normal allele target nucleic acid, but not present in amplified products of target nucleic acid corresponding to the normal allele, breakpoint allele nor competitive template for the breakpoint allele.

Measuring and comparing the fluorescence due to Cy5 (NT1) with that due to Cy3 (CT1) permits a comparison of the amount of amplified product of target nucleic acid corresponding to the normal allele to the amount of amplified product of its competitive template. In preferred embodiments, none or substantially none of CT1 and/or NT1 binds amplified product of target nucleic acid corresponding to the breakpoint allele or its competitive template, and/or no or substantially no amplified products of target nucleic acid corresponding to the breakpoint allele or of its competitive template contribute to the fluorescent measurements at this position.

Figure 5B:
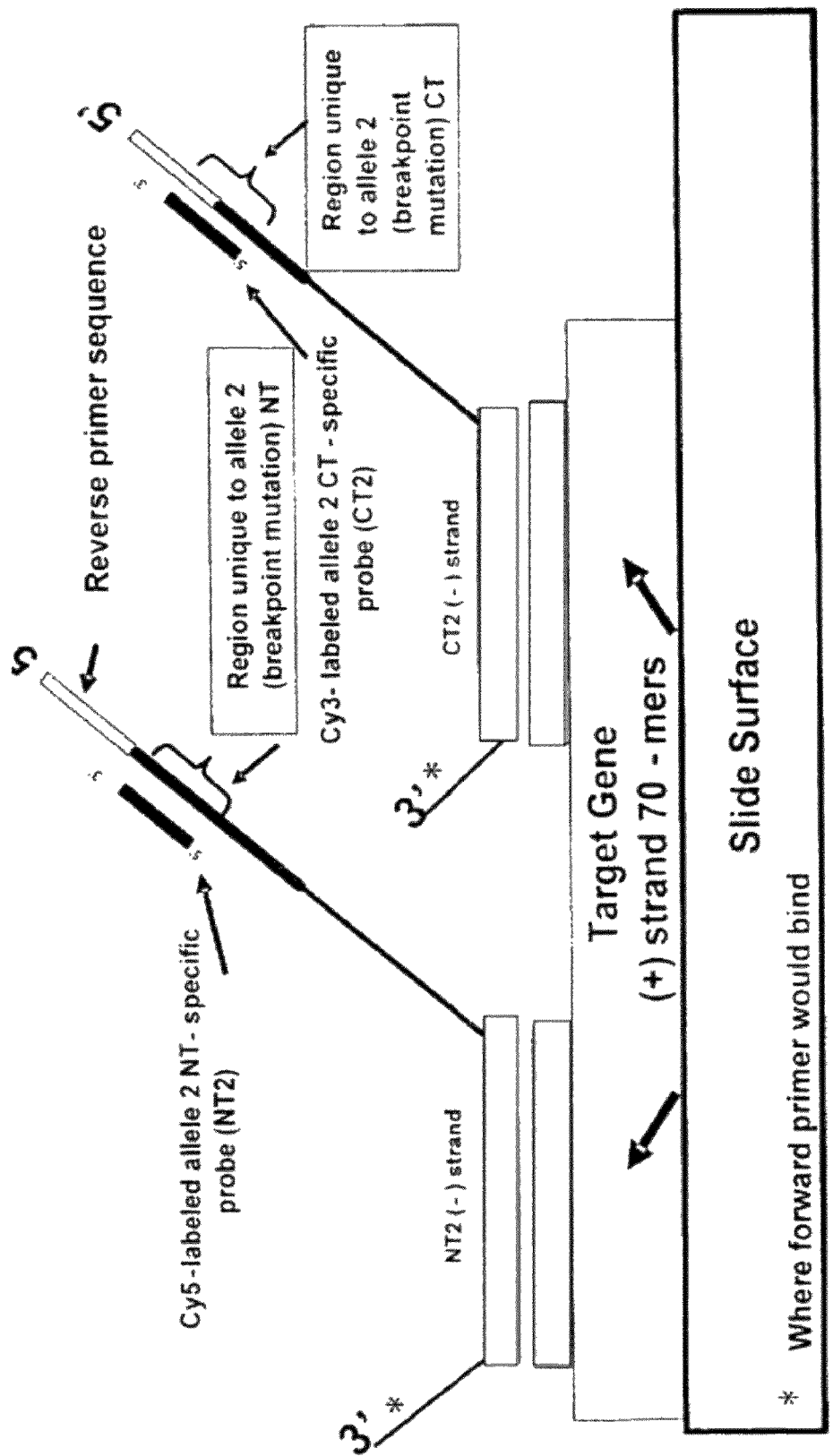

FIG. 5b illustrates a different position where amplified products are immobilized and distinguished using an allele 2 specific probe (NT2) and an allele 2 competitive template specific probe (CT2). In the illustrated embodiment, e.g., NT2 comprises a Cy5-labeled sense oligonucleotide complementary to an antisense sequence in the amplified product of target nucleic acid corresponding to the breakpoint allele, but not present in amplified product corresponding to the normal allele nor either competitive template. CT2 comprises a Cy3-labeled sense oligonucleotide complementary to an antisense sequence in the amplified product of the competitive template for the breakpoint allele target nucleic acid, but not present in amplified product of target nucleic acid corresponding to the normal allele, breakpoint allele nor competitive template for the normal allele.

Measuring and comparing the fluorescence due to Cy5 (NT2) with that due to Cy3 (CT2) permits a comparison of the amount of amplified product of target nucleic acid corresponding to the breakpoint lesion allele to the amount of amplified product of its competitive template. In preferred embodiments, none or substantially none of CT2 and/or NT2 binds amplified product of target nucleic acid corresponding to the normal allele or its competitive template, and/or no or substantially no amplified products of target nucleic acid corresponding to the normal allele or of its competitive template contribute to the fluorescent measurements at this position.

In preferred embodiments, amplified product of a reference nucleic acid and amplified product of its competitive template are also assessed, e.g., to allow normalization of the breakpoint and normal alleles. Measurement of reference nucleic acid and its competitive template can be carried out as in FIG. 3d, FIG. 4d, or as otherwise provided herein. Example II illustrates additional details for assessing nucleic acids using arrays described herein.

Based on the teachings and examples provided herein, one of skill in the art will appreciate that the instant methods can be used with different types of alleles. For example, the approach provided in FIGS. 3 and 4 can be used to assess breakpoint mutations, while that provided in FIG. 5 can be used to assess SNPs.

B. Use of Positive and Negative Controls

Another aspect of the instant invention relates to the use of controls, e.g., to detect false positive and/or false negatives. A positive control for a sample nucleic acid, as used herein, can refer to a nucleic acid having the same or substantially the same sequence as the sample nucleic acid. In preferred embodiments, the positive control has the identical sequence as the nucleic acid for which it serves as a control. In some embodiments, a known amount of the positive control can be subjected to identical or substantially identical conditions as the sample nucleic acid to detect false positives and/or false negatives for various alleles of target nucleic acid, e.g., as described below. Identical conditions include conditions approximating the conditions to which the sample target nucleic acid is subject, within experimental error. Use of positive controls can control for variation in hybridization (e.g., between the target nucleic acid and its competitive template), variation in detection moieties (e.g., Cy3 vs. Cy5 labels), variation in detection moieties from one lot to another, and the like.

A positive control can be prepared by any techniques known in the art and/or disclosed herein. Generally, the positive control will comprise a cloned, artificially-synthesized nucleic acid, but isolated, naturally-occurring nucleic acids may also be used where appropriate. For example, a sequence comprising an allele to be assessed can be isolated, amplified, quantified and/or cloned. In other embodiments, a sequence corresponding to that of an uncommon allele can be obtained by cloning the more common allele and introducing specific base pair alteration(s) as that those found in the less common allele, e.g., by site directed mutagenesis. In other embodiments, a positive control of an allele can be synthesized de vovo. Other techniques as known in the art can also be used.

In some embodiments, positive controls for more than one allele can be represented in a nucleic acid construct. For example, a nucleic acid can be prepared that comprises sequences representing more than one allele of a target nucleic acid, so that the expected alleles are represented co-linearly with one another. For example, additional bases can be introduced near the position of a reverse primer for a first allele, where the additional bases provide a sequence representing a second allele. In such embodiments, the construct provides each positive control of the expected alleles in a 1:1 ratio, preferably in a fixed 1:1 ratio. In some embodiments, a number of allelic sequences can be introduced colinearly, e.g., in a plasmid or other nucleic acid construct. For example, sequences corresponding to a number of mutations responsible and/or associated with a given biological state, e.g., a given disease state, can be assembled on a given plasmid. An example includes the 10 to 20 mutations responsible and/or associated with cystic fibrosis.

Such constructs can be used in certain embodiments of the instant invention, including, e.g., for detecting false negatives, e.g., as described herein. For example, the construct can be amplified with competitive templates for one or more of the different allelic variations, amplified product can be applied at different positions of an array, and probes for one or more of the different allelic variations added at one or more of the different positions. In preferred embodiments, a positive control is provided for each allele being assessed.

Figure 6:
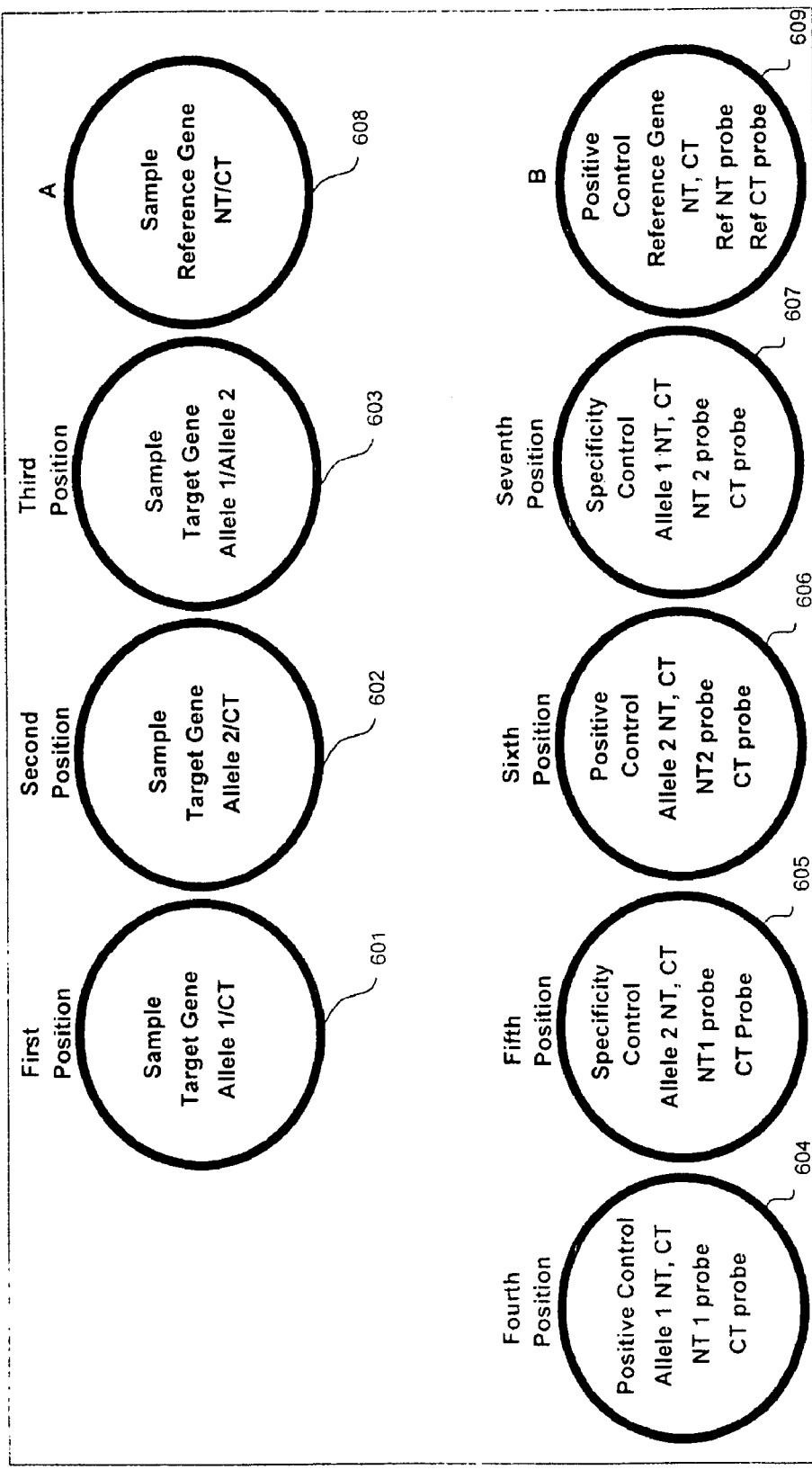
FIG. 6 illustrates detecting false negatives and false positives of target nucleic acid in some embodiments of the instant invention.

FIG. 6 illustrates detecting false negatives and false positives of target nucleic acid in some embodiments of the instant invention. The amplified products assessed correspond to those discussed in FIG. 3. Common capture moieties for amplified products corresponding to the target nucleic acid are localized at first 601, second 602, and third positions 603 on an array, corresponding to first, second and third positions discussed in reference to FIGS. 3a, 3b, and 3c. As FIG. 6 illustrates, the same common capture moieties can be localized at additional positions, e.g., fourth 604, fifth 605, sixth 606 and seventh 607 positions. The common capture moieties for amplified products of the reference nucleic acid and its competitive template can also be localized at one or more other positions, e.g. at position A 608, corresponding to the position discussed in FIG. 3d, and position B 609, discussed below.

First through third positions 601-603 and position A 608 correspond to amplified products obtained from a sample, e.g., a sample comprising target nucleic acid in various allelic forms and at least one reference nucleic acid. As discussed above, products obtained by co-amplifying target nucleic acid and its competitive template are immobilized at the first, second and third positions (601-603) and products obtained by co-amplifying reference nucleic acid and its competitive template are immobilized at another position, position A 608.

Fourth through seventh positions 604-607 and position B 609 correspond to amplified controls. False positive and/or false negatives for first and second alleles can be detected by repeating the experiments performed on the sample using the positive controls of each allele, and determining analogous relations. For example, in some embodiments, false negatives and/or false positives for the first allele and/or the second allele can be detected by co-amplifying a known amount of a positive control for the first allele and a known amount of competitive template for the target nucleic acid and/or a known amount of a positive control for the second allele and a known amount of competitive template for the target nucleic acid; immobilizing co-amplified products using the same capture moiety as used in experiments with the target nucleic acid; and obtaining analogous relations of amplified products, as described in more detail below.

FIG. 6 illustrates a fourth position 604 where false negatives of the first allele are detected. Amplified products of positive control for the first allele and competitive template for the target nucleic acid can be immobilized using the same common capture moieties those used at positions 601-603 (FIG. 3a-3c). The same detection moieties used at position 601 (FIG. 3a) can be added, and a relation analogous to the first relation obtained. For example, a fourth relation can be obtained, where the fourth relation compares amplified product of the positive control for the first allele that is detectable by the allele 1 specific probe to amplified product of the competitive template for the target nucleic acid (e.g., that is detectable by the competitive template specific probe).

FIG. 6 illustrates a fifth position 605 where false positives of the first allele are detected. Amplified products of positive control for the second allele and competitive template for the target nucleic acid can be immobilized using the same common capture moieties as those used at positions 601-603 (FIG. 3a-3c). The same detection moieties used at the first position 601 (FIG. 3a) can be added, and an analogous relation obtained. For example, a fifth relation can be obtained, where the fifth relation compares amplified product of the positive control for the second allele that is detectable by the allele 1 specific probe to amplified product of the competitive template for the target nucleic acid (e.g., that is detectable by the competitive template specific probe). This serves as a specificity control for the allele 1 specific probe.

FIG. 6 illustrates a sixth position 606 where false negatives of the second allele are detected. Amplified products of positive control for the second allele and competitive template for the target nucleic acid can be immobilized using the same common capture moieties those used at positions 601-603 (FIG. 3a-3c). The same detection moieties used at position 602 (FIG. 3b) can be added, and a relation analogous to the second relation obtained. For example, a sixth relation can be obtained, where the sixth relation compares amplified product of the positive control for the second allele that is detectable by the allele 2 specific probe to amplified product of the competitive template for the target nucleic acid (e.g., that is detectable by the competitive template specific probe).

FIG. 6 illustrates a seventh position 607 where false positives of the second allele are detected. Amplified products of positive control for the first allele and competitive template for the target nucleic acid can be immobilized using the same common capture moieties as those used at positions 601-603 (FIG. 3a-3c). The same detection moieties used at the second position 602 (FIG. 3b) can be added, and an analogous relation obtained. For example, a seventh relation can be obtained, where the seventh relation compares amplified product of the positive control for the first allele that is detectable by the allele 2 specific probe to amplified product of the competitive template for the target nucleic acid (e.g., that is detectable by the competitive template specific probe). This serves as a specificity control for the allele 2 specific probe.

In more preferred embodiments, experimental conditions used are the same or substantially the same as those used in assessing allele frequency of the target nucleic acid. For example, the same or similar co-amplification technique and/or conditions are used; the same or similar polymerization-inducing agent is used; the same or similar amounts of co-amplified products are spotted onto the slide; the same or similar time intervals and conditions for hybridization are used; the same or similar washing methods are used; the same or similar amounts of probes are added; the same or similar conditions for hybridization and/or washing are used; and/or the same or similar techniques are used to measure Cy5 and/or Cy3 fluorescence. Others of skill in the art will recognize other experimental details that can be held constant, or substantially constant within acceptable experimental error, in obtaining the analogous relations with the controls. Further, where more than two allelic variations exists, additional positive controls can be used for the third, fourth, fifth, etc., alleles.

In some preferred embodiments, the positive control for a given allele is co-amplified with an equal or substantially equal amount of competitive template for the target nucleic acid. For example, the same (or substantially the same) number of molecules of the positive control and of the competitive template can be co-amplified. In such cases, Cy5 fluorescence would be expected to equal (or substantially equal) to that of Cy3 fluorescence at locations for detecting false negatives (604 and 606), e.g., providing about a 1:1 ratio. In other preferred embodiments, the amount of positive control to the amount of the competitive template to be co-amplified can be in a ratio of about 1:10 to about 10:1.

FIG. 6 also illustrates use of a positive control for the sample reference nucleic acid discussed in FIG. 3d. In some embodiments, false negatives and/or false positives for the reference nucleic acid can be detected, e.g., by co-amplifying a known amount of a positive control for the reference nucleic acid and a known amount of competitive template for the reference nucleic acid; immobilizing co-amplified products using the same capture moiety as used in experiments with the reference nucleic acid, and obtaining analogous relations of amplified products, as discussed below.

FIG. 6 illustrates position B 609 where false negatives of the sample reference nucleic acid are detected. Amplified products of positive control for the reference nucleic acid and its competitive template can be immobilized using the same common capture moieties as those used at position A 608 (FIG. 3d). The same detection moieties used at position 608 (FIG. 3d) can be added, and a relation analogous to the third relation obtained. For example, a relation can be obtained comparing amplified product of the positive control for the reference nucleic acid that is detectable by reference native template specific probe to amplified product of its competitive template that is detectable by the reference competitive template specific probe.

In preferred embodiments, methods provided herein can markedly reduce false negatives and/or false positives for a given allele. In more preferred embodiments, methods provided herein can reduce false negatives and/or false positives for a given allele to a statistically insignificant number. In even more preferred embodiments, methods provided herein can eliminate false negatives and/or false positives for a given allele. In some embodiments, quality control is facilitated by the presence of competitive template for each target nucleic acid being assessed and the simultaneous presence of a competitive template for a reference nucleic acid for each reaction (that can control for loading). For example, where a competitive template is used in a number of nucleic acid measurements, there may be no false negatives and a statistically insignificant number of false positives.

One of skill in the art will recognize various applications in which positive controls described herein can be used. For example, positive controls can be used in assessing breakpoint lesion allele frequency. Also, positive control can also be used for any target nucleic acid being assessed, whether or not it occurs in allelic variations.

Methods and arrays, such as those described above, can provide improved quality control in assessing SNPs and other allelic variations, e.g., in diagnostic applications. For example, the approaches described herein can provide standardized, numerical and/or reproducible nucleic acid measurements, including gene expression data. One of skill in the art will appreciate other arrays that can be designed to carry out the methods of the instant invention, in light of the disclosures provided herein, which are also contemplated within the scope of the instant invention.

D. Two-Step Approach

In some embodiments, the present invention provides a method of assessing a nucleic acid provided in a sample, comprising co-amplifying the nucleic acid, a number of other nucleic acid(s), a competitive template for the nucleic acid and a competitive template(s) for the other nucleic acid(s), e.g., to produce first amplified product thereof. In some embodiments, first amplified product can be diluted and then further co-amplified, e.g., to produce second amplified product thereof. Amplifying and then further amplifying nucleic acid and competitive template for the nucleic acid may be considered as two rounds of amplification and a process employing two rounds of amplification may be referred to as a "two-step" process or "two-step" approach.

Figure 7:
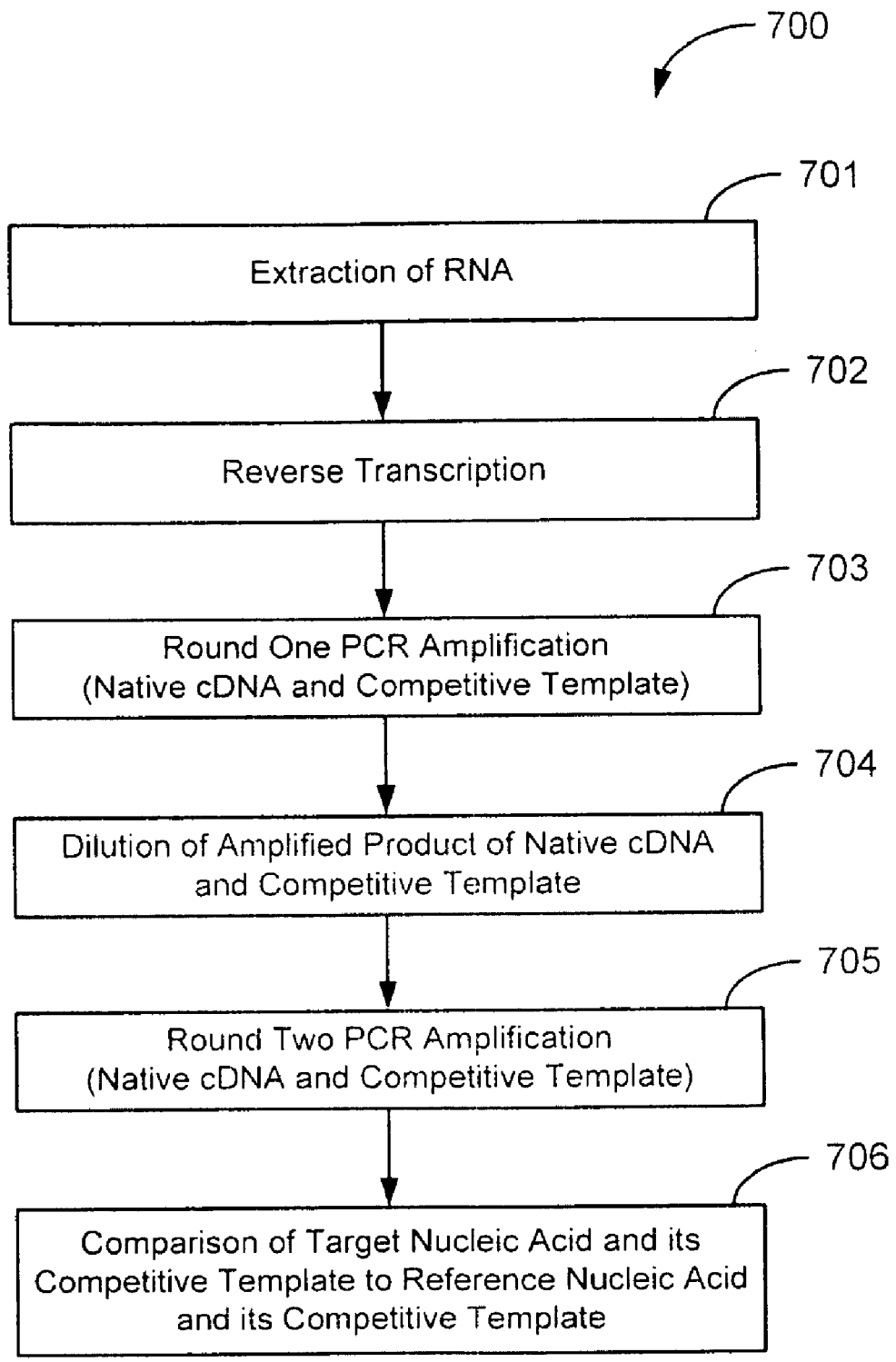
FIG. 7 illustrates an overall "two-step" process for evaluating nucleic acids in some embodiments.

FIG. 7 schematically illustrates some embodiments of the overall "two-step" process 700 described herein, e.g., where the amplified nucleic acid is cDNA.

At step 701 of FIG. 7, for example, RNA can be extracted from specimen cells or tissues. At step 702 of FIG. 7, extracted RNA can be reverse transcribed to provide cDNA. In some embodiments, the amplified nucleic acid is a nucleic acid other than cDNA, as described above. In some embodiments, although reverse transcription efficiency may be variable, the representation of one nucleic acid in comparison to another in the resultant cDNA product may not be affected. That is, in some embodiments, the amount of cDNA of target nucleic acid compared with the amount of cDNA of a second nucleic acid (e.g., a second nucleic acid serving as a reference nucleic acid) can remain equivalent or substantially equivalent to amount of mRNA of target nucleic acid compared with the amount of mRNA of the second nucleic acid.

At step 703 of FIG. 7, native cDNA and its competitive template are co-amplified in a first round of amplification. Native cDNA may comprise both the target nucleic acid and one or more other nucleic acids, which can be co-amplified with a competitive template for the target nucleic acid and a competitive template for one or more of the other nucleic acids. For example, the cDNA may be serially diluted and one or more serial dilutions then amplified.

In preferred embodiments, the competitive templates of at least two nucleic acids are at known concentrations relative to one another. For example, artificially shortened competitive templates may be generated according to the method described by Celi et al., Nucleic Acids Res. 21:1047 (1993).

In some embodiments, more than one nucleic acid (and its corresponding competitive template) can be co-amplified and preferably at least one of the other nucleic acids can serve as a reference nucleic acid, as outlined above. In some embodiments, a competitive template for a reference nucleic acid may comprise a nucleic acid having a sequence similar to either strand of cDNA of a housekeeping gene, but having a distinguishable feature as described above.

At step 704 of FIG. 7, amplified product of native cDNA and competitive template (obtained in round one) are diluted before further amplification in round two. In some embodiments, amplified product of target nucleic acid and its corresponding competitive template may be diluted. In some embodiments, amplified product of a reference nucleic acid and its corresponding competitive template may be diluted. Diluting amplified product may be achieved by any techniques known in the art and/or described herein. For example, diluting may involve removal of an aliquot of a mixture comprising first amplified product, and transfer to a vessel containing additional buffer. In some embodiments, diluting produces at least about a 1,000,000-fold dilution, at least about a 500,000-fold dilution, at least about a 100,000-fold dilution, at least about a 50,000-fold dilution, at least about a 10,000-fold dilution, at least about a 5,000-fold dilution, at least about a 1,000-fold dilution, at least about a 500-fold dilution, or at least about a 100-fold dilution.

At step 705 of FIG. 7, diluted amplified product of native cDNA and competitive template (obtained in round one) are further amplified in round two. In preferred embodiments, round-two amplification is carried out using at least some of the same primers as used in round one. In some embodiments, diluted amplified product of a target nucleic acid and its corresponding competitive template may be further co-amplified in a second round of amplification. In some embodiments, diluted amplified product of a reference nucleic acid and its corresponding competitive template may be further co-amplified in a second round of amplification. As mentioned above, the use of two rounds may be referred to as a "two-step" approach. In some embodiments, target nucleic acid and/or the reference nucleic acid can be subjected to more than two rounds of amplification. For example, second amplified product of the target nucleic acid and its corresponding competitive template may be again diluted and further amplified and/or second amplified product of the reference nucleic acid and its corresponding competitive template may be again diluted and further amplified.

Various nucleic acids and corresponding competitive templates may be amplified in a given vessel during round one and/or round two of a two-step process. For example, in some embodiments, more than one nucleic acid (each with its corresponding competitive template) are co-amplified in a given vessel. In some embodiment, repeat amplifications are carried out with fewer different nucleic acids (each with its corresponding competitive template) in a given vessel. For example, in some preferred embodiments, amplified products are further amplified with primers for a nucleic acid corresponding to one gene. For example, co-amplifying diluted first amplified product of a nucleic acid and of the competitive template for the nucleic acid can be achieved by using a primer pair for co-amplifying the particular nucleic acid and its corresponding competitive template dried onto the vessel used in round two. For example, primers for individual genes can be aliquotted into individual reaction vessels and dried down, e.g., on 384-well plates. Multiple plates loaded with primers (e.g., about 10, about 100, about 500 plates) can be prepared in advance. For example, in some embodiments, primers prepared this way are stable at 4° C. for months.

At step 706 of FIG. 7, amounts of amplified products can be compared. In some embodiments, the amount of amplified product of a target nucleic acid is compared to the amount of amplified product of its competitive template. In some embodiments, e.g., comparison involves obtaining a relation, e.g., a first relation reflecting the amplified amounts of target nucleic acid compared with the amplified amounts of its competitive template. In preferred embodiments, this relation is provided as a ratio, e.g., a first ratio of the amount of amplified product of a nucleic acid to the amount of amplified product of its competitive template, e.g., where the nucleic acid and its competitive template are co-amplified.

In some embodiments, the amount of amplified product of a target nucleic acid is compared to a reference nucleic acid. In preferred embodiments, the reference nucleic acid is itself compared to a competitive template for the reference nucleic acid. For example, in some embodiments, the amount of amplified product of a reference nucleic acid is compared to the amount of amplified product of its competitive template. In some embodiments, e.g., this comparison involves obtaining a relation, e.g., a second relation reflecting the amplified amount of reference nucleic acid compared with the amplified amount of its competitive template. In preferred embodiments, this relation is provided as a ratio, e.g., a second ratio of the amount of amplified product of reference nucleic acid to the amount of amplified product of its competitive template, e.g., where the reference nucleic acid and its competitive template are co-amplified.

In preferred embodiments, comparison of the target nucleic acid to a reference nucleic acid involves comparing the first and second relations described above. For example a relation reflecting how the first relation compares with the second relation can be obtained. In some embodiments, this relation compares the first ratio to the second ratio, e.g., as a ratio of the first and second ratios.

In a two-step process, amplified product obtained after the first or second (or higher) round for target nucleic acid (and its corresponding competitive template); and amplified product obtained after the first or second (or higher round) for reference nucleic acid (and its corresponding competitive template) may be used in the comparisons described above. For example, in preferred embodiments, a first relation is obtained comparing second amplified product of the target nucleic acid to second amplified product of the competitive template for the target nucleic acid; a second relation is obtained comparing first amplified product of reference nucleic acid to first amplified product of competitive template for the reference nucleic acid; and the first and second relations are compared. In more preferred embodiments, the relation obtained by comparing the first and second relations remains substantially constant beyond the exponential phase of amplification of the nucleic acid. Substantially constant can refer to variations of +/− about 1%, about 5, about 10%, about 15%, or about 20% of an absolute constant number.

As described above, in some embodiments, another one of the nucleic acids amplified can serve as a second reference nucleic acid. In such embodiments, measuring the amount of target nucleic acid can comprise obtaining a third relation that compares the first amplified product of this second reference nucleic acid to the first amplified product of competitive template for the second reference nucleic acid; and comparing the first and third relations. Also, in some embodiments, data calculated using a first reference nucleic acid can be re-calculated relative to that of another reference nucleic acid, again as described above.

As mentioned above, in some embodiments, a two-step method may comprise two step amplification of the nucleic acid serving as a reference nucleic acid. In some such embodiments, a fourth relation may be obtained comparing second amplified product of the reference nucleic acid to second amplified product of its competitive template. In some embodiments, the first and fourth relations are compared, e.g., by obtaining a ratio of the first and fourth ratios. In still some embodiments, where the nucleic acid serving as a reference nucleic acid is amplified in two rounds, first amplified product of the target nucleic and first amplified product of its competitive template can be used to obtain the first relation, e.g., the first ratio.

Where the "two-step" approach is extended for more than two rounds of amplification, second amplified product of a nucleic acid and of a competitive template for the nucleic acid can be diluted and still further amplified, e.g., to produce third amplified product thereof. The steps of diluting and further amplifying may be repeated at least about once, at least about twice, at least about 3 times, at least about 5 times, at least about 10 times, at least about 20 times, at least about 50 times, at least about 100 or more. In preferred embodiments, repeated amplifications are carried out using at least some of the same primers as used in one or more earlier rounds.

In some embodiments, comparing the first and second and/or first and third and/or first and fourth relations can provide a "ratio of ratios" corresponding to a numerical value. In some embodiments, numerical values for various measured nucleic acids, e.g., for various gene expression measurements, are provided as a database, as described in more detail below. For example, such a database can be used with gene expression data in clinical diagnostic testing.

In some embodiments, obtaining the comparisons, e.g., the first, second, third and/or fourth ratios, involves measuring the amounts of amplified product of each of the nucleic acid, the competitive template for nucleic acid, the reference nucleic acid(s) and the competitive template(s) for the reference nucleic acid. Any method capable of quantifying nucleic acids having a distinguishable feature (e.g., having different sizes and/or sequences) can be used, as described above.

In some embodiments, arrays for use in the practice of the present invention comprise oligonucleotides immobilized on a solid support where a first set of the immobilized oligonucleotides can bind to a sequence of the amplified product of the nucleic acid that is not common to the amplified product of the competitive template for the nucleic acid and where a second set of the immobilized oligonucleotides can bind to a sequence of the amplified product of the competitive template of the nucleic acid that is not common to the amplified product of the nucleic acid, for example, sequences that span the juncture between the 5' end of the competitive template and the truncated, mis-aligned 3' end of the competitive template (e.g., that can be prepared according to the method of Celi). Amplified product of the nucleic acid and of the competitive template for the nucleic acid can be allowed to bind to the array and a ratio obtained from the two sets. In still some embodiments, the two-step approach can be practiced without the use of solid phase hybridizations, e.g., without the use of arrays.

In some embodiments, a two-step approach can be used in assessing allelic variation and/or allelic frequency. For example, co-amplified products of the target nucleic acid (corresponding to both alleles) and of the competitive template for the target nucleic acid can be diluted, and the diluted products can be further co-amplified, preferably using at least some of the same primers used during the first round of amplification. Relations for assessing allelic frequency can be obtained comparing second amplified products of target nucleic acid corresponding to a first allele and/or second amplified products of target nucleic acid corresponding to a second allele to second amplified product of the competitive template for the target nucleic acids. In some embodiments, relations for assessing allelic frequency can be normalized using relations comparing second amplified product of a reference nucleic acid to second amplified product of its competitive template. Third, fourth, fifth, etc., steps of dilution and rounds of amplification can also be used, in some embodiments.

The use of two rounds in preferred embodiments of a two-step process can lower the threshold amount of nucleic acid that can be measured in a sample. The lower threshold of detection can be defined as the minimum amount of analyte that can be reliably detected above background. The detection limit can be defined as the lowest concentration or quantity of analyte that can be detected with reasonable certainty. Without being limited to a particular hypothesis and/or theory, there may be a minimum amount of cDNA that can be used to achieve a statistically significant measurement. Lower threshold of detection in gene expression measurements may be considered in terms the minimal number of molecules of cDNA in a reaction for amplification or the minimal number of cells.

Figure 8:
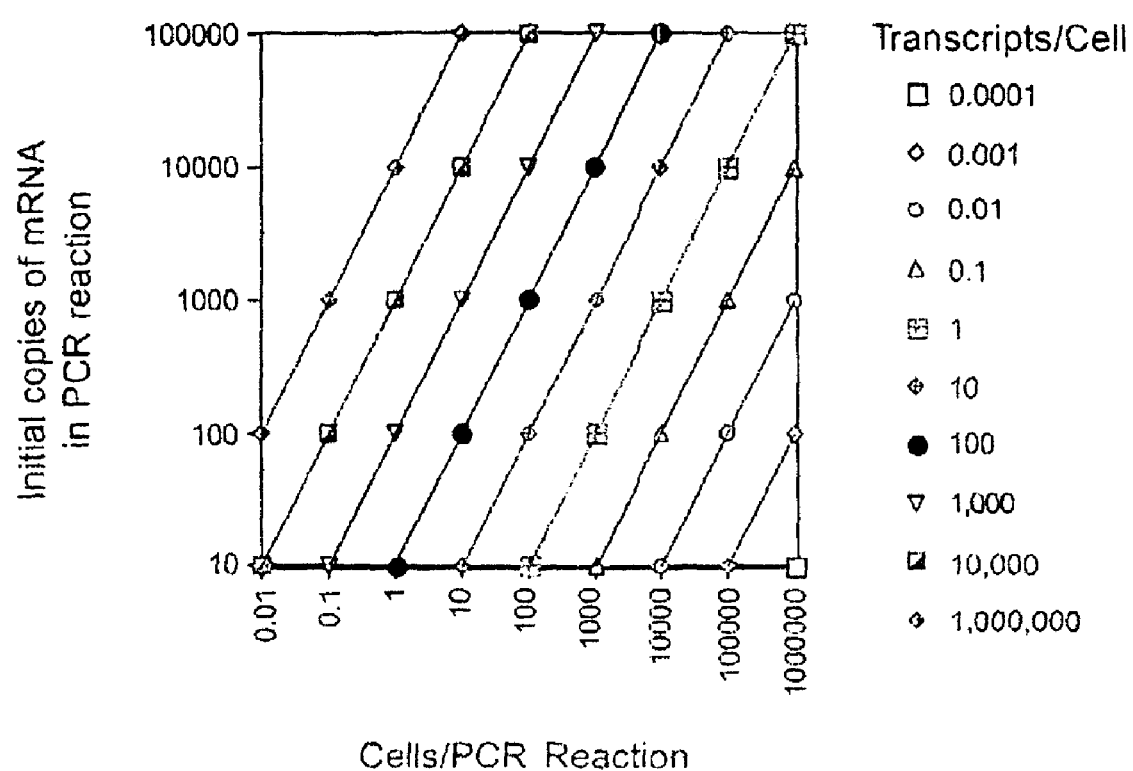
FIG. 8 illustrates a relationship between the amount of nucleic acid used in a PCR reaction and the number of copies of mRNA transcripts/cell that can be measured for a given number of cells/PCR reaction.

FIG. 8 schematically illustrates how the amount of cDNA used in a PCR reaction has a direct relationship to the number of copies of mRNA transcripts/cell that can be measured for a given number of cells used. The minimal number of cells then depends on mRNA copies/cell in a sample, as well as the efficiency of RNA extraction and/or reverse transcription. For example, consider the number of cells to provide RNA sufficient to result in at least 10 molecules of cDNA for a particular gene. It generally is assumed that RNA extraction is close to about 100% whereas reverse transcription is about 10% efficient. Thus, if a homogeneous population of cells is studied and each cell contains 10 copies of mRNA for a gene, 1 copy per cell will remain after reverse transcription. Due to stoichiometric considerations, cDNA samples included in a PCR reaction that contain less than about 10 molecules of a transcript is questionable, in some types of PCR. In such embodiments, cDNA representing about 10 cells is preferably present in the PCR reaction, as illustrated in FIG. 8. If a heterogeneous cell population is studied in which 1 cell out of 10 expresses a particular transcript, cDNA representing about 1,000 cells is preferably present in the PCR reaction.

In certain embodiments, the use of two rounds can overcome some of the limitations illustrated in FIG. 8. Consider a typical about 10 µl cDNA sample representing about 1,000 cells and comprising about $6 \times 10^5$ molecules of β-actin nucleic acid. Genes expressed at the mean level (100-fold lower than β-actin), are represented by about 6,000 molecules in the sample. A number of genes that may be important functionally are expressed 10,000-fold lower than β-actin, and for such genes there would be about 60 molecules represented in the sample. In a 100-fold smaller sample of about 100 nanoliters, genes expressed 10,000-fold lower than β-actin would be represented by about 0.6 copies or fewer.

In certain embodiments of the instant invention, about 10 nanoliters of an about 10 µl round one amplified product may be used in a round two reaction volume of about 100 nanoliters. Because more than about 1,000,000-fold amplification is routinely achieved in the round one reaction, about 10 nanoliters of the about 10 µl round one reaction will contain ample amplified product of nucleic acid and competitive template to be measured with statistical confidence after round two. Similar reasoning applies to the number of copies of a rare allele that can be measured, e.g., where the nucleic acid being measured is genomic rather than cDNA.

Further, in some preferred embodiments, the use of two rounds can increase the number of measurements obtainable from a small sample of nucleic acid. For example, in some embodiments, at least about 10,000, at least about 50,000, at least at about 80,000, at least about 100,000, at least about 150,000 nucleic acid measurements can be obtained from the same amount of starting nucleic acid typically used to obtain one measurement using the processes provided in Willey and Willey et al. '390, '606, and '978. In some embodiments, at least about 200,000, at least about 500,000, at least at about 800,000, at least about 1,000,000, or at least about 1,500,000 nucleic acid measurements can be obtained from the same amount of starting nucleic acid typically used to obtain one measurement using the processes provided in Willey and Willey et al. '390, '606, and '978, preferably without loss of sensitivity to detect rare transcripts. For example, in some embodiments, sufficient amplified product can be generated to measure nucleic acids corresponding to several genes in about 100 to about 1,000 cell samples. Using the processes provided in Willey and Willey et al. '390, '606, and '978, cDNA representing about 100 to about 1,000 cells is typically used to measure one nucleic acid in one PCR reaction. Referring again to FIG. 5, using this amount allows detection of transcripts that are expressed at about 0.1 to about 1 copy per cell (or about 1 to about 10 copies per 10 cells) with statistical significance. The same amount of cDNA can be used in a first round of amplification in certain embodiments of the instant invention. Since this cDNA is co-amplified with a competitive template for the nucleic acid to be measured, and since the relationship of endogenous cDNA to its competitive template remains constant or substantially constant, amplified product from round one can be diluted and further amplified in a second round with primers specific to a given nucleic acid without significantly changing the relative amounts of amplified product.

Further, in some embodiments, use of two rounds can increase the number of nucleic acid that can be measured in a given sample. Some embodiments, for example, allow replicate measurement of many genes in small amounts of specimen material. In some embodiments, multiple PCR amplification can be done on the same sample for various allelic forms of a gene of interest.

E. Use of a Standardized Mixture

In some embodiments, assessing a nucleic acid and/or allelic frequency in a sample can comprise use of a standardized mixture. "Standardized mixture" as used herein can refer to a mixture comprising a number of internal standards, e.g., a number of competitive templates, at known concentrations. In preferred embodiments, the standardized mixture comprises a competitive template for at least one target nucleic acid and a competitive template for at least one reference nucleic acid in a sample, where the competitive templates are at known concentrations relative to each other. In more preferred embodiments, the competitive templates are at fixed concentrations relative to each other, up to and including all other, competitive templates in the mixture.

Figure 9:
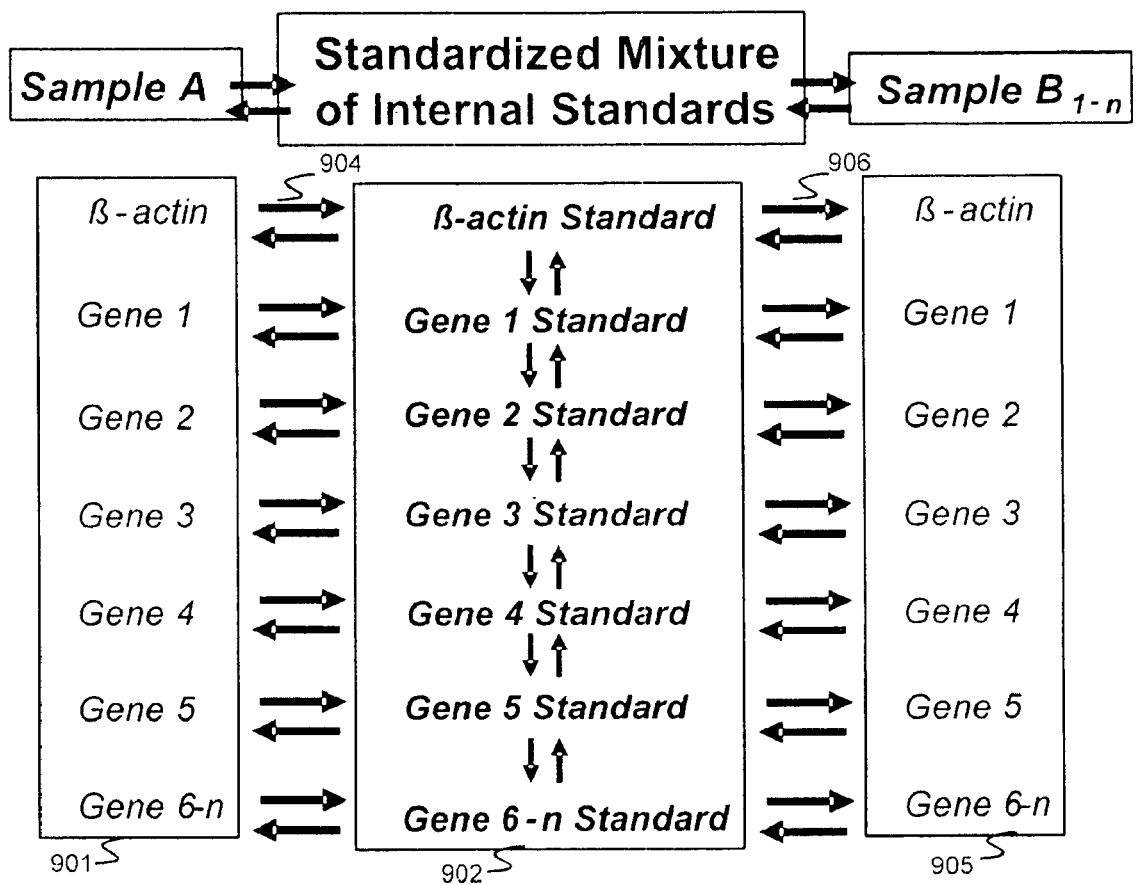
FIG. 9 illustrates a standardized mixture used in some embodiments of the present invention.

FIG. 9 illustrates a standardized mixture used in some embodiments of the present invention. Feature 901 illustrates a sample, Sample A, which comprises a number of nucleic acids to be measured, corresponding to Genes 1-6-n, as well as a nucleic acid to serve as a reference, corresponding to β-actin in this illustration.

Feature 902 illustrates a standardized mixture of internal standards comprising competitive templates for the reference nucleic acid (β-actin standard) as well as competitive templates for target nucleic acids (Genes 1 to 6-n standards). In some embodiments, the number of competitive template(s) can be at least one other competitive template in addition to a target nucleic acid, at least about 100, at least about 200, at least about 500, at least about 1,000, at least about 5,000, at least about 10,000, at least about 50,000, or at least about 100,000 other competitive templates. For example, competitive templates for several genes to be measured can be included in a given standardized mixture, as illustrated in feature 902.

Feature 903 (vertical two-way arrows) illustrates a relationship among internal standards within a standardized mixture. A competitive template for each of a number of genes can be at a fixed concentration relative to other competitive templates within a standardized mixture. Accordingly, in some embodiments, when a genomic or cDNA sample is combined with a standardized mixture, the concentration of each competitive template is fixed relative to the genomic or cDNA representing its corresponding gene.

Feature 904 (horizontal two-way arrows) illustrates a relationship between an internal standard and its corresponding genomic or cDNA from a sample and how each target nucleic acid is measured relative to its respective competitive template in the standardized mixture. Because the competitive template for each of these nucleic acids is present at a fixed concentration relative to other competitive templates, the standardized mixture can allow a target nucleic acid to be assessed relative other nucleic acids being measured with the standardized mixture 902. For example, Sample A 901 can be combined with standardized mixture 902, e.g., to form a master mixture used for further co-amplifications. For example, the master mixture can be used in co-amplifying nucleic acid corresponding to Gene 1 and its competitive template (Gene 1 standard), as well as co-amplifying nucleic acid corresponding to Gene 2 and its competitive template (Gene 2 standard).

In a two-step approach using standardized mixture 902, a target nucleic acid and its respective competitive template can be co-amplified to produce first amplified product thereof. The amplified products can be diluted and further co-amplified one or more times, as described in more detail above. In some embodiments, first amplified product of the reference nucleic acid can be diluted and further amplified one or more times, also as described above.

In some embodiments, a standardized mixture can be used in assessing allelic variation and/or allelic frequency. For example, Gene 1 of feature 901 can occur in two (or more) allelic variations, each of which can be co-amplified with the competitive template for Gene 1 (Gene 1 standard). In some embodiments, the competitive templates can comprise shorted competitive templates, as described in more detail above. Some embodiments of the invention provide kits comprising standardized mixtures of such competitive templates, as provided in more detail below.

For example, some embodiments of the instant invention provide methods for assessing allele frequency of a first allele and a second allele of a target nucleic acid in a sample comprising providing a standardized mixture comprising a competitive template for the target nucleic acid and a competitive template for a reference nucleic acid present in the sample, where the competitive templates are at known concentrations relative to each other. The sample can be combined with the standardized mixture and target and reference nucleic acids co-amplified with their corresponding competitive templates, as provided herein.

In other embodiments, competitive templates can be provided for the different allelic forms, e.g., where Gene 1 corresponds to a first allele and Gene 2 corresponds to a second allele of a given target nucleic acid, and each is co-amplified with its corresponding competitive template (Gene 1 and Gene 2 standards). Some embodiments of the invention provide kits comprising standardized mixtures of such competitive templates, as provided in more detail below.

Feature 905 illustrates a number of other samples, Samples $B_{1-n}$ 905, which also comprise nucleic acids, corresponding to Genes 1 to 6-n, and a reference nucleic acid, corresponding to β-actin. In some embodiments, the number of β-actin mRNA molecules obtained from a cell may vary from about 100 to about 1000, e.g., depending on efficiency of RNA extraction, the size and/or other characteristics of the cell.

In some embodiments, another nucleic acid can serve as a second reference nucleic acid. For example, in some embodiments, gene expression measured in reference to β-actin mRNA can be re-calculated relative to that of another reference nucleic acid, if so desired. For example, if another nucleic acid, e.g. GAPDH or any other of Genes 1 to 6-n 902, appears to vary less than β-actin across the samples $B_{1-n}$ 905, the data may be re-calculated ("normalized") to that reference without altering the relative expression measurement, e.g., the relative expression measurement within a sample. In some embodiments assessing allelic frequency, a gene known to be present in only two copies in the genome and that has no known pseudogenes may be used as the reference, as discussed above. When nucleic acid measurement data are re-calculated, the relative measured amounts among nucleic acids can remain the same or substantially the same, as discussed below.

Feature 906 (horizontal two way arrows) illustrates how each of these nucleic acids in additional samples can be measured relative to its respective competitive template in the standardized mixture 902. As with Sample A 901, each of these nucleic acids can be assessed relative other nucleic acids measured with the standardized mixture 902. Further, it is possible to compare data from analysis of Sample A 901 to data from analysis of samples $B_{1-n}$ 904. For example, because the number of molecules for each competitive template is known within the standardized mixture, it is possible to calculate all data in the form of molecules/reference nucleic acid molecules.

In some embodiments, the standardized mixture 902 comprises sufficient amounts of competitive templates for assessing one or more of the target nucleic acids in a large number of samples $B_{1-n}$ 904, e.g., in more than about $10^4$ samples, in more than about $10^5$ samples, in more than about $10^6$ samples, in more than about $10^7$ samples, in more than about $10^8$ samples; in more than about $10^9$ samples, in more than about $10^{10}$ samples, in more than about $10^{11}$ samples, in more than about $10^{12}$ samples, in more than about $10^{13}$ samples, in more than about $10^{14}$ samples, or in more than about $10^{15}$ samples. In some preferred embodiments, use of a common standardized mixture for multiple samples can reduce time to obtain nucleic acid measurements. For example, re-preparing reagents for PCR reactions can be time consuming and can also lead to sources of error.

A nucleic acid and its competitive template may be co-amplified (and/or further co-amplified) in the same or different vessels as one or more other nucleic acid and corresponding competitive template. See, e.g., Apostolakos, M. J., Schuermann, W. H., Frampton, M. W., Utell, M. J., and Willey, J. C. (1993) Measurement of gene expression by multiplex competitive polymerase chain reaction. *Anal. Biochem.* 213, 277-284; Willey, J. C., Crawford, E. L., and Jackson, C. M. (1998) Expression measurement of many genes simultaneously by quantitative RT-PCR using standardized mixtures of competitive templates. *Am. J. Respir. Cell Mol. Biol.* 19, 6-17. In some preferred embodiments, use of a standardized mixture 902 allows different nucleic acids amplified in separate vessels to be directly compared. In some embodiments, for example, one nucleic acid and its competitive template are co-amplified in one vessel, while another nucleic acid and its competitive template are co-amplified in a different vessel. In either case, as feature 903 illustrates, nucleic acid can be measured relative to its respective internal standard competitive template within the standardized mixture and the other nucleic acid can serve as a reference nucleic acid. That is, in preferred embodiments, the use of a standardized mixture allows the concentration of internal standard for a nucleic acid relative to others to remain fixed across different measurements.

As feature 903 illustrates, use of a common standardized mixture allows direct comparisons to be made among Samples $B_{1-n}$ 904. The different samples may be amplified at different times, e.g., on different days; in the same or different experiments in the same laboratory; and/or in different experiments in different laboratories. Crawford, E. L., Peters, G. J., Noordhuis, P., et al. (2001) Reproducible gene expression measurement among multiple laboratories obtained in a blinded study using standardized RT (StaRT)-PCR. *Mol. Diagn.* 6, 217-225; Crawford, E. L., Warner, K. A., Khuder, S. A., et al. (2002) Multiplex standardized RT-PCR for expression analysis of many genes in small samples. *Biochem, Biophys. Res. Commun.* 293, 509-516; Crawford, E. L., Khuder, S. A., Durham, S. J., et al. (2000) Normal bronchial epithelial cell expression of glutathione transferase P1, glutathione transferase M3, and glutathione peroxidase is low in subjects with bronchogenic carcinoma. *Cancer Res.* 60, 1609-1618; DeMuth, J. P., Jackson, C. M., Weaver, D. A., et al. (1998) The gene expression index c-myc×E2F1/p21 is highly predictive of malignant phenotype in human bronchial epithelial cells. *Am. J. Respir. Cell. Mol. Biol.* 19, 18-24; Mollerup, S., Ryberg, D., Hewer, A., Phillips, D. H., and Haugen, A. (1999) Sex differences in lung CYP1A1 expression and DNA adduct levels among lung cancer patients. *Cancer Res.* 59, 3317-3320; Rots, M. G., Willey, J. C., Jansen, G., et al. (2000) mRNA expression levels of methotrexate resistance-related proteins in childhood leukemia as determined by a standardized competitive template-based RT-PCR method. *Leukemia* 14, 2166-2175; Rots, M. G., Pieters, R., Peters, G. J., et al. (1999) Circumvention of methotrexate resistance in childhood leukemia subtypes by rationally designed antifolates. *Blood* 94, 3121-3128; Allen, J. T., Knight, R. A., Bloor, C. A., and Spiteri, M. A. (1999) Enhanced insulin-like growth factor binding protein-related protein 2 (connective tissue growth factor) expression in patients with idiopathic pulmonary fibrosis and pulmonary sarcoidosis. *Am. J. Respir. Cell. Mol. Biol.* 21, 693-700; Loitsch, S. M., Kippenberger, S., Dauletbaev, N., Wagner, T. O., and Bargon, J. (1999) Reverse transcription-competitive multiplex PCR improves quantification of mRNA in clinical samples-application to the low abundance CFTR mRNA. *Clin. Chem.* 45, 619-624; Vondracek, M. T., Weaver, D. A., Sarang, Z., et al. (2002) Transcript profiling of enzymes involved in detoxification of xenobiotics and reactive oxygen in human normal and Simian virus 40 T antigen-immortalized oral keratinocytes. *In. J. Cancer* 99, 776-782. In preferred embodiments, measurements are made using the same standardized mixture and dilution of internal standard competitive templates.

Further, in some embodiments, measurements obtained using various quantifying approaches are directly comparable where a common standardized mixture is used. For example, statistically similar results were obtained using a common standardized mixture and quantifying amplified product by various types of electrophoresis, or by either a Caliper AMS 90 SE30 electrophoretic separation or by hybridizing them to microarrays in accordance with some embodiments of the instant invention. In another example, reproducible gene expression measurements were obtained when amplified product was quantitated using MALDI-TOF MS instead of using electrophoresis. Ding C. and Cantor, C. R. (2003) A high-throughput gene expression analysis technique using competitive PCR and matrix-assisted laser desorption ionization time-of-flight MS. *Proc. Natl. Acad. Sci. USA* 100, 3059-3064.

The use of the standardized mixtures may also be applied to other methods for measuring nucleic acids, e.g., in real-time RT-PCR. For example, in some embodiments, obtaining a ratio of amplified product of a nucleic acid to amplified product of a competitive template for the nucleic acid can comprise a use of real-time RT-PCR analyses. As another example, a standardized mixture may be used in accordance with some embodiments of the instant invention in combination with competitive template techniques described, e.g., in Siebert, P. D., et al., Nature 359:557-558 (1992); Siebert, P. D., et al., BioTechniques 14:244-249 (1993), and Clontech Brochure, 1993, Reverse Transcriptase-PCR (RT-PCR). For example, fluorescent probes for using a standardized mixture with real-time RT-PCR may be developed.

Figure 10:
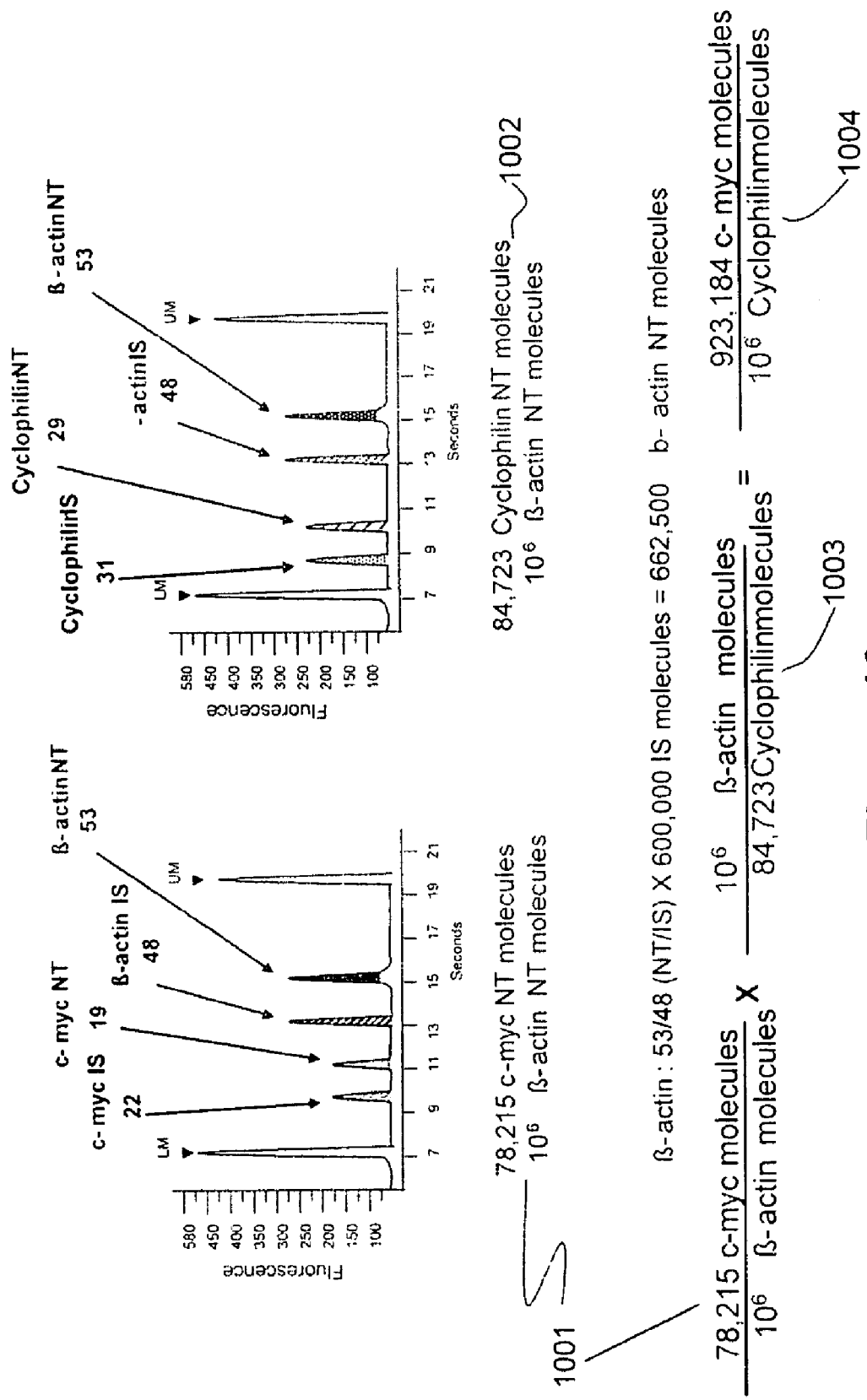
FIG. 10 illustrates re-calculating numerical values based on a first reference nucleic acid (β-acting) to numerical values based on a second reference nucleic acid (cyclophilin).

FIG. 10 illustrates a re-calculation using cyclophilin as a second reference gene, where gene expression is provided as a ratio of (target gene NT molecules)/($10^6$ β-actin NT molecules). In FIG. 10, NT refers to native template, and the target gene is c-myc.

Ratio 1001 illustrates a gene expression value for the target gene as the ratio of (c-myc NT molecules)/($10^6$ β-actin NT molecules). Ratio 1002 illustrates a gene expression value for a first reference gene as the ratio of (cyclophilin NT molecules)/($10^6$ β-actin NT molecules). Ratio 1003 illustrates a conversion factor for re-calculating relative to cyclophilin. Ratio 1003 provides the inverse of ratio 1002, namely of ($10^6$ β-actin NT molecules)/(cyclophilin NT molecules). Conversion can be achieved by multiplying ratio 1001 by the ratio 1003 to provide ratio 1004. Ratio 1004 illustrates the ratio (c-myc NT molecules)/(cyclophilin NT molecules), a gene expression value for the target gene relative to the new reference gene.

In other embodiments, conversion from (molecules of target nucleic acid)/(molecules of a first reference nucleic acid) to (molecules of target nucleic acid)/(molecules of a second reference nucleic acid) can be achieved, e.g., by inverting a gene expression value of the second reference, e.g., to (molecules of first reference nucleic acid)/(molecules of second reference gene) and multiplying this factor by the data. The value for molecules of the first reference nucleic acid can cancel out, leaving the second reference gene in the denominator.

Re-calculation may be accomplished using a spreadsheet, in some embodiments. In some cases, re-calculating relative to a new reference can alter the numerical value of a measured amount of a given nucleic acid without altering the numerical values of nucleic acids relative to each other. Without being limited to a particular hypothesis and/or theory, this may be explained in that measured amounts of a nucleic acid can be said to be linked through use of a common standardized mixture of competitive templates 902. Thus, the ratio between two nucleic acids within a sample would be the same or substantially the same using β-actin, cyclophilin, or a combination of nucleic acids as the reference nucleic acid.

F. Use of Serially-Diluted Standardized Mixtures

In some embodiments, a series of serially-diluted standardized mixtures is used to assess amounts of nucleic acid. "Serially-diluted standardized mixtures" can refer to two or more standardized mixtures in which one or more of the reagents in the standardized mixtures is serially-diluted. In some embodiments, one or more reagents in the standardized mixtures is serially-diluted relative to a different one or more of the reagents in the mixtures. For example, in preferred embodiments, a competitive template for a first nucleic acid is serially diluted relative to a competitive template for a second nucleic acid where the second nucleic acid can act as a reference nucleic acid. In some embodiments, the reference nucleic acid can be present at two different concentrations in two of the serially-diluted standardized mixtures. One of a series of serially-diluted mixtures is also referred to herein as a "Mix."

Figure 11:
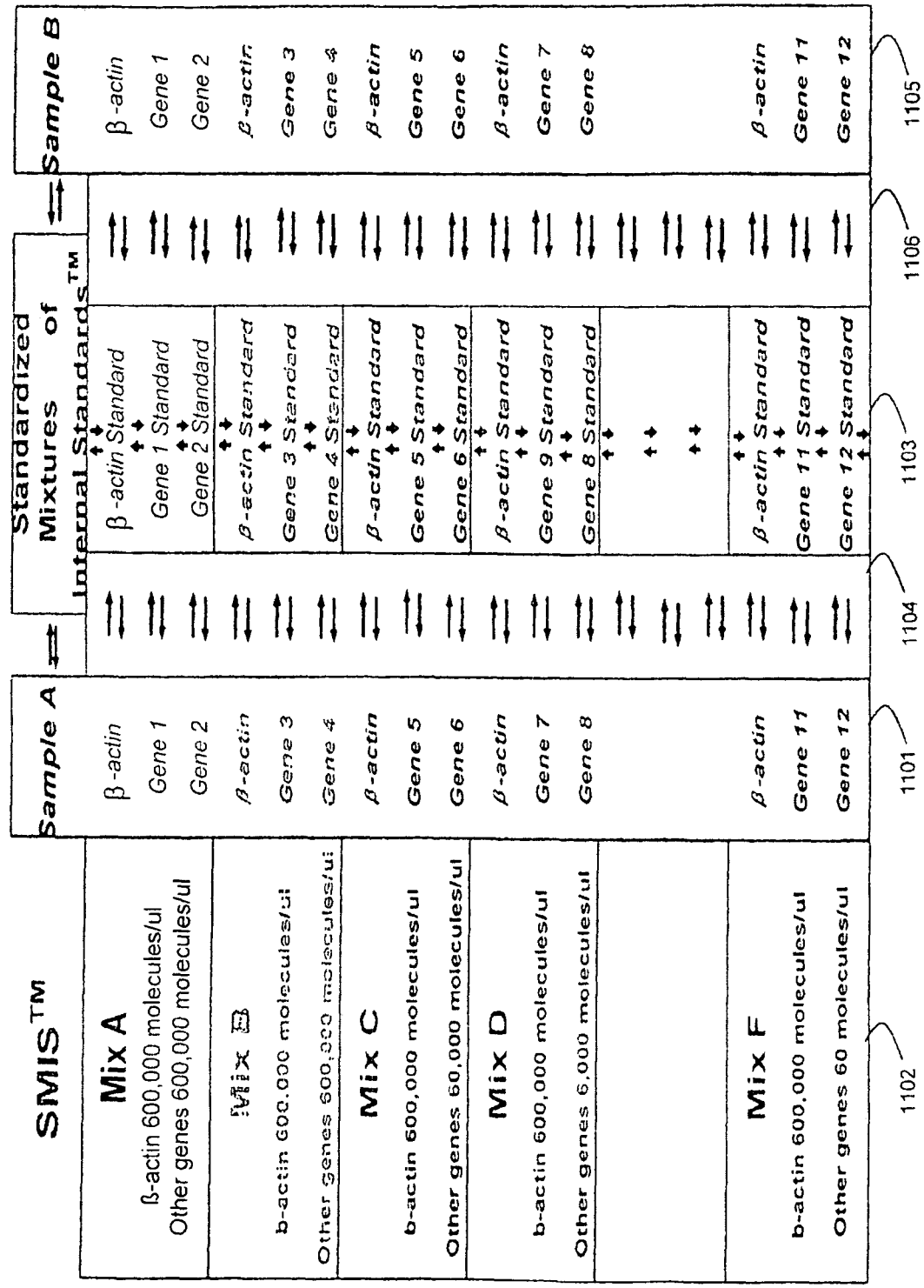
FIG. 11 illustrates use of a series of standardized mixtures, according to some embodiments of the instant invention.

FIG. 11 illustrates the use of a series of standardized mixtures, according to some embodiments of the instant invention. In the figure, "SMIS" refers to a standardized mixture of internal standards, prepared in accordance with embodiments of the instant invention.

Feature 1101 illustrates a sample, Sample A, which comprises a number of nucleic acids to be measured, corresponding to Genes 1-12, as well as a nucleic acid that serves as a reference, corresponding to β-actin in this illustration.

Feature 1102 illustrates a series of six standardized mixtures, Mixes A-F, comprising 10-fold dilutions of competitive templates for different genes relative to competitive templates for a reference gene, β-actin in this illustration.

Feature 1103 illustrates the relationship between competitive templates for the reference nucleic acid (β-actin standard) compared to competitive templates for target nucleic acids (Genes 1 to 12 standards) in the different serially-diluted mixtures. Use of the series can allow measurement of the nucleic acids corresponding to different genes expressed over a range, e.g., a range of more than six orders of magnitude. The series can also allow measurement of alleles that occur in low frequency, e.g. rare alleles, present in only a few genomes of individuals in a population.

Feature 1104 (horizontal two way arrows) illustrates how these different nucleic acids in the Sample 1101 are in balance with (i.e., calibrated to) different concentrations of their corresponding competitive templates in the different mixes. "Balancing" or being in balance with, as used herein, can refer to calibrating amounts of two nucleic acids. For example, Genes 9 and 10 in Sample A 1101, expressed at a low level, are in balance with Mix E comprising 600 molecules/ul of competitive template for gene 9 and Gene 10. Genes 9 and 10 are preferably measured using Mix E. Genes 6 and 7 are expressed at a higher level in Sample A 1101 and are in balance with Mix C and Mix D, respectively. Gene 6 is preferably measured using Mix C and Gene 7 is preferably measured using Mix D.

In some embodiments, use of a series allows measurement of nucleic acids over a range of concentrations, including, e.g., alleles that occur at low frequency. Where practice of the invention assesses gene expression, as in FIG. 11, some embodiments allow measurement over one or more orders of magnitude of gene expression. For example, in some embodiments, the amounts of two nucleic acids to be measured vary over a range of less than about one order of magnitude, more than about one order of magnitude, or more than about 2 orders of magnitude. In some embodiments, the amounts of two different nucleic acids to be measured, e.g., mRNA levels expressed from two or more different genes, vary over a range of about 3 or more orders of magnitude, about 4 or more orders of magnitude, about 5 or more orders of magnitude, about 6 or more orders of magnitude, or about 7 or more orders of magnitude, e.g., spanning an about 7-log range of gene expression including about $10^{-3}$ about $10^{-2}$, about 0.1, about 1, about 10, about $10^2$, about $10^3$, and about $10^4$ copies/cell. In some embodiments, the amounts of two different nucleic acids to be measured vary over a range of about 8 or more, about 9 or more, or about 10 or more orders of magnitude, e.g., spanning an about 10-log range of gene expression of about $10^{-3}$, about $10^{-2}$, about 0.1, about 1, about 10, about $10^2$, about $10^3$, about $10^4$, about $10^5$, or about $10^6$ copies/cell. Such ranges of gene expression may be important in detecting agents of biological warfare and/or pathogenic agents, e.g., certain viruses, and the like, that may be present in very small concentrations in a sample.

Feature 1105 illustrates a different sample, Sample B, also comprising nucleic acids corresponding to Genes 1-12 and to β-actin.

Feature 1106 (horizontal two way arrows) illustrates how the different nucleic acids in the Sample B 1105 are also in balance with different concentrations of their corresponding competitive templates in the different mixes. A given gene in a different sample can be in balance with the same Mix, allowing past experience with measuring a given gene to inform the selection of an appropriate Mix. For example, genes expressed in the range of about $10^1$ to about $10^4$ molecules/$10^6$ β-actin molecules may be measured using Mixes C, D, E, and/or F. Genes expressed in the range of about $10^4$ to about $10^7$ molecules/$10^6$ β-actin molecules may be measured using Mixes A, B, C, and/or D. One of skill in the art will appreciate that where quantitative data is obtainable using two or more mixes, replicate data can be obtained.

In some embodiments, the series can comprise serial 10-fold dilution from a standardized mixture comprising competitive template for more or less than the 12 genes of FIG. 11. For example, a series can be prepared for a 96-nucleic acid standardized mixture or a standardized mixture comprising various numbers of nucleic acids as detailed above.

In some embodiments, the method for assessing an amount of a nucleic acid involves providing a series of serially-diluted standardized mixtures comprising a competitive template for the nucleic acid and a competitive template for another nucleic acid present in a number of samples comprising the nucleic acid, where the competitive templates are at known concentrations relative to each other; combining one of the samples comprising the nucleic acid with one of the serially-diluted standardized mixtures; co-amplifying the nucleic acid and its competitive template to produce amplified product thereof; obtaining a first relationship that compares amplified product of the nucleic acid to amplified product of its competitive template; determining whether the relationship corresponds to a ratio within about 1:10 to about 10:1; and if not, repeating combining, co-amplifying, obtaining and determining steps using a second one of the serially-diluted standardized mixtures. Further, in some embodiments, the other nucleic acid and its competitive template can be co-amplified to produce amplified product thereof; a second relationship obtained that compares amplified product of the other nucleic acid to its competitive template; and comparing first and second relationships.

In some embodiments, a "two-step" approach may be used. For example, in some embodiments, the method further comprises diluting amplified product of nucleic acid and its corresponding competitive template; and further co-amplifying the diluted amplified product to produce further amplified product thereof.

In some embodiments, a series of standardize mixtures can be used in assessing allelic variation and/or allele frequency. For example, Gene 1 of feature 1101 can occur in two (or more) allelic variations, each of which can be co-amplified with the competitive template for Gene 1 (Gene 1 standard). In some embodiments, the competitive templates can comprise shortened competitive templates, as described in more detail above. Some embodiments of the invention provide compositions and kits comprising standardized mixtures of such competitive templates.

For example, some embodiments of the instant invention provide methods for assessing allele frequency of a first allele and a second allele of a target nucleic acid in a sample comprising providing a series of serially-diluted standardized mixtures comprising a competitive template for the target nucleic acid and a competitive template for a reference nucleic acid present in a number of samples comprising the target nucleic acid, where the competitive templates are at known concentrations relative to each other; combining one of the samples comprising the target nucleic acid with one of the serially-diluted standardized mixtures; co-amplifying the target nucleic acid (corresponding to both alleles) and the competitive template for the target nucleic acid to produce amplified product thereof; obtaining a first relationship that compares amplified product of either allele of the target nucleic acid to amplified product of the competitive template for the target nucleic acid; determining whether the relationship corresponds to a ratio within about 1:10 to about 10:1; and if not, repeating combining, co-amplifying, obtaining and determining steps using a second one of the serially-diluted standardized mixtures. Further, in some embodiments, the reference nucleic acid and its competitive template can be co-amplified to produce amplified product thereof; a second relationship obtained that compares amplified product of the reference nucleic acid to its competitive template; and comparing first and second relationships.

In other embodiments, competitive templates can be provided for the different allelic forms, e.g., where Gene 1 correspond to a first allele and Gene 2 corresponds to a second allele, and each can be co-amplified with its corresponding competitive template (Gene 1 and Gene 2 standards). Some embodiments of the invention provide compositions and kits comprising standardized mixtures of such competitive templates.

In some embodiments, different concentrations of competitive templates for reference nucleic acid may be used. For example, where the expression of a first reference nucleic acid varies in comparison to a second reference nucleic acid, use of more than one concentration can be helpful in determining inter-sample and/or inter-specimen variation in expression of corresponding reference genes. For example, some embodiments use two different concentrations of GAPD competitive templates, as the expression of GAPD relative to β-actin may vary as much as about a 100-fold from one tissue type to another. Having two different concentrations of GAPD competitive template relative to that for β-actin, can enable better comparison of GAPD to β-actin in various samples.

Figure 12:
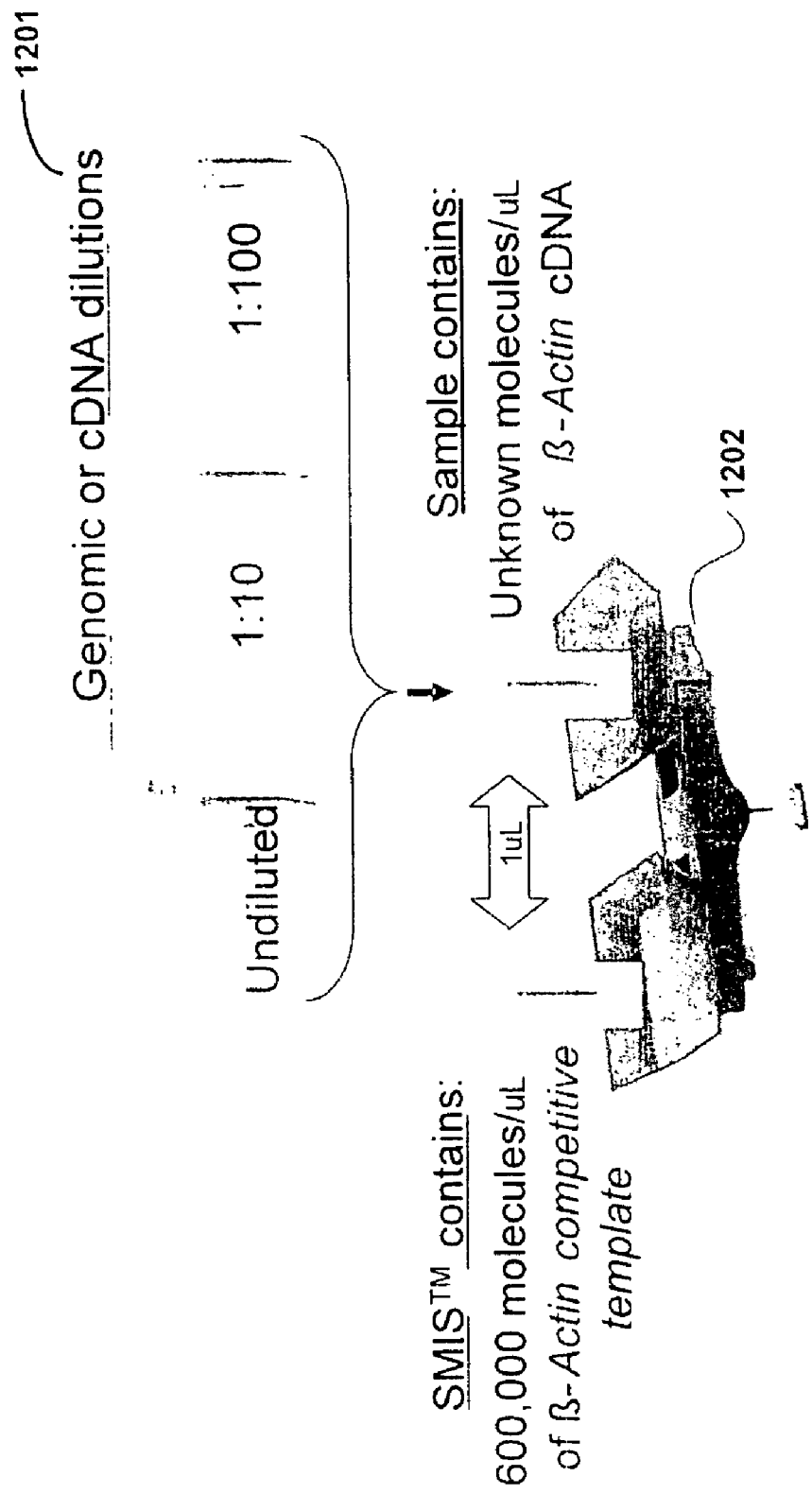
FIG. 12 illustrates using a nucleic acid serving as a reference to balance a sample with a standardized mixture of a series of serially-diluted standardized mixtures.

FIG. 12 illustrates how, in some embodiments, nucleic acid serving as a reference can be used to balance a sample with a standardized mixture of the series of serially-diluted standardized mixtures.

Step 1201 illustrates quantitative balancing of a nucleic acid sample. Qualitative balancing, as used herein, can also be referred to as qualitative calibration. The nucleic acid sample can be diluted to provide a series of serially-diluted samples and one of the series selected, for combining with standardized mixture, depending on the concentration of the reference nucleic acid in the dilution. For example, at step 901, genomic or cDNA material is serially-diluted to provide a series of samples having serial dilutions of β-actin nucleic acid.

Step 1202 illustrates that a dilution is selected to provide about equivalent β-actin native template (NT) molecules (genomic or cDNA) as there are β-actin competitive template (CT) molecules in a standardized mixture. In some embodiments, a specimen can be diluted until any one (or more) of the nucleic acids is approximately balanced with, i.e., approximately calibrated to, the amount of competitive template for that nucleic acid in the standardize mixture. Thus, in preferred embodiments, the first one of the number of samples to be combined with standardized mixture is selected to provide reference nucleic acid calibrated or approximately calibrated to its competitive template in the standardized mixture. Approximate calibration can occur when the nucleic acid is within about a 10-fold range, a 9-fold range, an 8-fold range, a 7-fold range, a 6-fold range, a 5-fold range, a 4-fold range, a 3-fold range, a 2-fold range, or a 1-fold range or less, of the concentration of the competitive template for that particular nucleic acid in the standardized mixture. In preferred embodiments, the NT/CT ratio for the reference nucleic acid is between about 1:10 and about 10:1 (e.g., for measurement to be within linear dynamic range).

Figure 13:
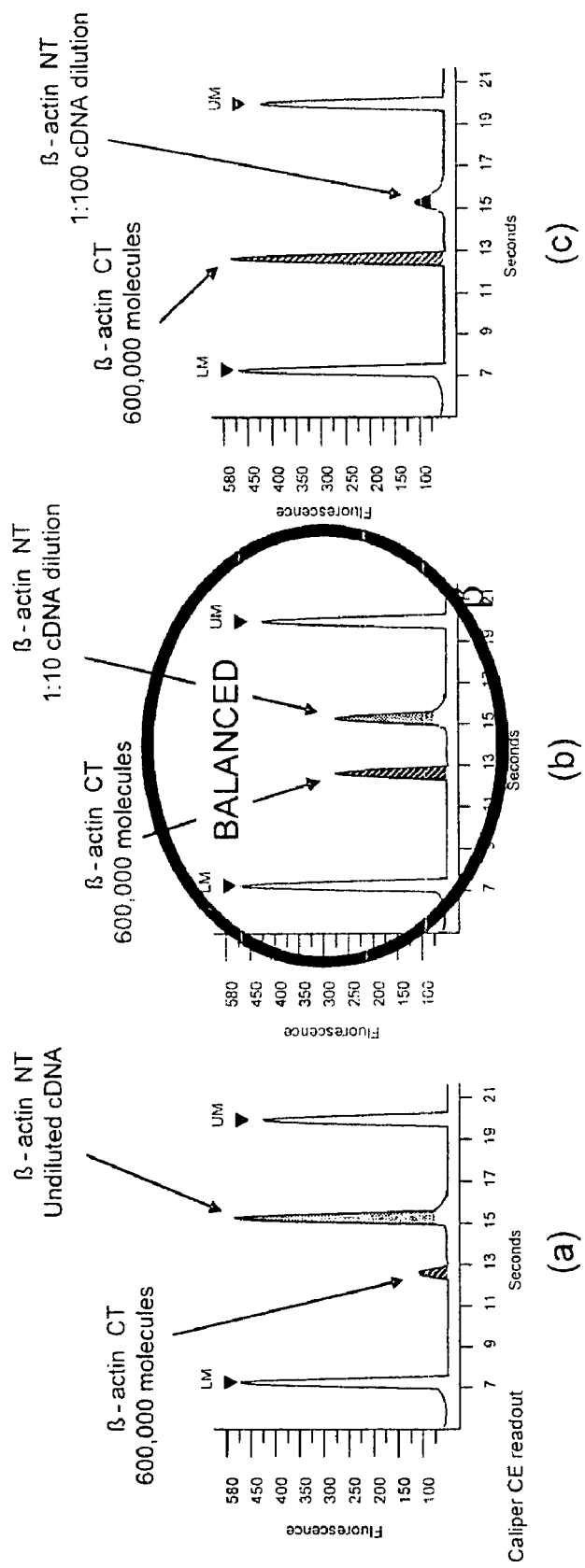
FIG. 13 illustrates a cDNA dilution that provides a reference nucleic acid (β-actin) in balance with 600,000 molecules of the reference nucleic acid competitive template in a standardized mixture.

FIG. 13 further illustrates selection of a cDNA dilution that provides a reference nucleic acid (β-actin in this illustration) in balance with 600,000 molecules of the reference nucleic acid competitive template in the standardized mixture, e.g., so the nucleic acid can compete equally (or substantially equally) with the 600,000 competitive template molecules. In FIG. 13a, undiluted sample is used. The undiluted sample containing β-actin nucleic acid is mixed with a standardized mixture containing 600,000 molecules of β-actin competitive template and co-amplified. Much more amplified product from the sample β-actin than the competitive template. In FIG. 13b, the sample is diluted 10 fold before it is mixed with the standardized mixture and co-amplified with its competitive template. Using this dilution, approximately equal amounts of amplified products are obtained. Accordingly, β-actin nucleic acid in the 1:10 dilution is said to be balanced with the 600,000 of its competitive template molecules in the standardized mixture. In FIG. 13c, sample is diluted 100 fold and produces much less amplified products than its competitive template.

In preferred embodiments, all standardized mixtures in a given series contain a given number of molecules of a particular reference nucleic acid, allowing any of the standardized mixtures to be used in balancing. For example, A-F can each contain about $10^{-12}$ M β-actin competitive template so than any of Mixes A-F can be used in balancing with a cDNA sample. Typically, Mix F is used for balancing β-actin cDNA in a sample.

FIG. 14 illustrates a series of serially-diluted standardized mixtures comprising one or more mixes where 1 μL contains 600,000 molecules of β-actin competitive template, corresponding to 1 μL of a standardized mixture containing $10^{-12}$ M β-actin competitive template. In that case, for example, cDNA material can be diluted until 1 μL is calibrated to 600,000 molecules of β-actin competitive template. Typically, this is the amount of cDNA derived from 100 to 1,000 cells in the case of β-actin. Although the number of β-actin mRNA copies/cell varies from one cell to another, using a conservative estimate of 600 β-actin mRNA copies/cell and assuming a reverse transcription efficiency of 10%, a cDNA sample containing 600,000 molecules of β-actin cDNA can be derived from 1,000 cells.

This amount may be used to provide sufficient cDNA to quantify genes expressed at low levels, e.g., genes expressed in low copy number, e.g., at about 0.1 copy/cell, 0.05 copies/cell, and/or 0.01 copies/cell. With reference cDNA in balance with about $10^{-12}$ M β-actin in the PCR reaction, some embodiments can quantify sample nucleic acid that is in balance with about $10^{-16}$ M or less of its CT. In some specific embodiments, where reference cDNA is in balance with about $10^{-2}$ M β-actin in a 10 μl PCR reaction volume, there can be about 600,000 molecules of β-actin NT and about 600,000 molecules of β-actin CT in the reaction, and the number of molecules of sample nucleic acid in balance with about $10^{-16}$ M or about $10^{-17}$ M of its CT can be about 60 or about 6 respectively. About 60 or about 6 molecules of nucleic acid can translate into about 0.1 to about 0.01 molecules/cell.

This balancing can provide at least about 10 copies present at the beginning of amplification, avoiding, e.g., stoichiometric problems. In some embodiments where less sensitivity is sought, less cDNA may be used. For example, in some embodiments, an amount of cDNA approximately in balance with 60,000 molecules of β-actin CT can be used, allowing reduced consumption of cDNA, e.g., by about 10-fold.

Figure 15:
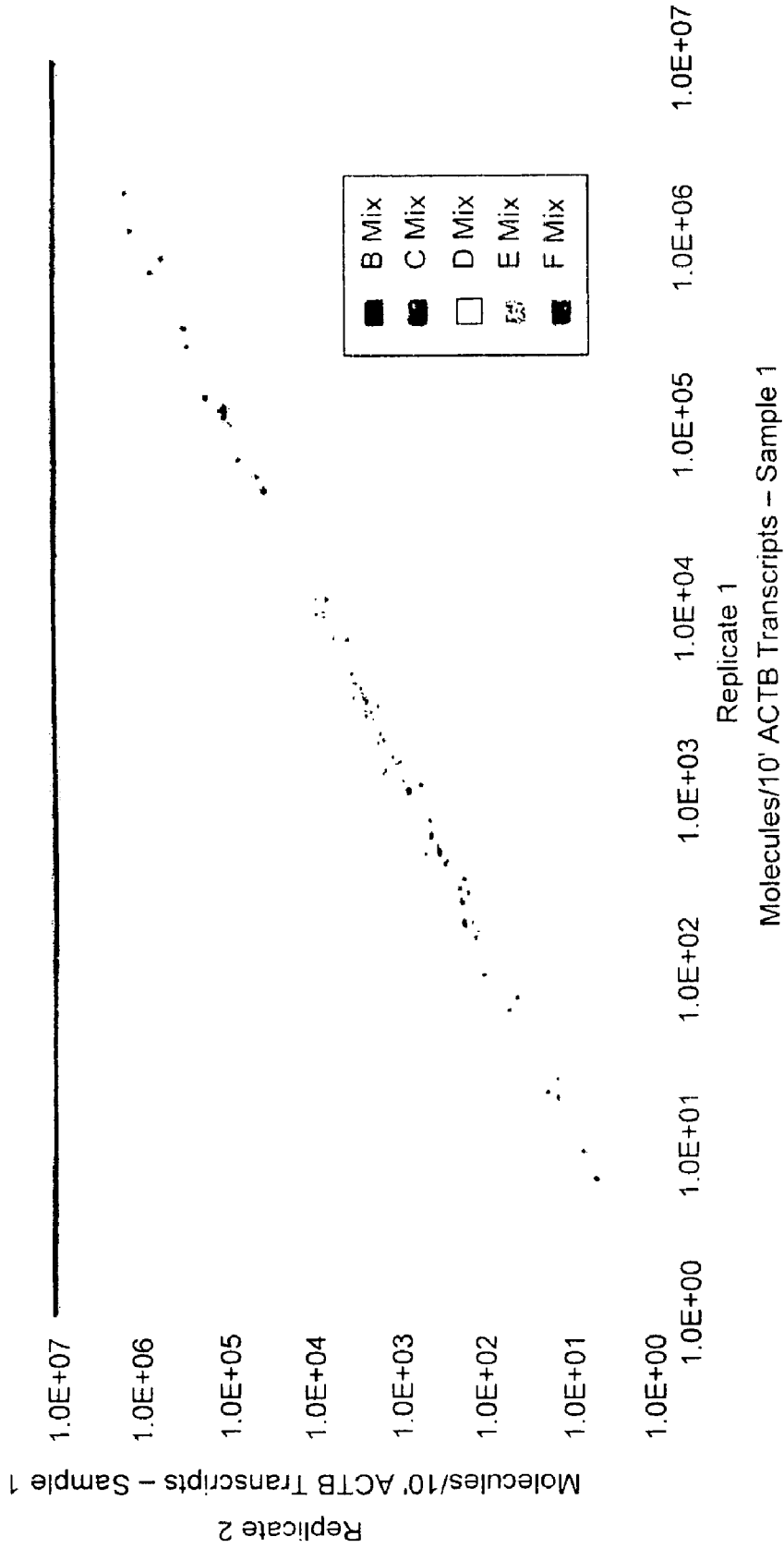
FIG. 15 illustrates use of Mix E initially, based on the expression levels of most genes.

A first one of the serially-diluted standardized mixtures can be selected for combing with the nucleic acid sample. FIG. 15 illustrates that Mix E can be used initially, based on the expression levels of most gene. There appears to be a stoichiometric and/or stochastic distribution of expression among genes (see, e.g., Kuznetsova, et al., General Statistics of Stochastic Process of Gene Expression in Eukaryotic Cells, Genetics, Vol. 161, 1321-1332, July 2002), with a mean approximately 2 orders of magnitude lower than the expression for β-actin, e.g., in human bronchial epithelial cells. Without being limited to a given theory and/or hypothesis, the distribution of gene expression levels in cells indicates that mRNA transcripts of many genes will be balanced with Mix E, in some embodiments.

FIG. 15 further illustrates that the use of a series of serially-diluted standardized mixtures of some embodiments can allow gene expression measurement over a full spectrum observed. As FIG. 15 illustrates through color-coding, different Mixes can be used to measure genes expressed at different levels with good reproducibility. Because there are about 100 to about 1,000 β-actin copies/cell for most cell types, this level of sensitivity allows measurement of 1 molecule per about 100 to about 1,000 cells. At the other end of the expression spectrum, a standardized mixture comprising greater concentrations of competitive templates can allow measurement of more highly expressed genes. For example, Mix A in some embodiments, can allow measurement of more than $10^7$ molecules/$10^6$ molecules of β-actin (about 1,000 to about 10,000 copies/cell). Examples of genes expressed at these levels, include UGB (Genbank no. U01101) and vimentin (X56134).

In other embodiments, a different mix may be used initially based on past experience and/or prediction of the amounts of nucleic acid expected. For example, Mix A, Mix B, Mix C, Mix E, or Mix F may be used initially. In preferred embodiments, the mixture selected is one containing a concentration of competitive template likely to be approximately calibrated with (e.g., within about a 10-fold range) the gene or genes being assessed. In preferred embodiments, an appropriate standardized mixture can be selected based on data in some embodiments of standardized expression databases described herein.

After combining a sample comprising a nucleic acid to be measured with one of the series of serially-diluted standardized mixture, the nucleic acid and its competitive template can be co-amplified, e.g., as described in detail above. Also as described above, a ratio can be obtained comparing amount of amplified product of the nucleic acid to amount of amplified product of its corresponding competitive template. Although a reference nucleic acid in the sample was balanced with its competitive template in the Mix, the target nucleic acid may not be balanced. Where the amounts of amplified product of a target nucleic acid and of its competitive template differ greatly, the co-amplification may be repeated using a different Mix of the series of serially-diluted mixtures. That is, a second and/or subsequent serially-diluted standardized mixture can be selected for combing with the nucleic acid sample.

Figure 16:
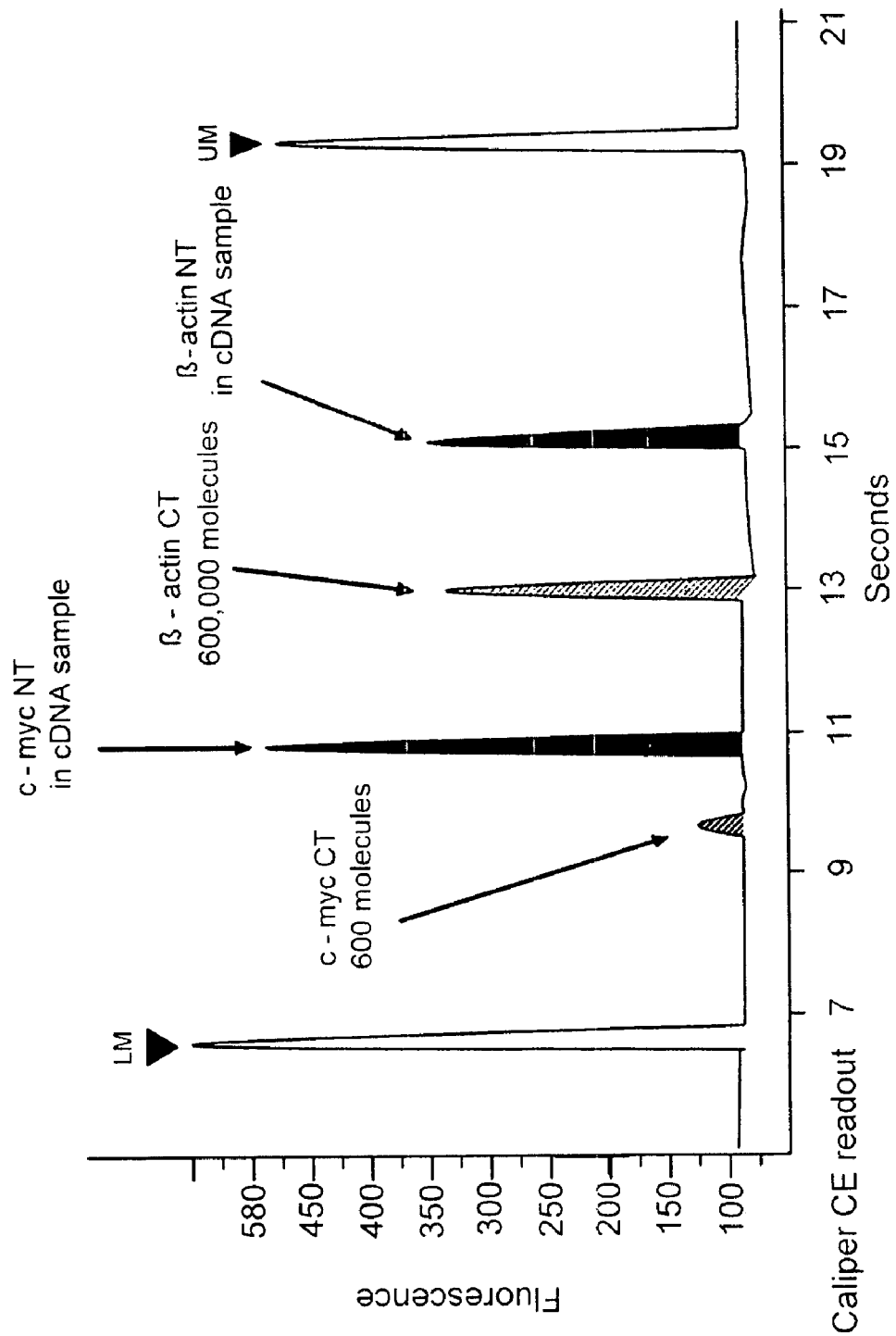
FIG. 16 illustrates a situation where the initial Mix used does not provide competitive template for the target nucleic acid (c-myc) sufficiently in balance with the amount of target nucleic acid in the dilution used.

FIG. 16 illustrates a situation where the initial Mix did not provide competitive template for target nucleic acid sufficiently in balance with the amount of target nucleic acid in the cDNA dilution. The target nucleic acid in this illustration corresponds to c-myc. As FIG. 15 illustrates, amplified product of c-myc NT is not within about a 10-fold amount of amplified product of c-myc CT. In some embodiments, software determines areas under curve for the NT and CT and calculates the ratio of NT/CT for the target nucleic acid.

In preferred embodiments, the next Mix selected from the series is based on the ratio obtained when amplified product of the target nucleic acid is compared to amplified product of its competitive template. For example, where the ratio is less than about 1/10, a more dilute mixture from the series will be used subsequently; where the NT/CT ratio is more than about 10/1, a more concentrated mixture from the series will be used. FIG. 16 illustrates the situation where a large ratio is obtained, indicating that a more concentrated Mix should be used next, e.g., Mix C. In some embodiments, software can be used to automatically determine which Mix should be selected next. In FIG. 16, software may estimate that c-myc NT is amplifying in the $10^4$ range and recommend Mix C as a more appropriate Mix.

Figure 17:
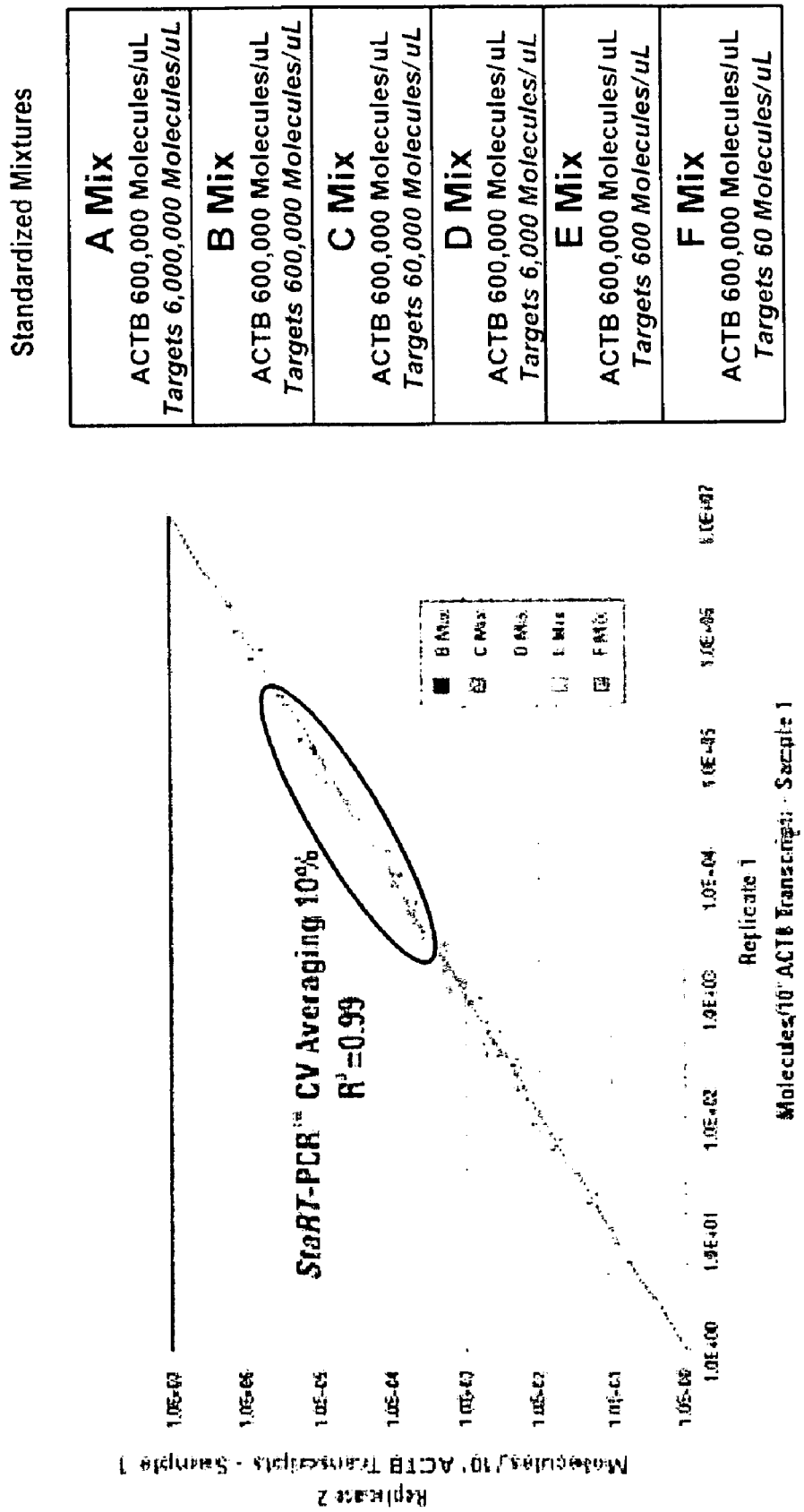
FIG. 17 illustrates selection of a subsequent mix, Mix C, based on results obtained using the first Mix.

FIG. 17 further illustrates selection of Mix C. The NT/CT ratio obtained for the target nucleic acid (c-myc in this illustration) is plotted on a graph. Position on the graph can indicate which Mix should be used for nucleic acid expressed at that level. In some embodiments, described in more detail below, software automatically communicates the correct Mix to be used to a robot.

Another sample of the nucleic acid, e.g., at the same cDNA dilution, can then be combined with the subsequently-selected serially-diluted standardized mixture. After combining, the nucleic acid and its competitive template can be co-amplified, e.g., as described in detail above. Also as described above, a ratio can be obtained comparing amount of amplified product of the nucleic acid to amount of amplified product of its corresponding competitive template.

Figure 18:
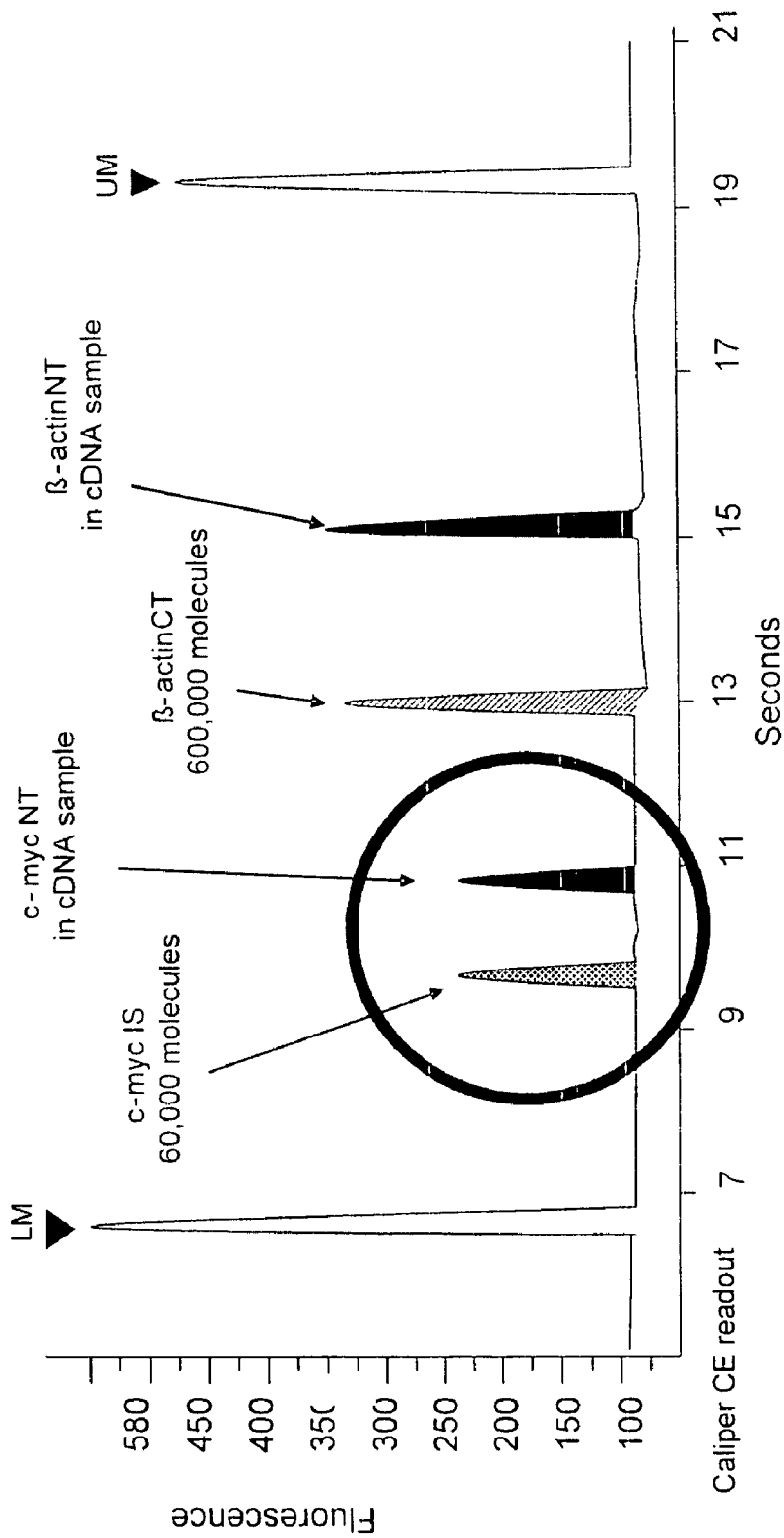
FIG. 18 illustrates the situation where the subsequent mix selected, Mix C, does provide competitive template for the target nucleic acid (c-myc) sufficiently in balance with the amount of target nucleic acid in the cDNA dilution used.

FIG. 18 illustrates the situation where the next Mix selected does provide competitive template for target nucleic acid sufficiently in balance with the amount of target nucleic acid in the cDNA dilution. As FIG. 18 illustrates, amplified product of c-myc NT is within about a 10-fold amount of amplified product of c-myc CT. In some embodiments, software determines area under curve for the NT and CT and calculates the ratio of NT/CT for the target nucleic acid. In some embodiments, software can also compare this ratio with the NT/CT ratio for the nucleic acid serving as a reference.

In preferred embodiments, the amount of sample cDNA can be kept constant while a different standardized mixture is used. As another example, if Mix D were used and the amount of amplified product of the NT was more than 10-fold greater than that of the corresponding CT, the experiment can be repeated with the same starting amount of cDNA, but using Mix C, which has about a 10-fold higher concentration of the competitive template, or Mix A or Mix B. Where the amount of amplified product is less than 10-fold lower than that of the corresponding CT, the experiment can be repeated with the same starting amount of cDNA, but using Mix E or Mix F. The more dilute mixture and/or the more concentrated mixture selected may be the next more dilute and/or more concentrated mixture in the series or a different serially-diluted mixture in the series, e.g., depending on the magnitude of the ratio obtained.

A highly preferred embodiment, in terms of cDNA consumption and reduced cost, involves using 1 μl of balanced cDNA in round one of a two-step process with each of the six (A-F) competitive template mixes; using 10 nanoliters of the round one amplified product in parallel 100 nanoliter volume round two amplifications to measure amounts of all of the 96 nucleic acids using Mix E (which contains competitive templates at a concentration that will be in balance with the majority of genes); and then repeating the above steps for nucleic acids that are not in balance with Mix E using the appropriate mix.

Figure 19:
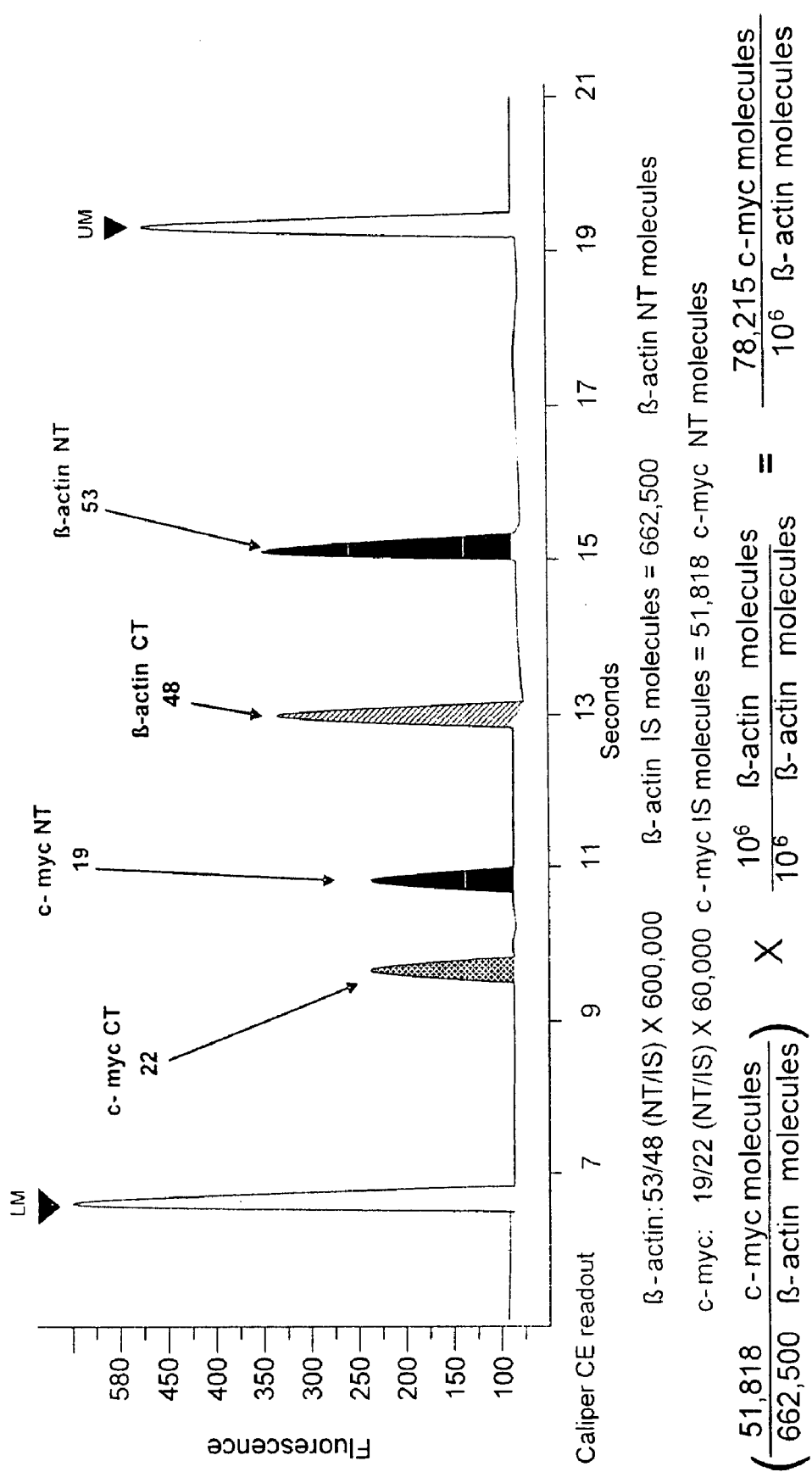
FIG. 19 illustrates calculation of a "ratio of ratios" based on data obtained using an appropriate Mix.

When an appropriate mix is used, amount of target nucleic acid can be assessed, in accordance with methods described herein. FIG. 19 illustrates calculation of a "ratio of ratios" based on data obtained using an appropriate Mix.

Figure 20:
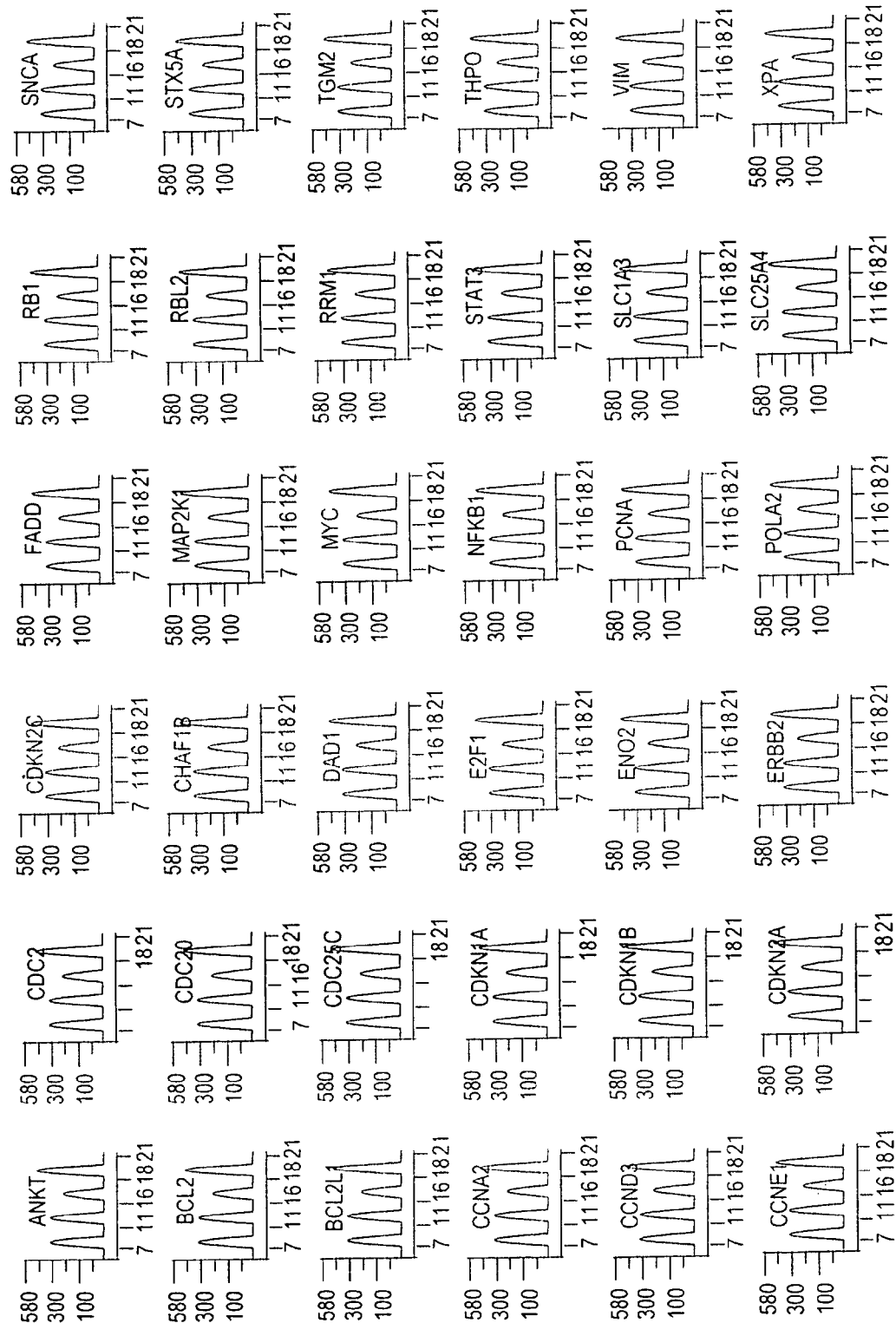
FIG. 20 illustrates a series of electropherograms for various genes.

FIG. 20 illustrates a series of electropherograms, e.g., as can be obtained in preferred embodiments where multiple nucleic acids are assessed together. While sample nucleic acid is generally referred to as cDNA in the above Figures, genomic DNA may also be use. Further, the nucleic acid assessed may be a nucleic acid having one or more allelic variations as described herein. Addition details regarding the practice of various steps outlined above are provided in the Example III below.

Figure 21:
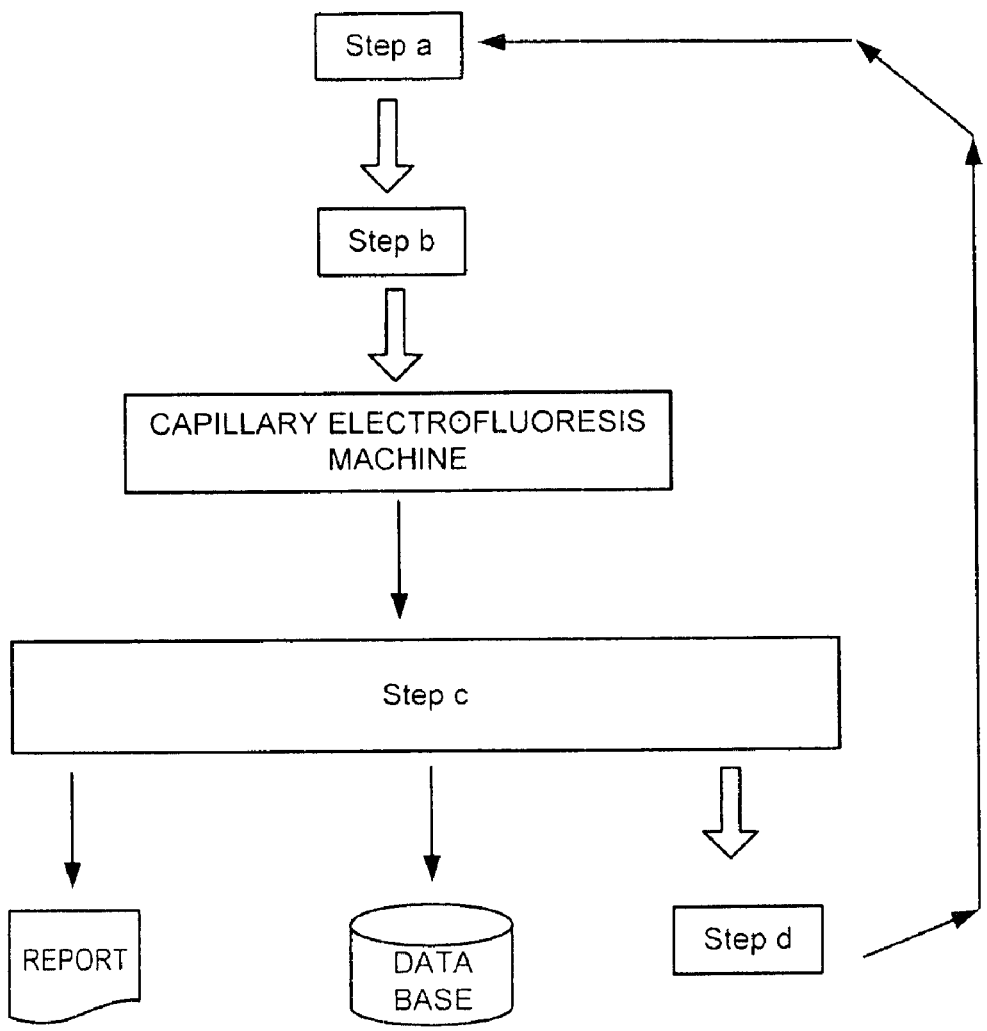
FIG. 21 illustrates an overall system for assessing nucleic acids, one or more steps of which may be computer implemented in various embodiments.

As indicated above, in some embodiments, the method for assessing nucleic acids using a series of serially-diluted standardized mixtures is computer implemented. FIG. 21 schematically illustrates an overall system for assessing nucleic acids, one or more steps of which may be computer implemented in various embodiments.

At step (a) a software program can determine a desired concentration of competitive template reagents to be used. This step can comprise selecting a sample dilution and/or selecting a Mix of a series of serially-diluted mixtures for combining. For example, computer implementation may comprise instructing a robotic handler to select a first one of the serially-diluted standardized mixtures for combining, e.g., Mix E as detailed above.

At step (b) a software program can cause at least one reagent to be dispensed into one or more vessels, in which the amplification reactions are to be conducted; and amplified product can be directed to a suitable device for separating, identifying and/or labeling, e.g., by flowing to a microfluidic capillary electrophoresis (CE) machine and/or by application to an array, as described herein. In some embodiments, this step may comprise instructing a robotic handler to dispense a selected Mix and/or sample dilution in a vessel, co-amplifying nucleic acids and their corresponding competitive templates, and separating amplified product.

At step (c), information regarding the separated amplified products can be analyzed. For example, step (c) may comprise obtaining a relationship comparing amplified product of a nucleic acid to amplified product of its competitive template. For example, after sufficient gel electrophoresis, gels can be digitally imaged automatically, and the image automatically analyzed to assess amounts of amplified product, e.g., by automatically determining area under the curves. For example, software can determine area under the curves for the NT and CT of a given nucleic acid and calculate the ratio of NT/CT. In some embodiment, the relative amounts of fluorescence, e.g., for distinguishable detectable moieties hybridized to immobilized amplified products on an array, may be measured and used to determine relations, e.g., as taught herein.

In some embodiments, calculation steps are incorporated into a spreadsheet. For example, in some embodiments, a user can enter raw values (e.g., for fluorescence intensity, peak heights or area under the curve) for the NT, CT, and heterodimer PCR products for a given gene to be measured into a spreadsheet, and the expression value for the gene can be automatically calculated. In some embodiments, software can be used to automatically enter values for NT and CT amplified product for each of one or more nucleic acids to be measured into a spreadsheet to automatically calculate a numerical value, e.g., a numerical value corresponding to gene expression Information from step (c) can be provided in a "Report", sent to a "Database" and/or sent to step (d), which can reiterate the process for further analysis of data received. For example, if the calculated ratio is not within a desired range (for example, within about a 1:10 to about a 10:1 ratio) as described above, a new desired concentration of competitive template reagents (i.e., different from the original concentrations selected to step (a)) may be chosen and the steps (b)-(c) are repeated. In some embodiments, software can be used to automatically determine which Mix should be selected next, based on considerations described above. In some embodiments, a software program can instruct a robotic handler to combine a sample with the new Mix.

Another aspect of the present invention is directed to a computer program for implementing certain embodiments of methods of the instant invention. In certain embodiments, the computer program includes a computer readable medium and instructions, stored on the computer readable medium. In preferred embodiments, the instructions include one or more steps recited above. The computer program can further include instructions for dispensing amplified product into arrays for measurement, as well as instructions for fluorescently labeling amplified product and/or nucleic acid to which they hybridize. Amplified product may be labeled, e.g., by labeling one or more nucleotides in the amplification reaction with a detectable moiety, e.g. a fluorescent moiety and/or using distinguishably labeled detection moieties, as described herein. The computer program can further include instructions for measuring amounts of nucleic acid, e.g., by comparing fluorescent intensities of the arrays for the amplified product of a given nucleic acid and its competitive template.

In some embodiments, methods for assessing allelic variation and/or allelic frequency are computer implemented. For example, the one or more of the steps of the methods provided above may be automated, e.g., by a computer program. The computer program may comprise a computer readable medium and instructions stored on the computer readable medium for carrying one of more of such steps. Instruction may comprise, for example, receiving data generated from any of the methods described herein. For example, one or more relations comparing amplified products may be obtained by automatically reading various fluors from predetermined positions on an array. Some embodiments of the instant invention are directed to a computer program product for implementing, monitoring, and enforcing quality control in diagnostic applications, such as in molecular diagnostic testing.

G. Sensitivity

Some embodiments of the present invention described above provide a relationship for assessing nucleic acid where the relationship with sensitivity. Sensitivity can be defined as the ability of a procedure to produce a change in signal for a defined changed in the quantity of analyte, i.e., the slope of a calibration curve. Some embodiments of the instant invention provide a slope greater than about 0.1, greater than about 0.2, greater than about 0.5, or greater than about 0.8. Some preferred embodiments of the instant invention provide a slope of about 1/1.

For example, some embodiments of the instant invention provide a relationship capable of detecting less than about a two-fold difference, less than about a one-fold difference, less than about an 80% difference, less than about a 50% difference, less than about a 30% difference, less than about a 20% difference, less than about a 10% difference, less than about a 5% difference, or less than about a 1% difference. Such sensitivities can correspond to identifying small changes in gene expression and/or same variation in allele representation.

In some embodiments one or more of these differences can be detected in about 1,000 molecules or less of the nucleic acid in the sample, e.g., in about 800, in about 600, or in about 400 molecules. In some embodiments, one or more of these differences can be detected in about 100 molecules or less (e.g., in about 60 molecules), in about 10 molecules or less (e.g., in about 6 molecules), or in about 1 molecule or less of the nucleic acid in a sample. In some embodiments, one or more of these differences can be detected in less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of the nucleic acid in a sample.

Some embodiments, as described above, assess nucleic acids over a range of concentrations, e.g., assessing gene expression over one or more orders of magnitude of gene expression and/or alleles occurring over a range of frequencies. In some such embodiments, assessing detects less than about a two-fold difference over the range. In some embodiments, assessing detects less than about a one-fold difference, less than about an 80% difference, less than about a 50% difference, less than about a 30% difference, less than about a 20% difference over said range, less than about a 10% difference, less than about a 5% difference, or less than about a 1% difference over the range.

Sensitivities described herein can be achieved by some of the embodiments of the instant invention.

H. Reproducibility

In preferred embodiments, methods of assessing a nucleic acid are reproducible. Some embodiments, for example, provide a coefficient of variation of less than about 25% between samples of a nucleic acid. In some embodiments, the coefficient of variation is less than about 50%, less than about 30%, less than about 25%, less than about 20%, less than about 15%, less than about 10%, less than about less than about 5%, or less than about 1% between 2 of more samples of the nucleic acid. Such coefficients of variation can be obtained in some embodiments where the 2 samples are amplified and/or assessed at different times, e.g., on different days; in the same or different experiments in the same laboratory; and/or in different experiments in different laboratories; and/or where the samples are obtained from different subjects and/or different species. Preferred embodiments of the present invention provide both intra- and inter-laboratory reproducibility (M. T. Vondracek, D. A. Weaver, Z. Sarang et al., *Int. J. Cancer* 99, 776-782 (2002)) that is sufficient to detect less than two-fold differences in gene expression. For example, in some embodiments, inter-laboratory correlation of variance was 0.48, e.g., from gene expression measurements using a A549 cDNA sample taken in different laboratories at different times, spanning nearly one year. In some embodiments, e.g., embodiments using micro-channel capillary electrophoresis, the correlation of variance was reduced to 0.26. Additional details of a study to evaluate reproducibility are provided in Example IV below.

In some embodiments, reproducibility between samples allows for the use of fewer dilution tubes. In some embodiments, a single tube may be used, simplifying procedures and permitting the evaluation of many different samples at one time.

In some embodiments, including competitive template internal standards in a common standardized mixture used in different measurements can control for one or more sources of variation. Sources of variation include, e.g., variation from cDNA loading, intra-nucleic acid amplification efficiency, inter-nucleic acid amplification efficiency, inter-specimen amplification efficiency, inter-sample amplification efficiency, and/or intra-sample amplification efficiency. For example, some embodiments using an Agilent 2100 Bioanalyzer provide reproducibility intra-lab CV of less than about 0.25 routinely, with a sensitivity comparable to slab gel electrophoresis.

TABLE I tabulates a number of sources of variation and control methods.
Sources of Variation in Quantitative RT-PCR Gene Expression Measurement and Control Methods

| Source of Variation | Embodiments of methods described herein | Real-time |
|---|---|---|
| cDNA loading: Due to variation in pipetting, quantification, reverse transcription. Consequence: unreliable comparison of expression for same gene in two different samples | Multiplex Amplify with Reference Gene (e.g. β-actin) | Multiplex Amplify with Reference Gene (e.g. β-actin) |
| Intra-nucleic acid Amplification Efficiency Cycle-to-Cycle Variation: early slow, log-linear, and late slow plateau phases Consequence: unreliable comparison of expression for same gene in different samples | Internal standard CT for each gene in a Standardized Mixture of Internal Standards (SMIS) | Real-time measurement |
| Inter-nucleic acid Amplification Efficiency: in efficiency of primers Consequence: unreliable comparison of expression for different genes in the same or different samples | Internal standard CT for each gene in a SMIS | External standard curve for each gene measured |
| Inter-specimen Amplification Efficiency: variable presence of an inhibitor of PCR Consequence: unreliable comparison of expression for same or different gene in same or different samples | Internal standard CT for each gene in a SMIS | Standard curve of reference sample compared to test sample[2] |
| Inter-sample Amplification Efficiency: in quality and/or concentration of PCR reagents (e.g. primers); in presence of an inhibitor of PCR Consequence: unreliable comparison of expression for same or different genes in same or different samples | Internal standard CT for each gene in a SMIS | None[2] |
| Intra-sample Amplification Efficiency: in thermocycler efficiency Consequence: e.g., unreliable comparison of expression for same or different gene in same or different samples | Internal standard CT for each gene | None[2] |

Variation in cDNA loading may result from variation in pipetting, aliquoting, quantification, and/or reverse transcription. For example, errors may occur when aliquotting RNA material into vessels for performing reverse transcription. Although reverse transcription efficiency can vary from one sample to another, the representation of one nucleic acid to another in a sample need not vary among different reverse transcriptions.

For example, the efficiency of reverse transcription can vary from about 5 to bout 90% (Simmonds et al, 1990). Variation in reverse transcription efficiency, however, may affect different transcripts in the same or substantially the same manner (Willey et al, 1998; Loitsch et al, 1999). In one experiment, for example, gene expression was measured in 5 different reverse transcriptions of a given sample of RNA from the SW900 non-small cell carcinoma cell line. The mean level of expression obtained was 3,600 molecules/$10^{-6}$ β-actin molecules with a CV of 0.26, no greater than if replicate measurements had been made on cDNA resulting from a single reverse transcription. However, if reverse transcription and amplification reactions are carried out in different vessels, errors may occur when pipetting cDNA from the reverse transcription reaction into individual PCR reaction vessels. That is, without being limited to a particular theory and/or hypothesis, the effect of variation in reverse transcription can be the same as if different levels of cDNA were loaded in a PCR reaction. Controlling for cDNA loading can then control variation in reverse transcription efficiency.

Variation in intra-nucleic acid amplification efficiency may result from, e.g., cycle-to-cycle variation, e.g., where different amplification cycles show various early slow, log-linear and/or late slow plateau phases, as described above. Where gene expression is being measured, intra-nucleic acid amplification efficiency can refer to intra-gene amplification efficiency, i.e., for example, variation in repeat amplifications of cDNA corresponding to a given gene.

Variation in inter-nucleic acid amplification efficiency can refer to inter-gene amplification efficiency, e.g., where the efficiency at which a given gene is amplified differs from that at which a different gene is amplified. Such differences may be caused by, e.g., differences in the primers used for amplifying the different genes measured in the same and/or different samples. For example, the efficiency of a pair of primers, e.g., as defined by lower detection threshold (LDT), may not be predictable, and may vary more than about 100,000-fold (from less than about 10 molecules to about $10^6$ molecules) in some embodiments.

Also, a bad lot (e.g., where degradation of primers and/or competitive templates has occurred) or inappropriate concentration of primers would cause variation in PCR amplification of one nucleic acid relative to another. In some embodiments, the concentration of competitive template is small (e.g., femptomolar range) so that any change in the number of molecules present in the reaction may introduce a large source of error. Presence of an inhibitor could alter PCR amplification efficiency of one nucleic acid, e.g., one gene, compared to another.

Variation in inter-specimen amplification efficiency may be caused by, e.g., variable presence of an inhibitor (e.g., an inhibitor of PCR) in different specimen. PCR reactions inhibitors, include, e.g., heme. Akane, A., Matsuara, K., Nakamura, H., Takahashi, S., and Kimura, K. (1994) Identification of the heme compound co purified with deoxyribonucleic acid (DNA) from blood stains, a major inhibitor of polymerase chain reaction (PCR) amplification. *J. Forensic Sci.* 39, 362 372; Zhu, Y. H., Lee, H. C., and Zhang, L. (2002) An examination of heme action in gene expression: Heme and heme deficiency affect the expression of diverse genes in erythroid K562 and neuronal PC12 cells. *DNA Cell Biol.* 21, 333 346. Further, amplification efficiency for different genes may be affected to different degrees in different samples and/or specimen. Meijerink, J., Mandigers, C., van de Locht, L., et al. (2001) A novel method to compensate for different amplification efficiencies between patient DNA samples in quantitative real-time .PCR. *J. Mol. Diagn.* 3, 55-61; Giulietti, A., Overbergh, L., Valckx, D., et al. (2001) An overview of real-time quantitative PCR: applications to quantify cytokine gene expression. *Methods* 25, 386-401. Such differences may result in variation in measuring the same or different nucleic acids (e.g., the same or different genes) in the same or different specimen and/or samples. For example, a given PCR inhibitor may have little affect on amplification of a lowly expressed gene, e.g., GSTM3. The same PCR inhibitor may have a larger effect, e.g., a significantly larger effect, on amplification of a more-highly expressed gene, e.g., ERBB2, including, e.g., preventing amplification or reducing amplification to non-detectable levels.

Variation in inter-sample amplification can refer to inter-reaction variation or well-to-well variation in repeat measurements of the same or different nucleic acids (e.g., the same or different genes) in the same or different samples and/or specimen. Variation in inter-sample amplification efficiency can result from, for example, variable presence of an inhibitor (e.g., an inhibitor of PCR) in different reaction vessels, variation in temperature cycling between different region of a themocycler block, variable quality of one or more PCR reagents or variable concentrations of one or more PCR reagent (e.g., primers).

One or more of these sources of variation can reduce PCR amplification efficiency in a well to the point where no PCR product can be observed in that well. Some embodiments of the instant invention allow this type of error to be recognized, for example, embodiments using a standardized mixture comprising about $10^{-17}$ M competitive template for the nucleic acid sought to be amplified. In a 10 µL PCR reaction volume, about $10^{-17}$ M represents about 60 molecules. With about 60 molecules of internal standard present in the PCR reaction and components of the PCR reaction functioning properly, if a nucleic acid is not present in a sample, the amplified product for the competitive template will be observed, but the amplified product for the nucleic acid will not. This may indicate that there was less than about six molecules (about 10-fold less than the number of competitive template molecules) of nucleic acid in the sample. On the other hand, if neither amplified product of neither the nucleic acid nor its competitive template is detectable, it can be determined that the PCR reaction efficiency was suboptimal.

Variation in intra-sample amplification can refer to intra-reaction variation, e.g., variable amplification efficiency in a given reaction using a given sample. Variation in intra-sample amplification efficiency may result from, e.g., variation in thermocycler efficiency at various positions within a thermocycler, and can introduce variation when measuring amounts of the same or different nucleic acids (e.g., expression of the same or different genes) in the same or different samples and/or specimen.

Some embodiments for measuring nucleic acids control for variation caused by one or more of sources of variation selected from cDNA loading, intra-nucleic acid amplification efficiency, inter-nucleic acid amplification efficiency, inter-specimen amplification efficiency, inter-sample amplification efficiency, and intra-sample amplification efficiency. For example, in some embodiments, use of a standardized mixture and/or a series of serially-diluted standardized mixtures can provide control. Further, in some embodiments, use of positive contorts, e.g. positive controls for one or more alleles, can control for variation in hybridization (e.g., between the target nucleic acid and its competitive template), variation in detection moieties (e.g., Cy3 vs. Cy5 fluorescent probes), variation in detection moieties from one lot to another, and the like, as described in more detail above.

Some preferred embodiments control for one or more sources of variation without the use of real-time measurements obtained using kinetic analysis (e.g., real-time PRC measurements). For example, obtaining a "ratio of ratios" in some embodiments does not involve taking real-time measurements. Some preferred embodiments control for one or more of sources of variation without generating one or more standard curve(s). For example, obtaining a "ratio of ratios" in some embodiments does not involve generating a standard curve. In more preferred embodiments, one or more sources of error are controlled for using methods that do not involve real-time measurements nor generation of a standard curve. In even more preferred embodiments, two or more, three or more, four or more, five or more or six sources of variation are controlled for without real-time measurements nor generation of a standard curve.

Figure 22:
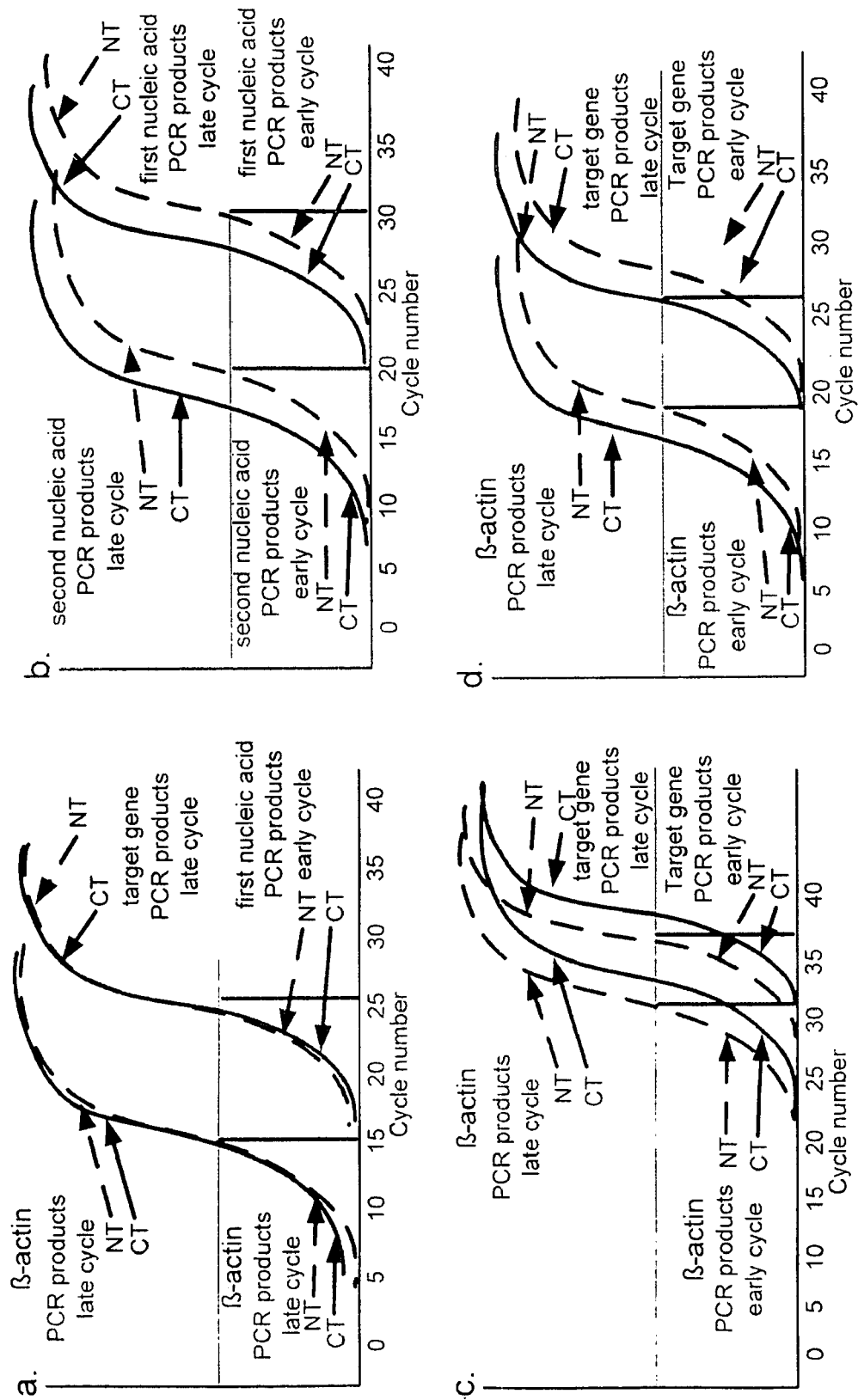
FIG. 22 illustrates the control of one or more sources of error in some embodiments compared to real-time RT-PCR in two different specimen in four different experiments.

FIG. 22 illustrates the control of one or more of these sources of error in some embodiments compared to real-time RT-PCR in two different specimen in four different experiments. Some embodiments of the instant invention do not involve real time measurements and/or the generation of a standard curve. In FIG. 22, the nucleic acids being measured are referred to as native template (NT), the competitive template for each is referred to as CT, and the second nucleic acid serves as the reference nucleic acid.

FIG. 22 illustrates amplified product of native template and competitive template for a first and a second nucleic acid that are PCR-amplified simultaneously for indicated number of cycles. The amplified products at endpoint are electrophoretically separated, e.g., in the presence of fluorescent intercalating dye, and quantified densitometrically. In the illustrated embodiment, the shorter CT PCR product migrates faster than the NT PCR product, and is represented by a CT band below the NT band. As one of skill in the art will understand, if there is more NT product than CT product, the NT band will emit more fluorescent light; if there is more CT product than NT product, the CT band will emit more fluorescent light. In real-time, the fluorescent PCR product is measured at each of the 35 to 40 cycles. FIG. 22 illustrates how the reactions would look if measured at each cycle in real time and the CT for the real-time curve is represented by the perpendicular black line.

FIG. 22a illustrates that the ratio of NT/CT present at the beginning of PCR remains (substantially) constant throughout PCR to endpoint. As described above, it is not necessary to monitor the amplification reaction in real-time to ensure that the reaction is in log-linear phase in some embodiments of the instant invention.

FIG. 22a illustrates an experiment using a first sample of a first specimen. In the first sample, there are about equivalent number of molecules of the second nucleic acid NT and CT present at the beginning of the PCR reaction (e.g., as described above, where a balanced cDNA dilution is used). Thus, following electrophoresis of the amplified product of the second nucleic acid, the NT and CT bands are about equivalent, and during real-time measurement, the fluorescent intensity for the NT will be about the same as for the CT. The NT/CT ratio is the same at an early cycle as it is at a late cycle (endpoint), even though the band intensity for both NT and CT is low at early cycle compared to late cycle. Similarly, the first nucleic acid NT band and CT band are about equivalent, and the real-time value for the NT is about the same as for the CT. The $\Delta C_T$ between the second and the first nucleic acid in real-time measurements is about 10.

FIG. 22b further illustrates controls for loading from one sample to another. In FIG. 22b, the first specimen is re-analyzed using a lower starting amount of nucleic acid, e.g., less cDNA loaded, due to a variation in pipetting, e.g., in aliquoting a second sample of the first specimen into a different vessel. The NT/CT ratio for the second nucleic acid is lower. However, because the relative concentration of competitive templates is fixed and the relative representation of each nucleic acid is fixed, the NT/CT ratio for the first nucleic acid goes down commensurately. Accordingly, the "ratio of ratios" (odds ratio) of the first nucleic acid NT/CT divided by second nucleic acid NT/CT remains the same is in FIG. 22a. In this case, the $\Delta C_T$ in real-time analysis is also unchanged.

FIG. 22c illustrates controls for loading and variation in amplification efficiency. In FIG. 22c, the first specimen is again re-analyzed, but with both (1) a larger amount of cDNA loaded due to variation in pipetting (leading to variation in starting amount of native template) and (2) lowered amplification efficiency of the second nucleic acid, as might be caused by inhibitor in the well that affects amplification of this nucleic acid more than the other, or inappropriate concentrations of primers for the second nucleic acid.

FIG. 22c illustrates that with real-time measurements, this reduces the $\Delta C_T$ from 10 to 6, and the value for the first nucleic acid is inappropriately high. In real-time measurements, the gene selective inhibition is associated with a decreased $\Delta C_T$ and erroneous measurement.

In contrast, using certain embodiments described herein, because the amplification efficiency of the NTs for each of the two nucleic acids is affected the same way as its corresponding CT, the NT/CT ratio is unchanged in FIGS. 22a and 22c for either first or second nucleic acid. Also, with the larger amount of cDNA loaded, the first nucleic acid NT/CT ratio and the second nucleic acid NT/CT ratio increase commensurately. Accordingly, the "ratio of ratios" (odds ratio) of first nucleic acid NT/CT divided by the second nucleic acid NT/CT stays the same between FIGS. 22a and 22c.

FIG. 22d further illustrates controls for loading a sample of a second specimen, where the first nucleic acid is more highly expressed. Although, the first nucleic acid is expressed at a higher level compared to the second nucleic acid, real-time measurements give a $\Delta C_T$ of about 7.

In contrast, using certain embodiments of described herein, the ratio of ratios indicates the higher level of expression. As less cDNA is loaded into the PCR reaction, there are fewer copies of the second nucleic acid NT than CT copies present at the beginning of the PCR reaction compared with FIG. 22a. Throughout real-time measurement, the fluorescence value of the NT is less than that of the CT and at the end of PCR, the second nucleic acid NT band is still less than the CT band. However, even though less cDNA was loaded into the PCR reaction compared to the first sample, the first nucleic acid NT band is more dense than the first nucleic acid CT band due to its higher expression, and the first nucleic acid NT fluorescence value during real-time measurement is higher throughout PCR. Accordingly, the "ratio of ratios" (odds ratio) of first nucleic acid NT/CT divided by the second nucleic acid NT/CT provides a higher value in FIG. 22d than in FIG. 22a.

Thus real-time RT-PCR may control for loading by measuring the first and second nucleic acids in the same PCR reaction (FIGS. 22a, 22b, 22d). The $C_T$ (for each nucleic acid represented by a black line intersecting with the X axis) for the first and second nucleic acids both could vary from one experiment to another, but the $\Delta C_T$ do not vary. However, real-time does not control for variation in the presence of inhibitors, or the quality of PCR reagents.

Use of arrays to assess amplified product, e.g., as taught herein, can provide additional advantages. For example, the arrays also allow for intra-nucleic acid comparison within a sample as well as comparison of multiple samples run at different times and locations. Also, the use of a ratio of a ratio of target gene/reference gene can control for variation of fluorescent intensities between fluors, allowing reproducible gene expression measurements.

I. Accuracy

In some embodiments, methods provided herein can reduce false negatives and/or false positives for a given nucleic acid and/or allele of a given nucleic acid. In preferred embodiments, false negatives and/or false positives may be reduced to a statistically insignificant number. In even more preferred embodiments, methods provided herein can eliminate false negatives and/or false positives. In some embodiments, quality control is facilitated by the presence of competitive template for each target nucleic acid being assessed and the simultaneous presence of a competitive template for a reference nucleic acid for each reaction (that can control for loading). With the additional use of positive and/or negative controls, as provided herein, there may be no false negatives and a statistically insignificant number of false positives, in some preferred embodiments.

II. Methods of Preparing Compositions for Assessing Nucleic Acid

Another aspect of the instant invention relates to methods for preparing compositions for assessing a nucleic acid in a sample.

A. Preparation of Standardized Mixtures

Some embodiments of the invention provide a method for preparing a standardized mixture of reagents. As used herein, "reagent" can refer to a component used in a mixture, including solvent and/or solute. For example, reagents include nucleic acids and/or water, e.g., in the case of aqueous mixtures. In some embodiments, the standardized mixture of reagents comprises sufficient amounts of competitive template for assessing amounts of a number of nucleic acids in a number of samples, e.g., more than about $10^6$ samples. In preferred embodiments, the standardized mixture allows direct comparison of the amounts between at least 2 of the samples. More preferred embodiments allow direct comparison of amounts assessed in at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some specific embodiments, the standardized mixture allows direct comparison of amounts assessed in up to an unlimited number of samples.

In some embodiments, the standardized mixture comprises sufficient reagents for assessing amounts of one nucleic acid. In some embodiments, the standardized mixture comprises sufficient reagents for assessing amounts of more than one nucleic acid, e.g., at least about 50, at least about 96, at least about 100, at least about 200, at least about 300, at least about 500, at least about 800, at least about 1,000, or at least about 5,000, at least about 10,000, at least about 50,000, or at least about 100,000 nucleic acids. In some embodiments, the standardized mixture comprises sufficient reagents for assessing amounts of less than about 100,000, less than about 500,000, or less than about 1,000,000 nucleic acids. In some preferred embodiments, different nucleic acids correspond to different gene transcripts. In some preferred embodiments, different nucleic acids correspond to different allelic variations of expressed and/or genomic material.

In some embodiments, the reagents include at least one forward primer and/or at least one reverse primer capable of priming amplification of a competitive template in the mixture. In some embodiments, a forward primer and/or a reverse primer are designed to have substantially the same annealing temperature as another forward primer and/or reverse primer in the standardized mixture. Designing primers with the same or substantially the same annealing temperature can allow amplification reactions to achieve approximately the same amplification efficiency under identical or substantially identical conditions. In such embodiments, if there is variation in amplification efficiency, amplification efficiency of a nucleic acid and its competitive template can be affected identically (or substantially identically), so that the ratio of amplified product of the nucleic acid and its corresponding competitive template may not vary or may not substantially vary. In some specific embodiments, a forward and reverse primer have the same or substantially the same annealing temperature as each of the other forward and reverse primers in a given standardized mixture. For example, the annealing temperature may be about 40° C., about 40° C., about 44°, about 50° C., about 55° C., about 57° C., about 58° C., about 59° C., about 60° C., about 65° C., about 70° C., about 75° C., or about 85° C.

In some embodiments, an internal standard competitive template can be prepared for a number of nucleic acids to be evaluated, including nucleic acids that can serve as one or more reference nucleic acids. In some embodiments, an internal standard serves as the competitive template of one or more allelic variations of a nucleic acid. The competitive templates can then be cloned to generate enough to assess amounts of a nucleic acid in more than about $10^4$ samples, in more than about $10^5$ samples, in more than about $10^6$ samples, in more than about $10^7$ samples, in more than about $10^8$ samples; in more than about $10^9$ samples, in more than about $10^{10}$ samples, in more than about $10^{11}$ samples, in more than about $10^{12}$ samples, in more than about $10^{13}$ samples, in more than about $10^{14}$ samples, or in more than about $10^{15}$ samples.

The competitive templates can be carefully quantified and then mixed together to form a standardized mixture. In some embodiments, the forward primer and/or reverse primer can be selected to allow for detection of about $10^{-10}$, about $10^{-11}$, about $10^{-12}$, about $10^{-13}$, about $10^{-14}$, about $10^{-15}$, about $10^{-16}$, about $10^{-17}$, about $10^{-18}$ M or less of the nucleic acid to be measured. For example, the forward and/or reverse primer can allow for the detection of about 600 molecules, about 60 molecules or about 6 molecules of the nucleic acid in some embodiments.

In some embodiments, a standardized mixture of the instant invention can measure and/or enumerate less than about 1,000 molecules of nucleic acid in a sample, e.g., about 800, about 600, or about 400 molecules. In some embodiments, less than about 100 molecules (e.g., about 60 molecules), preferably less than about 10 molecules (e.g., about 6 molecules), or more preferably less than about 1 molecule of a nucleic acid can be measured and/or enumerated in a sample. In some embodiments, a standardized mixture of the instant invention can measure and/or enumerate less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of a nucleic acid in a sample.

In some embodiments, the reagents include at least one positive control for at least one nucleic acid to be assessed. In some embodiments, e.g., positive controls for each of a pair of alleles of a target nucleic acid are provided as a standardized mixture. For example, a positive control for a first and/or a second allele for a target nucleic acid can be cloned, quantified and mixed with one or more other reagents. In some embodiment, the standardized mixture of positive controls provides at least one positive control at known concentration. The positive controls can then be cloned to generate enough for use as controls for more than about $10^4$ samples, for more than about $10^5$ samples, for more than about $10^6$ samples, for more than about $10^7$ samples, for more than about $10^8$ samples; for more than about $10^9$ samples, for more than about $10^{10}$ samples, for more than about $10^{11}$ samples, for more than about $10^{12}$ samples, for more than about $10^{13}$ samples, for more than about $10^{14}$ samples, or for more than about $10^{15}$ samples. In some embodiments, the alleles are provided co-linearly on a given nucleic acid construct, e.g., a plasmid, as described in more detail above. In preferred embodiments, a positive control for each expected allele is provided in a standardized mixture.

In some embodiment, the standardized mixture of positive controls provides at least one positive control at known concentration and at least one competitive template at known concentration, e.g., the competitive template for the target nucleic acid corresponding to the positive control. In some preferred embodiments, a positive control for an allele of a target nucleic acid can be provided in a standardized mixture that comprises an equal or substantially equal amount of the competitive template of the target nucleic acid. For example, the amounts of the positive control and the competitive template can be in a ratio of about 1:10 to about 10:1, preferably in a ratio of about 1:5 to about 5:1, more preferably in a ratio of about 1:2 to 2:1 and most preferably in a ratio of about 1:1.

In some embodiments, the reagents for measuring amounts of nucleic acids are stable. For example, the positive controls, primers and/or competitive templates of a standardized mixture may comprise stable nucleic acid molecules, such as DNA. Reagents may be stable for at least about 20 years, at least about 50 years, at least about 100 years, at least about 500 years, or at least about 1,000 years. In preferred embodiments, a standardized mixture of the present invention can provide reagents to measure sufficient nucleic acids corresponding to gene expression measurements expected to be made for at least about 20 years, at least about 50 years, at least about 100 years, at least about 500 years, or at least about 1,000 years, e.g., at the current rate of gene expression measurement (estimated to be about one billion assays a year (An economic forecast for the gene expression market http://www.researchandmarkets.com/reports/5545)).

In some embodiments, long term storage of reagents and/or samples comprising DNA can be achieved at about −20 degrees C. In some embodiments, reagents and/or samples comprising RNA are stable for years frozen as an EtOH precipitate and/or in RnASE free water. In some embodiments, competitive templates are stably frozen for more than about six years. In some embodiments, cDNA samples are stable for more than about two years frozen at −20 degrees C.

A standardized mixture according to some embodiments of the present invention can be prepared to perform one or more of the methods described herein. For example, as described above, using a standardized mixture, a nucleic acid can be assessed relative to one or more other nucleic acids (e.g., that can serve as controls for cDNA loaded into the reaction). Also as detailed above, a nucleic acid can be assessed relative to its respective competitive template provided in the standardized mixture. Also as detailed above, false negatives and/or false positives of a nucleic acid, e.g., an allelic variation of a nucleic acid, can be detected using a positive control provided in a standardized mixture, and the positive control can itself be assessed relative to competitive template.

In some embodiments, the standardized mixture can allow for detection with one or more of the sensitivities, one or more of the accuracies, one or more of the detection limits, and/or with more or more of the coefficients of variation taught herein. Additional features of the prepared standardized mixture will be apparent to one of skill in the art, based on the disclosure herein.

B. Preparation of Series of Serially-Diluted Standardized Mixtures

Some embodiments of the invention provide a method for preparing a series of serially-diluted standardized mixtures. In some embodiments, the one or more of the series of standardized mixtures comprises sufficient amounts of competitive templates for assessing amounts of a number of nucleic acids in a number of samples, e.g., more than about $10^6$ samples. In preferred embodiments, the standardized mixture allows direct comparison of the amounts between at least 2 of the samples. More preferred embodiments allow direct comparison of amounts assessed in at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some specific embodiments, the standardized mixture allows direct comparison of amounts assessed in up to an unlimited number of samples.

The series of serially-diluted standardized mixtures may be obtained by serially diluting a standardized mixture, e.g., a standardized mixture described above. For example, in some embodiments, one or more of the series may contain sufficient reagents for assessing various numbers of nucleic acids and/or for assessing various numbers of samples, e.g., as detailed above. Similarly, in some embodiments, one or more of the series of serially-diluted standardized mixtures can comprise any of the reagents of some embodiments of the standardized mixtures described above.

In preferred embodiments, a standardized mixture is diluted so that the competitive template for a first nucleic acid is at a series of concentrations relative to the competitive template for a second nucleic acid. In some embodiments, a standardized mixture is serially diluted 10-fold, providing 10-fold serial dilutions of the competitive template for the first nucleic acid relative to the competitive template for the second nucleic acid. In some embodiments, at least two of the series of concentrations span about one order of magnitude, about 2 orders of magnitude, about 3 orders of magnitude, about 4 orders of magnitude, about 5 orders of magnitude, about 6 orders of magnitude, about 7 orders of magnitude, or more. In some embodiments, the series of concentrations includes at least two, at least 3, at least 4, at least 5, or six concentrations selected from about $10^{-10}$ M, about $10^{-11}$ M, about $10^{-12}$ M, about $10^{-13}$ M, about $10^{-14}$ M, about $10^{-15}$ M, and about $10^{-16}$ M.

In some embodiments, a series of standardized mixture of reagents is provided comprising one or more positive controls, e.g., one or more positive controls disclosed herein. In some preferred embodiments, a positive control for an allele of a target nucleic acid can be provided in a series of serially-diluted standardized mixtures at serial dilutions, e.g., at about 2-fold, at about 5-fold, at about 10-fold, at about 20-fold, etc., serial dilutions. In some embodiments, the positive control is at a series of concentrations relative to a competitive template for the target nucleic acid. In such embodiments, the series can provide amounts of positive control to amounts of competitive template in a series of ratios.

In some embodiments, one or more of the series of standardized mixtures can allow for detection with one or more of the sensitivities, one or more of the accuracies, one of more of the detection limits, and/or with more or more of the coefficients of variation taught herein, over various ranges of orders of magnitude, e.g., any of the orders of magnitude discussed herein.

III. Compositions for Assessing Nucleic Acid

Another aspect of the instant invention relates to compositions for assessing a nucleic acid in a sample, for example, compositions comprising a standardized mixture or a series of serially-diluted standardized mixtures, e.g., as described above, including reagents and kits for assessing alleles and/or allelic frequency and detecting false positives and/or false negatives. Other aspects of the instant invention relate to databases, e.g., databases comprising data obtained using some embodiments of the methods and/or compositions of the present invention.

A. Kits

Any of the compositions, including reagents, competitive templates, primers, detection moieties, arrays, common capture moieties, and/or positive controls, disclosed herein can be provided as a kit. For example, a kit may comprise a first standardized mixture of competitive templates for a number of target nucleic acids and a second standardized mixture of positive controls corresponding to at least some of the same target nucleic acids. The two standardized mixtures may be used in conduction with each other for assessing one or more of the target nucleic acids in a sample with quality controls for false positives and/or false negatives.

The compositions and/or combinations of compositions used in a kit of the instant invention can allow for detection with one or more of the sensitivities, one or more of the accuracies, one or more of the detection limits, and/or with more or more of the coefficients of variation taught herein.

One or more such compositions can be provided in a container along with instructions and the like. For example, the kit may comprise a manual providing reaction conditions and appropriates amounts of various reagents to use in conducting one or more methods provided herein. In some embodiments, the kit can be used for implementing, monitoring, and/or enforcing quality control in diagnostic applications, e.g., molecular diagnostic testing, including, e.g., loss of heterozygosity. In some embodiments, the kit further comprises software capable of analyzing data generated from the kit.

B. Database of Numerical Values

Another aspect of the instant invention is directed to a database. For example, some embodiments provide a database of numerical values corresponding to amounts of a first nucleic acid in a number of samples. In some embodiments, the first nucleic acid comprises an allele.

In preferred embodiments, the numerical values are directly comparable between the number of samples. For example, in some embodiments, the numerical values are directly comparable between at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some embodiments, direct comparison involves comparing the numerical values to one another without using a bioinformatics resource. In some embodiments, a bioinformatics resource, e.g., a simple bioinformatics resource, can be used.

For example, measured amounts of nucleic acid can be obtained by any methods of the various embodiments of the instant invention and/or described herein to provide numerical values. For example, a nucleic acid can be assessed relative to a known number of competitive template molecules for the nucleic acid that have been combined into a standardized mixture. Such embodiments can facilitate the reporting of nucleic acid measurement as a numerical value. For example, the numerical value can be obtained by calculating a "ratio of ratios" as described above. In some specific embodiments, each value in the database has been made relative to an internal standard within a standardized mixture of internal standards.

In preferred embodiments, numerical values correspond to numbers of molecules of a given nucleic acid in a sample or allele of a given nucleic acid. In some embodiments, numerical values can be provided in units of (molecules of a first nuclei acid)/(molecules of a second nucleic acid), e.g., where the second nucleic acid serves as a reference nucleic acid. In a specific embodiment, measurements are provided in units of (cDNA molecules of a first nucleic acid)/($10^6$ cDNA molecules of a second nucleic acid). Numerical values in some embodiments, for example, may correspond to less than about 1,000 molecules of a nucleic acid in a sample, e.g., to about 800, at to about 600, or to about 400 molecules. In some embodiments, numerical values may correspond to less than about 100 molecules (e.g., to about 60 molecules), less than about 10 molecules (e.g., to about 6 molecules), or less than about 1 molecule of a nucleic acid in a sample. In some embodiments, numerical values may correspond to less than about 10,000,000, less than about 5,000,000, less than about 1,000,000, less than about 500,000, less than about 100,000, less than about 50,000, less than about 10,000, less than about 8,000, less than about 6,000, less than about 5,000, or less than about 4,000 molecules of a nucleic acid in a sample.

The database of the instant invention can comprise numerical values varying over a range. For example, in some embodiments, numerical values can vary over a range of less than about one order of magnitude, more than about one order of magnitude, or more than about 2 orders of magnitude. In some embodiments, numerical values of measured amounts of different nucleic acids, e.g., mRNA levels expressed from two or more different genes, can vary over a range of about 3 or more orders of magnitude, about 4 or more orders of magnitude, about 5 or more orders of magnitude, about 6 or more orders of magnitude, or about 7 or more orders of magnitude, e.g., spanning the about 7-log range of gene expression of about $10^{-3}$, about $10^{-2}$, about 0.1, about 1, about 10, about $10^2$, about $10^3$, and about $10^4$ copies/cell. In some embodiments, numerical values of measured amounts of different nucleic acids can vary over a range of about 8 or more, about 9 or more, or about 10 or more orders of magnitude, e.g., spanning an about 10-log range of gene expression of about $10^{-3}$, about $10^{-2}$, about 0.1, about 1, about 10, about $10^2$, about $10^3$, about $10^4$, about $10^5$, or about $10^6$ copies/cell. Such ranges of gene expression may be important in detecting agents of biological warfare and/or pathogenic agents, e.g., certain viruses, and the like, that may be present in very small concentrations in a sample.

In some embodiments, numerical values of the database correspond to less than about a two-fold difference in a nucleic acid between 2 of the samples. In some embodiments, the numerical values correspond less than about a one-fold difference, less than about an 80% difference, less than about a 50% difference, less than about a 30% difference, less than about a 20% difference, less than about a 10% difference, less than about a 5% difference, or less than about a 1% difference.

Without being limited to a given hypothesis and/or theory, since the data in some embodiments is standardized against a common mixture of internal standard competitive templates, direct comparisons are possible. For example, as discussed above, in some embodiments, the numerical values are directly comparable between a number of samples, e.g., samples obtained from different subjects and/or from different species. In some embodiments the numerical values are directly comparable between a number of samples measured in different laboratories and/or at different times. In preferred embodiments, such comparisons are possible without the use of a calibrator sample (e.g., a non-renewable calibrator sample).

Two values can be descried as being "directly comparable" where, e.g., the numerical values of each describe the amounts relative to a common standard. As a readily understandable analogy, 10° C. is directly comparable to 50° C. as both values are provided relative to the boiling point of water (100° C.). Using some embodiments provided herein, the number of cDNA molecules representing a gene (or an allele of a gene) in a given sample is measured relative to its corresponding competitive template in a standardized mixture, rather than by comparing it to another sample. Use of a common standardized mixture can provide the common standard and can facilitate direct comparisons.

In contrast, using techniques such as real-time RT-PCR and/or microarray analysis (other than in combination with some embodiments of the instant invention), nucleic acids being measured scale differently. For example, differences in hybridization melting temperatures between cDNA with bound polynucleotides (microarrays) or fluorescent probes (real-time RT-PCR) cause measurements to scale differently. Consequently, relative amounts of different nucleic acids in a specimen and/or between specimen may not be directly comparable, e.g., it may not be possible to compare difference in expression among many genes in a sample. Further, real-time PT-PCR and/or microarray analysis measurements may not provide direct information as to the number of molecules of a nucleic acid present in a sample.

Assessed amounts may also be corrected for one or more sources of variation, e.g., in accordance with various embodiments of the teachings provided herein. In some embodiments, the values in the database show a coefficient of variation of less than about 50%, less than about 30%, less than about 25%, less than about 20%, less than about 15%, less than about 10%, less than about 5%, or less than about 1% between 2 of more samples. In some preferred embodiments, numerical values do not comprise a statistically significant number of false positives. In some preferred embodiments, numerical values do not comprise a statistically significant number of false negatives. In more preferred embodiments, numerical values do not comprise false positives and/or false negatives.

In some embodiments, the database further comprises numerical values corresponding to amounts of a number of other nucleic acid(s) in the samples, where said amounts are directly comparable. The number of other nucleic acids for which data is included in the database can be at least about 5, at least about 10, at least about 50, at least about 100, at least about 500, at least about 1,000, at least about 5,000, at least about 10,000, at least about 50,000, at least about 100,000, at least about 500,000, at least about 1,000,000, at least about 5,000,000 or at least about 10,000,000 other nucleic acids.

In some embodiments, the database of the instant invention can serve as a common databank, where measured amounts of nucleic acids (e.g. gene expression measurements) are reported as numerical values that allow for direct inter-experiment comparison. In preferred embodiments, the database establishes a continuously expanding virtual multiplex experiment (i.e., data from an ever-expanding number of nucleic acids, samples and/or specimens can be entered into a given database and compared directly to other data within the database). This can lead to synergistic increases in knowledge, e.g., knowledge regarding the relationship between gene expression patterns and phenotype and/or knowledge regarding allelic variation and phenotype.

More preferred embodiments of the instant invention can be used to provide a common language for gene expression. Gene expression may be measured at the mRNA, protein, or functional level, preferably at the mRNA level. For example, mRNA expression is regulated primarily by the number of transcripts available for translation. Because mRNA expression is related primarily to copy number, one is able to develop an internal standard for each gene and/or to establish a common unit for gene expression measurement. For example, in a multi-institutional study, data generated by methods discussed herein were sufficiently sensitive and reproducible to support development of a meaningful gene expression database, serving as a common language for gene expression.

Some embodiments provide a common language for gene expression across species. For example, primers can be identified that PCR amplify nucleic acids corresponding to both human and mouse genes, e.g., for at least about 20%, for at least about 30%, for at least about 50%, for at least about 80%, or for at least about 90% of genes common to human and mice. Primers can also be developed to obtain wider cross-species application, e.g., for amplifying nucleic acids corresponding to two or more different species. For example, in some embodiments, primers can identified that amplify nucleic acids corresponding to two or more of human, rat, pig, horse, sheep, monkey, plant, fruit fly, fish, yeast, bacterial and/or viral genes.

In some embodiments, the database is web-based. In some embodiments, the database invention finds use in experimental research, clinical diagnoses and/or drug development. For example, in some embodiments, the database can be used to advance studies on pathways of transcriptional control, and/or serve as a basis for mechanistic investigation. For example, bivariate analysis of individual gene expression numerical values for transcription factor genes and genes controlled by these transcription factors can improve understanding of gene expression regulation. In some embodiments, this can increase insight into control of gene expression, e.g., in normal and malignant cells.

B. Database of Numerical Indices

Some embodiments of the instant invention provide a database comprising numerical indices. The numerical indices can be obtained by mathematical computation of 2 or more numerical values, where the numerical values correspond to amounts of nucleic acids in a number of samples. In some embodiments, the numerical values correspond to amounts of an allele of a nucleic acid in a number of samples.

In preferred embodiments, the numerical indices are directly comparable between the samples. For example, in some embodiments, the numerical indices are directly comparable between at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples. In some embodiments, direct comparison involves comparing the numerical indices to one another without a bioinformatics resource. In some embodiments, a bioinformatics resource, e.g., a simple bioinformatics resource, can be used. In some specific embodiments, each measurement in the database has been made relative to an internal standard within a standardized mixture of internal standards.

As discussed above, nucleic acid measurements can be reported as numerical values. The numerical values can be combined into numerical indices by mathematical computation to provide a numerical index, e.g., allowing mathematical interaction among the numerical values. For example, in some embodiments, a numerical index is calculated by dividing a numerator by a denominator, the numerator corresponding to the amount of one of 2 nucleic acids and the denominator corresponding to the amount the other of the 2 nucleic acids. In some embodiments, a numerical index is calculated by a series of one or more mathematical functions. For example, a numerical index may be calculated by a formula (gene 1+gene 2)/(gene 3−gene 4). A numerical index can be described as balanced e.g., where it is computed by a formula having equal numbers of numerical values in the numerator as in the denominator. Methods for obtaining numerical indices that indicate a biological state, e.g., that can act as biomarkers by correlating with a phenotype of interest, are detailed below.

In some embodiments, the numerical indices are directly comparable between a number of samples, e.g., samples obtained from different subjects and/or from different species. In some embodiments the numerical indices are directly comparable between a number of samples measured and/or enumerated in different laboratories and/or at different times.

In some embodiments, the database of the instant invention can serve as a common databank, where measured amounts of nucleic acids (e.g. gene expression measurements) are mathematically combined to provide numerical indices that allow for direct inter-experiment comparison. In preferred embodiments, the database establishes a continuously expanding multiplex experiment (i.e., data from an ever-expanding number of nucleic acids, samples and/or specimens can be used to calculate numerical indices that are entered into a given database and compared directly to other data within the database).

As discussed above, in some embodiments, any measured nucleic acid or combination of nucleic acids, including all measured nucleic acids, can be used as the reference gene and data calculated using a first reference nucleic acid can be re-calculated relative to that of another reference nucleic acid. In the case of numerical indices, the difference in value obtained after converting from one reference nucleic acid to another can depend on how many numerical values are in the numerator and how many are in the denominator. For example, in some embodiments, each numerical value in a numerical index may be converted to the new reference in calculating the index. In some embodiments, for example, where there are equal numbers of numerical values in the numerator and denominator, conversion to a new reference may have no effect on the relative numerical index between samples and/or specimen.

In the case of balanced numerical indices where numerical values correspond to gene expression measurements, the effect of a reference nucleic acid that varies in expression from one sample and/or specimen to another can be neutralized. This can also occur in doing bivariate analysis. In other embodiments, for example, where there are non-equal numbers of numerical values in the numerator and denominator, the relative numerical index between samples and/or specimen may change in accordance with a difference in relative numerical values for the reference nucleic acids between the samples and/or specimen.

In some embodiments, the database is web-based. In some embodiments, the database invention finds use in experimental research, clinical diagnoses and/or drug development. For example, in some embodiments, the database can be used to advance studies on pathways of transcriptional control, and/or serve as a basis for mechanistic investigation. For example, in some embodiments, at least one numerical index indicates a biological state. Numerical indices may correlate better with a given biological state, e.g., a given phenotype, than a numerical value corresponding to an individual nucleic acid (e.g., to an individual gene).

IV. Applications

Another aspect of the instant invention relates to methods of using numerical values and/or indices in research, diagnostic and/or other applications.

A. Identification of Biomarkers

In some embodiments, methods for obtaining numerical indices are provided. In preferred embodiments, the numerical index obtained indicates a biological state. A "biological state" as used herein can refer to a phenotypic state, for e.g., a clinically relevant phenotype or other metabolic condition of interest. Biological states can include, e.g., a disease phenotype, a predisposition or susceptibility to certain diseases; a therapeutic drug response or predisposition to such a response, an adverse drug response (e.g. drug toxicity) or a predisposition to such a response or sensitivity to certain treatments; a resistance to a drug, or a predisposition to showing such a resistance, etc. In preferred embodiments, the numerical index obtained can act as a biomarker, e.g., by correlating with a phenotype of interest. In some embodiments, the drug may be and anti-tumor drug. In preferred embodiments, use of embodiments of the instant invention described herein can provide personalized medicine.

In some embodiments, a method for obtaining a numerical index that indicates a biological state comprises providing 2 samples corresponding to each of a first biological state and a second biological state; measuring and/or enumerating an amount of each of 2 nucleic acids in each of the 2 samples; providing the amounts as numerical values that are directly comparable between a number of samples; mathematically computing the numerical values corresponding to each of the first and second biological states; and determining a mathematical computation that discriminates the two biological states.

First and second biological states as used herein correspond to two biological states of to be compared, such as two phenotypic states to be distinguished. Examples include, e.g., non-disease (normal) tissue vs. disease tissue; a culture showing a therapeutic drug response vs. a culture showing less of the therapeutic drug response; a subject showing an adverse drug response vs. a subject showing a less adverse response; a treated group of subjects vs. a non-treated group of subjects, etc.

A numerical index that discriminates a particular biological state, e.g., a disease or metabolic condition, can be used as a biomarker for the given condition and/or conditions related thereto. For example, in some embodiments, the biological state indicated can be at least one of an angiogenesis-related condition, an antioxidant-related condition, an apotosis-related condition, a cardiovascular-related condition, a cell cycle-related condition, a cell structure-related condition, a cytokine-related condition, a defense response-related condition, a development-related condition, a diabetes-related condition, a differentiation-related condition, a DNA replication and/or repair-related condition, an endothelial cell-related condition, a hormone receptor-related condition, a folate receptor-related condition, an inflammation-related condition, an intermediary metabolism-related condition, a membrane transport-related condition, a neurotransmission-related condition, a cancer-related condition, an oxidative metabolism-related condition, a protein maturation-related condition, a signal transduction-related condition, a stress response-related condition, a tissue structure-related condition, a transcription factor-related condition, a transport-related condition, and a xenobiotic metabolism-related condition.

For example, in specific embodiments, numerical indices that indicate lung cancer (E. L. Crawford, K. A. Warner, S. A. Khuder et al., Biochem. Bioph. Res. Co. 293, 509-516 (2002); E. L. Crawford, S. A. Khuder, S. J. Durham et al., Cancer Res. 60, 1609-1618 (2000); J. P. DeMuth, C. M. Jackson, D. A. Weaver et al., Am. J. Respir. Cell Mol. Biol. 19, 18-24 (1998)), pulmonary sarcoidosis (M. G. Rots, R. Pieters. G. J. Peters et al., Blood 94, 3121-3128 (1999)) cystic fibrosis (J. T. Allen, R. A. Knight, C. A. Bloor and M. A. Spiteri, *Am. J. Respir. Cell. Mol. Biol.* 21, 693-700 (1999)) and chemoresistance in childhood leukemias (S. Mollerup, D. Ryberg, A. Hewer et al., *A. Cancer Res.* 59, 3317-3320 (1999)) have been identified. In other specific embodiments, antioxidant and xenobiotic metabolism enzyme genes have been evaluated in human buccal epithelial cells; micro-vascular endothelial cell gene expression has been associated with scleroderma progression; membrane transport genes expression has been studied in rat congestive heart failure models; immune resistance has been studied in primary human tissues; transcription control of hormone receptor expression has been studied; and gene expression patterns have been associated with carboplatin and/or taxol resistance in ovarian carcinoma and with gemcitabine resistance in multiple human tumors. Other specific examples include, e.g., identification of numerical indices for predicting responsiveness of colon cancer to 5-FU and for indicating one or more different stages of bladder carcinoma. Embodiments of inventions described herein can accelerate discovery of associations between gene expression patterns and biological states of interest, leading to better methods for preventing, diagnosing and treating various conditions.

Measuring nucleic acid amounts may be performed by any methods known in the art and/or described herein. Preferably, the method used can measure and/or enumerate less than about 10,000 molecules, less than about 8,000, less than about 6,000, or less than about 4,000, preferably less than about 1,000, less than about 800, less than about 600, or less than about 400 molecules, of a given nucleic acid in a given sample. In some embodiments, the measurements correspond to gene expression measurements, e.g., levels of mRNA transcripts can be measured. In preferred embodiments, transcript levels, in particular, transcript levels of 2 or more genes, can be used to indicate a biological state. For example, microarray analysis has identified gene sets that are associated with disease states and/or drug responses (D. A. Wigle, I. Jurisica, N. Radulovich et al., Cancer Res. 62, 3005-3008 (2002); M. E. Garber, O. G. Troyanskaya. K. Schluens et al., Proc. Natl. Acad. Sci. USA 98, 13784-13789 (2001); A. Bhattacharjee, W. G. Richards, J. Staunton et al., Proc. Natl. Acad. Sci. USA 98, 13790-13795 (2001); I. Hedenfalk, D. Duggan, Y. Chen et al., New Engl. J. Med. 344, 539-548 (2001); T. Sorlie, C. M. Perou, R. Tibshirani et al., Proc. Natl. Acad. Sci. USA 98, 10869-10874 (2001); C. M. Perou, S. S. Jeffrey, M. van de Rijn et al., Proc. Natl. Acad. Sci. USA 96, 9212-9217 (1999)). Providing the measured and/or enumerated amounts as numerical values is preferably accomplished by methods described herein, where the numerical values are directly comparable for a number of samples used.

In some embodiments, one or more of the nucleic acids to be measured are associated with one of the biological states to a greater degree than the other(s). For example, in some preferred embodiments, one or more of the nucleic acids to be evaluated is associated with a first biological state and not with a second biological state. A nucleic acid may be said to be "associated with" a particular biological state where the nucleic acid is either positively or negatively associated with the biological state. For example, a nucleic acid may be said to be "positively associated" with a first biological state where the nucleic acid occurs in higher amounts in a first biological state compared to a second biological state. As an illustration, genes highly expressed in cancer cells compared to non-cancer cells can be said to be positively associated with cancer. On the other hand, a nucleic acid present in lower amounts in a first biological state compared to a second biological state can be said to be negatively associated with the first biological state.

The nucleic acid to be measured and/or enumerated may correspond to a gene associated with a particular phenotype. The sequence of the nucleic acid may correspond to the transcribed, expressed, and/or regulatory regions of the gene (e.g., a regulatory region of a transcription factor, e.g., a transcription factor for co-regulation).

For example, in some embodiments, the amounts of different alleles of a given target nucleic acid can be assessed, where the different alleles are associated with particular phenotypes. In preferred embodiments, the allelic variations assessed provide numerical values and/or numerical indices that indicate a biological state. For example, point mutations responsible for and/or associated with conditions such as cystic fibrosis, sickle cell disease, Huntington's Chorea, Factor V Leiden coagulopathy, and the like, can be assessed. For example, different cystic fibrosis alleles can be quantitated and/or used to provide a numerical index wherein the numerical index indicates the disease.

In some embodiments, the alleles assessed indicate a cancer-related condition. For example, some types of cancer are associated with mutations in one or more alleles, e.g., a mutation in a cancer suppressive gene and/or in a DNA repair enzyme gene. In addition, part or all of a chromosome may be lost in some cancer cells, resulting in an apparent loss of heterozygousity. In still some embodiments, the alleles assessed comprise breakpoint mutations that indicate a neoplasia-related condition, i.e., breakpoint lesions associated with neoplasias.

In some embodiments, expressed amounts of more than 2 genes are measured and used in to provide a numerical index indicative of a biological state. For example, in some cases, expression patterns of about 50 to about 100 genes are used to characterize a given phenotypic state, e.g., a clinically relevant phenotype. See, e.g., Heldenfalk, I. et al. NEJM 344: 539, 2000. In some embodiments of the instant invention, expressed amounts of at least about 5 genes, at least about 10 genes, at least about 20 genes, at least about 50 genes, or at least about 70 genes may be measured and used to provide a numerical index indicative of a biological state. In some embodiments of the instant invention, expressed amounts of less than about 90 genes, less than about 100 genes, less than about 120 genes, less than about 150 genes, or less than about 200 genes may be measured and used to provide a numerical index indicative of a biological state. Specific examples of several of these embodiments include, e.g., identification of gene expression patterns associated with lung cancer (Crawford, E. L. et al. Normal bronchial epithelial cell expression of glutathione transferase P1, glutathione transferase M3, and glutathione peroxidase is low in subjects with bronchogenic carcinoma. Cancer Res., 60: 1609-1618, 2000; DeMuth, et al., The gene expression index c-myc×E2F-1/p21 is highly predictive of malignant phenotype in human bronchial epithelial cells. Am. J. Respir. Cell Mol. Biol., 19: 18-24, 1998); pulmonary sarcoidosis (Allen, J. T., et al., Enhanced insulin-like growth factor binding protein-related protein 2 (connective tissue growth factor) expression in patients with idiopathic pulmonary fibrosis and pulmonary sarcoidosis. Am. J. Respir. Cell Mol. Biol., 21: 693-700, 1999); cystic fibrosis (Allen, et al, supra); and chemoresistance in childhood leukemias (Rots, M. G., et al., Circumvention of methotrexate resistance in childhood leukemia subtypes by rationally designed antifolates. Blood, 94(9): 3121-3128, 1999; Rots, M. G., et al., mRNA expression levels of methotrexate resistance-related proteins in childhood leukemia as determined by a competitive template-based RT-PCR method. Leukemia, 14:2166-2175 (2000)).

Mathematically computing numerical values can refer to using any equation, operation, formula and/or rule for interacting numerical values, e.g., a sum, difference, product, quotient, log power and/or other mathematical computation. As described above, in some embodiments, a numerical index is calculated by dividing a numerator by a denominator, where the numerator corresponds to an amount of one nucleic acid and the denominator corresponds to an amount the another nucleic acid. In preferred embodiments, the numerator corresponds to a gene positively associated with a given biological state and the denominator corresponds to a gene negatively associated with the biological state. In some embodiments, more than one gene positively associated with the biological state being evaluated and more than one gene negatively associated with the biological state being evaluated can be used. For example, in some embodiments, a numerical index can be derived comprising numerical values for the positively associated genes in the numerator and numerical values for an equivalent number of the negatively associated genes in the denominator. As mentioned above, in such balanced numerical indices, the reference nucleic acid numerical values cancel out. An example of a balanced numerical index includes a numerical index for predicting anti-folate resistance among childhood leukemias. Rots, M. G., Willey, J. C., Jansen, G., et al. (2000) mRNA expression levels of methotrexate resistance-related proteins in childhood leukemia as determined by a standardized competitive template-based RT-PCR method. Leukemia 14, 2166-2175. In some embodiments, balanced numerical values can neutralize effects of variation in the expression of the gene(s) providing the reference nucleic acid(s). In some embodiments, a numerical index is calculated by a series of one or more mathematical functions.

Determining which mathematic computation to use to provide a numerical index indicative of a biological state may be achieved by any methods known in the arts, e.g., in the mathematical, statistical, and/or computational arts. In some embodiments, determining the mathematical computation involves a use of software. For example, in some embodiments, a machine learning software can be used.

In some embodiments, more than one sample corresponding to each biological state can be provided. For example, at least about 5 samples, at least about 10 samples, at least about 50 samples, at least about 100 samples, at least about 500 samples, at least about 1,000 samples, at least about 5,000 samples, at least about 10,000 samples, at least about 50,000 samples, at least about 100,000 samples, at least about 500,000 samples, at least about 1,000,000 samples, at least about 5,000,000 samples, or at least about 10,000,000 samples may be provided.

In some embodiments, more than 2 biological states can be compared, e.g., distinguished. For example, in some embodiments, samples may be provided from a range of biological states, e.g., corresponding to different stages of disease progression, e.g., different stages of cancer. Cells in different stages of cancer, for example, include a non-cancerous cell vs. a non-metastasizing cancerous cell vs. a metastasizing cell from a given patient at various times over the disease course. Cancer cells of various types of cancer may be used, including, for example, a bladder cancer, a bone cancer, a brain tumor, a breast cancer, a colon cancer, an endocrine system cancer, a gastrointestinal cancer, a gynecological cancer, a head and neck cancer, a leukemia, a lung cancer, a lymphoma, a metastases, a myeloma, neoplastic tissue, a pediatric cancer, a penile cancer, a prostate cancer, a sarcoma, a skin cancer, a testicular cancer, a thyroid cancer, and a urinary tract cancer. In preferred embodiments, biomarkers can be developed to predict which chemotherapeutic agent can work best for a given type of cancer, e.g., in a particular patient.

A non-cancerous cell may include a cell of hematoma and/or scar tissue, as well as morphologically normal parenchyma from non-cancer patients, e.g., non-cancer patients related or not related to a cancer patient. Non-cancerous cells may also include morphologically normal parenchyma from cancer patients, e.g., from a site close to the site of the cancer in the same tissue and/or same organ; from a site further away from the site of the cancer, e.g., in a different tissue and/or organ in the same organ-system, or from a site still further away e.g., in a different organ and/or a different organ-system.

Numerical indices obtained can be provided as a database. Numerical indices and/or databases thereof can find use in diagnoses, e.g. in the development and application of clinical tests, as described below.

B. Diagnostic Applications

In some embodiments of the instant invention, a method of identifying a biological state is provided. In some embodiments, the method comprises measuring and/or enumerating an amount of each of 2 or more nucleic acids in a sample, providing the amounts as numerical values; and using the numerical values to provide a numerical index, whereby the numerical index indicates the biological state. In some embodiments, one or more of the nucleic acids assessed comprise an allele.

A numerical index that indicates a biological state can be determined as described above in accordance with various embodiments of the instant invention. The sample may be obtained from a specimen, e.g., a specimen collected from a subject to be treated. The subject may be in a clinical setting, including, e.g., a hospital, office of a health care provider, clinic, and/or other health care and/or research facility. Amounts of nucleic acid(s) of interests in the sample can then be measured and/or enumerated.

Assessing nucleic acid amounts may be performed by any methods described herein. Preferably, the method used can measure and/or enumerate less than about 10,000 molecules, less than about 8,000, less than about 6,000, or less than about 4,000, preferably less than about 1,000, less than about 800, less than about 600, or less than about 400 molecules, of a given nucleic acid in a given sample. In cases where several genes are to be measured in a sample and/or specimen, preferred embodiments can be practiced using small amounts of starting cellular material, e.g., using the amounts of material obtained from a diagnostic biopsy sample, e.g., by the methods described in more detail above and/or as known in the art. In more preferred embodiments, more than one gene can be evaluated at the same time, and in highly preferred embodiments, where a given number of genes are to be evaluated, expression data for that given number of genes can be obtained simultaneously. For example, in some embodiments, data obtained from primary lung cancer tissue can be assayed. By comparing the expression pattern of certain genes to those in a database, a chemotherapeutic agent a tumor with that gene expression pattern would most likely respond to can be determined.

In some embodiments, methods of the invention can be used to evaluate simultaneously both an exogenous reporter gene and an endogenous housekeeping gene, such as GAPDH RNA in a transfected cell, either in vitro or in vivo. In some embodiments, for example, relative amounts of exogenous cystic fibrosis transmembrane conductance regulator (CFTR) gene per cell can be measured. Although numerous different mutations in the CFTR gene have been reported to be associated with disease, the most common disease-associated mutation is a 3 base deletion at position 508. It is possible to prepare primers that result in amplification of one or other of the abnormal 508 deleted gene or the normal CFTR gene using described methods, e.g., Cha, R. S., Zarbl, H., Keohavong, P., Thilly, W. G., match amplification mutation assay (MAMA): application to the c-Ha ras gene, PCR methods and applications, 2:14-20 (1992). These can be used with certain embodiments of the present invention to measure amounts of exogenous normal CFTR nucleic acid and/or amounts of endogenous mutant CFTR gene.

Similarly, in some embodiments, methods of the invention can be used to quantify exogenous normal dystrophin gene in the presence of mutated endogenous gene. In the case of dystrophin, the disease results from relatively large deletions. Using primers that span the deleted region, one can selectively amplify and quantitate expression from a transfected normal gene and/or a constitutive abnormal gene for dystrophin. As will be appreciated by those in the art, other genes associated with other diseases and/or conditions can also be evaluated in similar manner.

In some embodiments, positive controls are used, e.g., to detect false negatives and/or false positives of a nucleic acid in diagnostic applications. For example, a positive control of each of two alleles of a target nucleic acid may be used to detect and correct for false positives and/or false negatives, providing corrected values for the amounts of one or both of the alleles. The corrected value can be used to provide a numerical value or numerical index that indicates a biological state. Such techniques can facilitate implementing, monitoring, and/or enforcing quality control in diagnostic applications, e.g., molecular diagnostic testing. E.g., diagnostic testing for any condition provided herein, including, e.g., loss of heterozygosity in cancer-related conditions can be quality controlled. In preferred embodiments, the methods provided herein allow quality control in making the diagnosis, e.g., as may be required by the FDA and/or CDA.

EXAMPLES

Example I

The Following Example Illustrates Assessing Allelic Frequency of an Artificially-Synthesized Catalase Gene Mutation, in Accordance with Some Embodiments of the Invention A pair of primers is prepared for PCR amplification of the catalase gene. The reverse primer is designed to incorporate two different single basepair mutations into the sequence of the normal catalase gene. The mutations are introduced in a region other than where a gene-specific oligonucleotide will hybridize amplified product, and other than the sequence homologous to competitive template for the catalase gene. Large amounts of catalase nucleic acid and mutated catalase nucleic acid is obtained by PCR amplification and the amounts are quantitated.

In a sample comprising amounts of catalase nucleic acid, mutated catalase nucleic acid and genomic β-actin DNA, the β-actin DNA can be used to "balance" the sample against a standardized mixture comprising a known amount of competitive template for β-actin, as described in detail herein. Briefly, the sample is serially diluted, and the sample dilution providing an amount of β-actin DNA within 10-fold of the amount of its competitive template in the standardized mixture is used. The sample dilution is mixed with the standardized mixture, which also comprises a known concentration of a competitive template for catalase, to provide a master mixture.

The master mixture is subjected to PCR amplifications. The catalase nucleic acid, mutated catalase nucleic acid and the competitive template for catalase are co-amplified in one tube. The β-actin nucleic acid and its competitive template can be co-amplified in the same tube or in a different tube prepared using the same master mixture.

Amplified products of β-actin nucleic acid and its competitive template as well as amplified products of catalase nucleic acid, mutated catalase nucleic acid and the competitive template for catalase are simultaneously applied to a solid phase medium having β-actin-specific and catalase-specific oligos coupled thereto at different positions. Under conditions allowing hybridization, amplified products of catalase nucleic acid, mutated catalase nucleic acid and the competitive template for catalase are immobilized at one set of positions (e.g., positions 1 and 2) and amplified products of β-actin nucleic acid and its competitive template are immobilized at a different position (e.g., position A), by hybridizing to their respective complementary oligos. That is, one set of spots anchor the catalase products and another set of spots anchor the β-actin products.

Probes that distinguish amplified products of normal catalase nucleic acid (Cy5-labeled) from amplified products of the competitive template for catalase (Cy3-labeled) are added at position 1, while probes that distinguish amplified products of mutated catalase nucleic acid (Cy5-labeled) from amplified products of the competitive template for catalase (Cy3-labeled) are added at position 1. The ratio of Cy5/Cy3 fluorescence at each position is obtained.

Probes that distinguish amplified products of β-actin nucleic acid (Cy5-labeled) from its competitive template (Cy3-labeled) are added position A and the Cy5/Cy3 ratio obtained. The three ratios are used to provide allelic frequency.

Example II

The Following Example Provides Additional Details for Quantifying Catalase Gene using Arrays in Accordance with Some Embodiments of the Instant Invention One set of 70-mers were designed to hybridize to amplified product of both catalase target nucleic acid as well as amplified products of its competitive template. Another set of 70-mers were designed to hybridize amplified product of both β-actin reference nucleic acid and its competitive template. The 70-mers were spotted to slides using a SpotArray 24 (Perkin-Elmer). Probes were designed to be specific for amplified product of catalase or of its competitive target, or for amplified product of β-actin or of its competitive template; and 5' end-labeled with either Cy3 or Cy5 fluors. Probes designed to bind specifically to amplified products of catalase or to amplified product of β-actin were labeled with Cy5.

Probes designed to bind specifically to the competitive template for catalase or to the competitive template for β-actin were labeled with Cy3.

Catalase and β-actin cDNA was obtained from Universal Human Reference RNA (Stratagene). PCR products were generated by co-amplifying catalase with its competitive template and β-actin with its competitive template using a commercially available standardized mixture of the competitive templates (Gene Express, Inc.). A series of PCR reactions was performed with a 100-fold variation in the ratio of catalase cDNA to the competitive template for catalase in the standardized mixture.

Amplified products were hybridized to the custom arrays along and appropriate probes added in a humidified chamber for 1 hour at 37° C. Probes and amplified products bound to the array were detected and quantified using a ScanArray 4000 (Perkin-Elmer).

All values were calculated using signal intensity above background for each fluor, e.g., using the following ratio of ratios: (catalase native template-Cy5/catalase competitive template-Cy3)/(β-actin native template-Cy5/β-actin competitive template-Cy3)}

For comparison purposes, aliquots of the same amplified products were electrophosed on an Agilent 2100 Bioanalyzer (Agilent Technologies) and quantified using the area under the curves (a previously validated method.) The data obtained was compared with data obtained using the arrays.

Table II illustrates the data obtained using array measurement and that obtained using Agilent measurements. Average expression values (in units of catalase cDNA molecules/$10^6$ β-actin cDNA molecules) for the array and the Bioanalyzer were $1.16 \times 10^3$ and $5.06 \times 10^2$ respectively. The CV1 was 9% for the array and 33% for the Agilent Bioanalyzer. Both had similar linear dynamic ranges of detection although the Agilent Bioanalyzer had a lower limit of detection.

Although the NT/CT ratios measured on the array are compressed compared to the expected NT/CT ratios and with those measured on the Agilent 2100 Bioanalyzer, the measurement of catalase gene expression seen on the array is comparable to that measured on the Agilent 2100. The effect is improvement in effective sensitivity to 100%.

Example III

The Following Example Provides Additional Details of an Overall Process of Evaluating Gene Expression Measurements According to Some Embodiments of the Instant Invention Materials 1. Standardized RT-PCR reagents, including primers and standardized mixtures are purchased from Gene Express, Inc. (GEI, Toledo, Ohio).

2. Buffer for Idaho Rapidcycler air thermocycler: 500 mM Tris-HCl, pH 8.3, 2.5 µg/L, BSA, 30 mM $MgCl_2$ (Idaho Technology, Inc., Idaho Falls, Id.).

3. Buffer for block thermocyclers, Thermo 10 X, 500 mM KCl, 100 mM Tris-HCl, pH 9.0, 1.0% Triton X-100 (Promega, Madison, Wis.).

4. Taq polymerase (5 U/µL), Moloney Murine Leukemia Virus (MMLV) reverse transcriptase, MMLV RT 5X first strand buffer: 250 mM Tris-HCl, pH 8.3, 375 mM KCl, 15 mM $MgCl_2$, 50 mM dithiothreitol, oligo dT primers, Rnasin, pGEM size marker, and deoxynucleotide triphosphates (dNTPs) also are obtained from Promega.

5. TriReagent is obtained from Molecular Research Center, Inc. (Cincinnati, Ohio).

6. Ribonuclease (Rnase)-free water and TOPO TA cloning kits are obtained from Invitrogen (Carlsbad, Calif.). The quality of the RNase-free water can be important for the efficient extraction of intact RNA. For example, inadequate DEPC Quantification of Catalase relative to β-actin in a Sample Serially Diluted Relative to a SMIS containing a known number of copies of each gene.

| | Array Measurements | | | | | | | | |
|---|---|---|---|---|---|---|---|---|---|
| Expected NT/CT | Ave. ACTB NT[1] | Ave. ACTB CT | Ave. ACTB NT/CT | ACTB NT molecules | Ave. CAT NT | Ave. CAT CT | Ave. CAT NT/CT | CAT NT molecules | CAT/$10^6$ ACTB[2] |
| 10.00 | 2995 | 4100 | 0.71 | 4.26E+05 | 638 | 825 | 0.77 | 4.62E+02 | 1.08E+03 |
| 6.00 | 1032 | 2238 | 0.42 | 2.52E+05 | 380 | 777 | 0.48 | 2.88E+02 | 1.14E+03 |
| 3.00 | 1101 | 2686 | 0.41 | 2.46E+05 | 351 | 891 | 0.43 | 2.58E+02 | 1.05E+03 |
| 1.00 | 754 | 4451 | 0.18 | 1.08E+05 | 236 | 1008 | 0.23 | 1.38E+02 | 1.28E+03 |
| 0.33 | 620 | 8159 | 0.08 | 4.80E+04 | 159 | 1665 | 0.1 | 6.00E+01 | 1.25E+03 |
| 0.17 | 465 | 8910 | 0.05 | 3.00E+04 | 152 | 1146 | 0.13 | 7.80E+01 | 2.60E+03 |
| 0.10 | 238 | 2341 | 0.12 | 7.20E+04 | 204 | 2518 | 0.08 | 4.80E+01 | 6.67E+02 |
| | | | | | | | Ave.[3] | 2.41E+02 | 1.16E+03 |
| | | | | | | | SD | 1.54E+02 | 1.00E+02 |
| | | | | | | | CV1 | 63.80 | 8.65 |

| | Agilent Measurements | | | | | | | | |
|---|---|---|---|---|---|---|---|---|---|
| Expected NT/CT | ACTB NT[4] | ACTB CT | ACTB NT/CT | ACTB NT molecules | CAT NT | CAT CT | CAT NT/CT | CAT NT molecules | CAT/$10^6$ ACTB |
| 10.00 | 383.6 | 7.5 | 38.9 | 2.33E+07 | 163.9 | 8.1 | 14.2 | 8.52E+03 | 3.65E+02 |
| 6.00 | 327.4 | 17 | 14.8 | 8.88E+06 | 195.3 | 18.9 | 7.3 | 4.38E+03 | 4.93E+02 |
| 3.00 | 329.3 | 34.4 | 7.3 | 4.38E+06 | 124.4 | 31.5 | 2.8 | 1.68E+03 | 3.84E+02 |
| 1.00 | 180.9 | 97 | 1.4 | 8.40E+05 | 84.6 | 55.8 | 1.1 | 6.60E+02 | 7.86E+02 |
| 0.33 | 93.5 | 190.5 | 0.4 | 2.40E+05 | 27.7 | 81.3 | 0.2 | 1.20E+02 | 5.00E+02 |
| 0.17 | 52.6 | 204.8 | 0.2 | 1.20E+05 | 12.6 | 80.5 | 0.1 | 6.00E+01 | 5.00E+02 |
| 0.10 | 23 | 194.2 | 0.1 | 6.00E+04 | 6.4 | 89.4 | 0.05 | 3.00E+01 | 5.00E+02 |
| | | | | | | | Ave. | 3.07E+03 | 5.06E+02 |
| | | | | | | | SD | 3.46E+03 | 1.68E+02 |
| | | | | | | | CV1 | 112.60 | 33.29 | treatment and/or inadequate removal of DEPC after treatment can inhibit reverse transcription and PCR.

7. GigaPrep plasmid preparation kits are purchased from Qiagen (Texas).

8. Caliper AMS 90SE chips are obtained from Caliper Technologies, Inc. (Mountain View, Calif.).

9. DNA purification columns are obtained from QiaQuick (Qiagen, Valencia, Calif.).

RNA Extraction and Reverse Transcription

RNA Extraction: Cell suspensions can be pelleted, the supernatant poured off, and the pellet dissolved in TriReagent and extract (according to manufacturer's instructions and previously described methods, see, e.g., Bustin, S. A. (2000) Absolute quantification of mRNA using real-time reverse transcription polymerase chain reaction assays. *J. Mol. Endorinol.* 25, 169-193. The RNA pellet can be stored under ethanol at −80° C., or suspended in RNAse free water and frozen at −80° C. It may be stored in this condition for years. The quality of the RNA can be evaluated on an Agilent 2100 using the RNA chip, according to manufacturer's instructions.

Reverse Transcription: 1 µg total RNA can be reverse transcribed using MMLV RT and an oligo dT primer as previously described. See, e.g., Willey, J. C., Coy, E. L., Frampton, M. W., et al. (1997) Quantitative RT-PCR measurement of cytochromes p450 1A1, 1B1, and 2B7, microsomal epoxide hydrolase, and NADPH oxidoreductase expression in lung cells of smokers and non-smokers. *Am. J. Respir. Cell Mol. Biol.* 17, 114-124. For small amounts of RNA (e.g. less than about 100 ng), the efficiency of reverse transcription may be improved with using Sensiscript™ rather than MMLV reverse transcriptase, e.g., efficient reverse transcription may be obtained about 50 ng of RNA with Sensiscript™. The reaction can be incubated at 37° C. for 1 h.

Synthesis and Cloning of Competitive Templates

Internal standard competitive templates (CTs) can be constructed based on previously described methods. See, e.g., Willey, J. C., Crawford, E. L., and Jackson, C. M. (1998) Expression measurement of many genes simultaneously by quantitative RT-PCR using standardized mixtures of competitive templates. *Am. J. Respir. Cell Mol. Biol.* 19, 6-17; Crawford, E. L., Peters, G. J., Noordhuis, P., et al. (2001) Reproducible gene expression measurement among multiple laboratories obtained in a blinded study using standardized RT (StaRT)-PCR. *Mol. Diagn.* 6, 217-225; and/or Celi, F. S., Zenilman, M. E., and Shuldiner, A. R. (1993) A rapid and versatile method to synthesize internal standards for competitive PCR. *Nucleic Acids Res.* 21, 1047.

Native Template Primer Design

Before a CT for a gene is constructed, a primer pair can be designed that amplifies (preferably, efficiently amplifies) native cDNA corresponding to the expressed gene. For example, primers can be designed with one or more of the following characteristics: (1) an ability to amplify from about 200 to about 850 bases of the coding region of genes of interest; (2) an annealing temperature of about 58° C. (tolerance of +/−1° C.). Primer 3.1 software (Steve Rozen, Helen J. Skaletsky, 1996, 1997) Primer 3 can be used to design the primers (code available at http://www-genome.wi.net.edu/genome_software/other/primer3.html) in some embodiments. Primers were initially designed using Primer 3.1 software to amplify from about 200 to about 800 bases of the coding region of targeted genes with an annealing temperature of about 58° C. (tolerance of +/− about 1° C.). This allowed the PCR reactions in this example to be run under identical or nearly identical conditions and further allows for automation and high throughput applications, including microfluidic capillary gel electrophoresis. For example, primer sequences and Genbank accession numbers for genes certain genes are available at www.geneexpressinc.com. Primers can also be designed to amplify from about 20 to about 2,000 bases, in other examples.

Native Template Primer Testing

Designed primers can be synthesized and used to amplify native template of cDNA corresponding to the gene(s) of interest. The presence of a single strong band after 35 cycles of PCR can verify that the primers are sufficiently efficient and/or specific for some embodiments. For example, primers can be tested using reverse transcribed RNA from a variety of tissues and/or cDNA clones known to represent the gene(s) of interest. In some embodiments, primer pairs that fail to amplify the target gene in any tissue or individual cDNA clone, e.g., less than about 10% of the time, can be redesigned and the process repeated.

Competitive Template Primer Design

Figure 23:
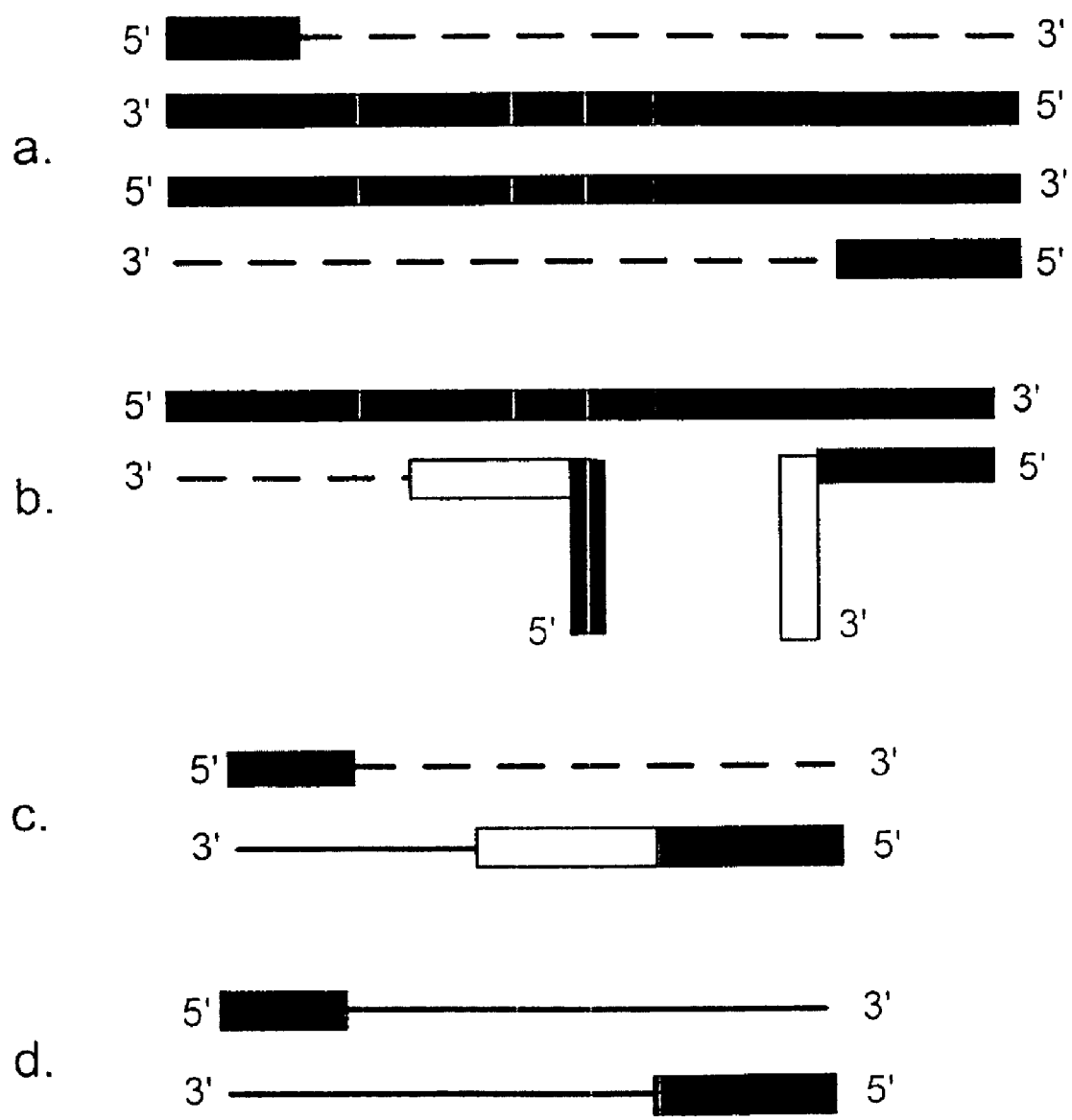
FIG. 23 illustrates a method for designing competitive template for use in some embodiments of the instant invention.

A CT primer can be prepared according to previously described methods and/or as illustrated in FIG. 23. FIG. 23a illustrates Forward (striped bar) and reverse (black bar) primers (approx 20 bp in length) that span a 150-850 bp region can be used to amplify the native template (NT) from cDNA. Taq polymerase can synthesize DNA from these primers (dashed lines) using the NT.

FIG. 23b illustrate that after testing that native template primers work, a CT primer can be designed to be about 40 bp primer with the sequence for the reverse primer (black bar) at the 5' end, and a 20 bp sequence homologous to an internal native template sequence (white bar) at the 3' end, collinear with the reverse primer sequence. The 3' end of this 40 bp primer can be designed to be homologous to a region about 50 to about 100 bp internal to the reverse primer. The 5' end of this about 40 bp primer can hybridize to the region homologous to the reverse primer, while the 3' end can hybridize to the internal sequence. Furthermore, Taq polymerase can synthesize DNA using the primers bound at the 3' end (dashed line) and not the primer bound at the 5' end.

FIG. 23c illustrates that in the next PCR cycle, the DNA newly synthesized using the about 40 bp primer hybridized to the internal sequence can be bound to forward primer (striped bar), and a homologous strand can be synthesized. FIG. 23d illustrates that this can generate a double stranded CT with the reverse primer sequence about 100 bp closer to the forward primer than occurs naturally in the NT. See, e.g., Chomczynski, P. and Sacchi, N. (1993) Single-step method of RNA isolation by acid guanidinium thiocyanate-phenol-chloroform extraction. *Anal. Biochem.* 62, 156-159; Celi, F. S., Zenilman, M. E., and Shuldiner, A. R. (1993) A rapid and versatile method to synthesize internal standards for competitive PCR. *Nucleic Acids Res.* 21, 1047).

Competitive Template Primer Testing

The prepared CT may be tested. For example, the CT primer can be paired with the designed forward primed and used to amplify CT from native cDNA. Before each competitive template in this example was constructed, each primer pair in this example was tested using reverse transcribed RNA from a variety of tissues or individual cDNA clones known to represent the gene of interest as a quality control. For primer pairs that failed (about 10% of the time), new ones were designed and the process repeated. For each gene, a competitive template primer (a fusion oligo of about 40 bp) then was prepared. The 3' end of each fusion primer consisted of an about 20 base sequence homologous to a region about 50 to about 100 bases 3' to the reverse primer. The 5' end was the 20 bp reverse primer.

Competitive Template-Internal Standard Production

For each of a number of genes to be assay, five 10 μL PCR reactions can be set up, using the designed NT forward primer and the CT primer, and amplified for 35 cycles. The products of the five PCR reactions can be combined, electrophoresed on a 3% NuSieve gel in 1X TAE, and the band of correct size cut from the gel and extracted using a QiaQuick method (Qiagen, Valencia, Calif.). The purified PCR products can be cloned into PCR 2.1 vector using TOPO TA cloning kits (Invitrogen, Carlsbad, Calif.) then can be transformed into HS996 (a T1-phage resistant variant of DH10B). After cloning, transformation, and colonies can be plating on LB plates containing X-Gal, IPTG, and carbenicillin and 3 isolated white colonies selected. Plasmid minipreps can be prepared, EcoRI digestion performed and the digested products electrophoresed on 3% SeaKem agarose. For those clones showing an insert based on EcoRI digestion, it can be confirmed that the insert is the desired one by sequencing the same undigested plasmid preparation using vector specific primers. The clones with homology to the correct gene sequence and having 100% match for the primer sequences can be used in large-scale CT preparation and can be included in standardized mixtures. For example, those that pass this quality control assessment can be used in the following steps.

Plasmids from each quality-assured clone then were prepared in quantities large enough (about 1.5 L) to allow for about 1 billion assays (approximately 2.6 mg). The plasmids were purified from the resultant harvested cells using the Qiagen GigaPrep kit. Plasmid yields were assessed using a Hoeffer DyNAQuant 210 fluorometer.

In this example, an aliquot of each plasmid preparation was again sequenced as a quality control. For each competitive template that passed the quality control steps outlined in this example, the sensitivity of the cloned CT and primers was assessed by performing PCR reactions on serial dilutions and determining the limiting concentration that still yielded a PCR product. In this example, only those preparations and primers that allow for detection of 60 molecules or less (e.g., a product obtained with $10^{-16}$ CT in 10 μl PCR reaction volume) were allowed to be included into standardized competitive template mixtures. In this example, most of the assays that were developed had a sensitivity of about 6 molecules or less (e.g., more than 80% of the CTs that were developed had a sensitivity of 6 molecules or less or $10^{-17}$ M CT).

Preparation of Standardized Mixtures

Plasmids from quality-assured preparations were mixed into competitive template mixtures representing either 24 or 96 genes. The concentration of the competitive templates in the 24 gene standardized mixtures were $4\times10^{-9}$ M for β-actin CT, $4\times10^{-10}$ M for GAPD (CT1), $4\times10^{-11}$ M for GAPD (CT2), and $4\times10^{-8}$ M for each of the other CTs in this example.

The 24 gene competitive template mixes can be linearized by NotI digestion prior to preparation of a series of serially-diluted standardized mixtures described below. For example, the mixes can be incubated with NotI enzyme at a concentration of 1 unit/μg of plasmid DNA in about 15 mL of buffer at 37° C. or 12-16 hours. Four linearized 24-gene competitive template mixes were combined in equal amounts to yield 96-gene competitive template mixes having concentrations of $10^{-9}$ M for β-actin, $10^{-10}$ M GAPD (CT1), $10^{-11}$ M GAPD (CT2), and $10^{-8}$ M for the other CTs. These mixes then can be serially diluted with a reference gene CT mix, e.g., comprising the $10^{-9}$ M β-actin, $10^{-10}$ M GAPDH (CT1), $10^{-11}$ M GAPDH (CT2) mix, yielding a stock series at concentrations of $10^{-9}$ M for β-actin, $10^{-11}$ M for GAPD CT1, $10^{-11}$ M for GAPD CT2, and $10^{-8}$, $10^{-9}$, $10^{-10}$, $10^{-11}$, $10^{-12}$, and $10^{-13}$ M for the other CTs used in this example.

These stock concentrations can be diluted 1,000-fold to provide working dilutions, e.g., to yield a series of six serially-diluted standardized mixtures (A-F) at concentrations of $10^{-12}$ M for β-actin, $10^{-13}$ M for GAPD CT1, $10^{-14}$ M for GAPD CT2, and $10^{-11}$ (A), $10^{-12}$ (B), $10^{-13}$ (C), $10^{-14}$ (D), $10^{-15}$ (E), and $10^{-16}$ M (F) for the other CTs used in this example.

The following illustrates use of a series of serially-diluted standardized mixtures, in accordance with some embodiments of the instant invention. In this example, "SMIS" refers to a standardized mixture of internal standards, prepared in accordance with embodiments of the instant invention.

A volume of cDNA sample (diluted to a level in balance with the amount of β-actin CT molecules in 1 μL of SMIS ($6\times10^5$) molecules) can be combined and mixed with an equal volume of the appropriate SMIS A-F, such that the NT/CT ratio for a nucleic acid being measured will be greater than about 1/10 and less than about 10/1. For example, if among previous samples, a gene has been expressed within a range of $10^1$-$10^3$ molecules/$10^6$ β-actin molecules, the gene will be measured using SMIS E. In contrast, if among previous samples, a gene has been expressed within a range of $10^5$-$10^7$ molecules/$10^6$ β-actin molecules, the gene will be measured using SMIS B. If the appropriate SMIS is not known for a particular gene in a sample from a particular type of tissue, expression can be measured using both SMIS C and E. This allows measurement over four orders of magnitude. For the rare samples that express the gene outside of the expected ranges, a follow-up analysis with the appropriate CT mix can be performed. For example, for the few genes expressed at very high or low level, analysis can be repeated with SMIS A or F.

A 1 μL volume of the cDNA/SMIS mixture can be used for each gene expression assay to be performed and can be combined with other components of the PCR reaction mixture (e.g., buffer, dNTPs, Mg++, Taq polymerase, $H_2O$). Tubes or wells can be prepared with a primer pair for a single gene to be measured. If products are to be analyzed by PE 310 device, the primers can be labeled with appropriate fluor. Aliquots of this PCR reaction mixture can be placed into individual tubes each containing primers for a single gene. Using this approach, the ratio of CT for every gene in the mixture relative to its corresponding NT in the cDNA is fixed simultaneously. When aliquots of this mixture are transferred to PCR reaction vessels, although there may be variations in loading volumes resulting from pipetting, variation is controlled in the NT/CT ratio for any gene relative to the NT/CT ratio for a reference gene. This approach also enables standardized expression measurement.

PCR Amplification

Each reaction mixture can be cycled either in an air thermocycler (e.g., Rapidcycler (Idaho Technology, Inc., Idaho Falls, Id.) or block thermocycler (e.g., PTC-100 block thermal cycler with heated lid, MJ Research, Inc., Incline Village, Nev.) for 35 cycles. In either thermocycler, the denaturation temperature is 94° C., the annealing temperature is 58° C., and the elongation temperature is 72° C.

Separation and Quantification of NT and CT PCR Products a. Agarose gel. Following amplification, the entire volume of PCR product (typically 10 μL) can be into wells of 4% agarose gels (3/1 NuSieve: Sea Kem) containing 0.5 μg/mL ethidium bromide. Gels can be electrophoresed for approx 1 h at 225 V in continuously chilled buffer, and then visualized and quantifying with an image analyzer (products available from Fotodyne, BioRad). Following electrophoresis, the relative amount of NT and CT can be determined by densitometric quantification of bands that have been stained by an intercalating dye (e.g., ethidium bromide).

b. PE Prism 310 Genetic Analyzer CE Device. PCR products can be amplified with fluor-labeled primers. One microliter of each PCR reaction can be combined with 9 µL of formamide and 0.5-0.1 µL of ROX size marker. Samples can be heated to 94° C. for 5 min and flash cooled in an ice slurry. Samples can be loaded onto the machine and electrophoresed at 15 kV, 60° C. for 35-45 min using POP4 polymer and filter set D. The injection parameters can be 15 kV, 5 sec. Fragment analysis software, GeneScan (Applied Biosystems, Inc., Foster City, Calif.) can be used to quantify peak heights that are used to calculate NT/CT ratios. No size correction need be performed where each DNA molecule was tagged with one fluorescent marker from one labeled primer.

c. Agilent 2100 Bioanalyzer Microfluidic CE Device. The DNA 7500 or DNA 1000 LabChip kit may be used. Following amplification, 1 µL of each 10 µL PCR reaction can be loaded into a well of a chip prepared according to protocol supplied by manufacturer. DNA assay can be run, which applies a current to each sample sequentially to separate NT from CT. DNA can be detected by fluorescence of an intercalating dye in the gel-dye matrix. NT/CT ratios can be calculated from area under curve (AUC) and one or more size corrections can be made.

d. Caliper AMS 90 Microfluidic CE Device. The PCR reactions can be set up in wells of a 96- or 384-well microplate. Following amplification, the microplate can be placed in a Caliper AMS 90 and protocol recommended by the manufacturer followed. The AMS 90 can remove and electrophorese a sample from each well sequentially every 30 sec. The NT and CT PCR products can be separated and quantified. Where detection is through fluorescent intercalating dye, size correction need not be necessary.

e. MALDI-TOF separation. A method for separating PCR products recently was described. Ding, C. and Cantor, C. R. (2003) A high-throughput gene expression analysis technique using competitive PCR and matrix-assisted laser desorption ionization time-of-flight MS. *Proc. Natl. Acad. Sci. USA* 100, 3059-3064. This method may be used to quantify products resulting from amplification of cDNA in the presence of SMIS.

Figure 24:
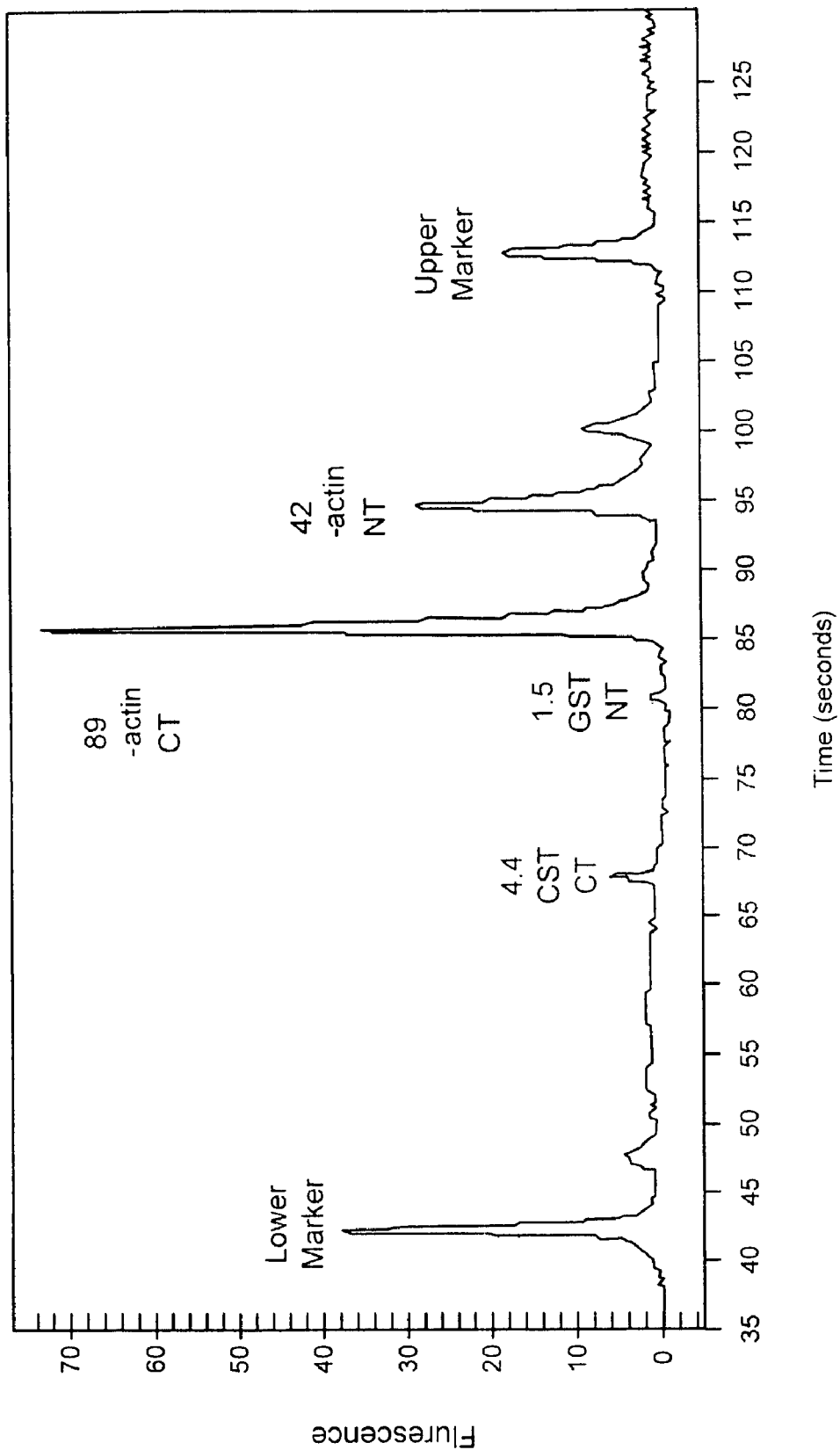
FIG. 24 illustrates a calculation of gene expression based on densitometric values for electrophoretically separated amplified product of GST NT and CT.

Calculation of Gene Expression—Calculating the Number of NT Molecules Present at the Beginning of PCR for Each Gene The steps taken to calculate gene expression can be based on densitometric measurement values for electrophoretically separated NT and CT PCR products such as those presented in FIG. 24. The calculations below are based on the example in FIG. 24, measuring GST gene expression relative to β-actin in an actual bronchial epithelial cell (BEC) sample. A volume of SMIS containing 600,000 competitive template molecules for α-actin and 6000 competitive template molecules for GST was included at the beginning of the PCR reaction. For each gene, the NT and competitive template amplify with the same efficiency. Thus, the β-actin gene NT/CT PCR product ratio allows determination of the number of β-actin NT copies at the beginning of PCR and the target gene NT/CT ratio allows determination of the number of target gene copies of the beginning of PCR, as detailed in the steps below:

1. Correct NT PCR product area under the peak (AUP) to length of CT DNA.
2. Determine ratio of corrected NT AUP relative to CT AUP.
3. Multiply NT/CT value×number of CT molecules at beginning of PCR.

A calculation of β-actin molecules using above protocol is outlined below:

1. 416/532 (β-actin CT bp/NT bp)×42 (NT AUP)=33 (corrected NT value).
2. Correct β-actin NT AUP divided by β-actin CT AUP=0.37.
3. 0.37 (β-actin NT/CT)×600,000 (number of (β-actin CT molecules at beginning of PCR)=222,000 NT molecules at beginning of PCR.

A calculation of GST molecules using above protocol is outlined below:

1. 227/359 (GST CT bp/NT bp)×1.5 (NT AUP)=0.95 (corrected NT AUP).
2. 0.95 (GST corrected NT AUP) divided by 4.4 (GST CT AUP)=0.22.
3. 0.22 (GST NT/CT)×6000 (number of GST CT molecules at beginning of PCR)=1290 GST NT molecules at beginning of PCR.

Calculation of molecules of GST/$10^6$ β-actin molecules is 1290 GST NT molecules/222,000 β-actin NT molecules=580 GST molecules/$10^6$ β-actin molecules.

Example IV

Blinded Inter-Laboratory Study to Evaluate Reproducibility

In a first study, six laboratories participated in triplicate measurement of five genes in cDNA derived from a bronchogenic carcinoma tissue sample 16009T. A variety of electrophoresis methods and imaging software programs were used in different laboratories to analyze amplified product. Study 1 Laboratory 2 used an Agilent 2100 Bioanalyzer. The intra-laboratory average CV for all gene expression measurements was 0.36, which is comparable to that previously reported (Willey et al, 1998; Rots et al, 1999; Rots et al; 2000; Mollerup et al, 1999; Loitsch et al, 1999). The inter-laboratory variation showed an average CV of 0.71.

In a second study, slab gel electrophoresis and NIH Image software was used to measure expression of 10 genes (the 5 previously measured plus 5 additional genes) in A549 cDNA. Four of the original laboratories were able to participate in the second study. The combined average CV for all nine genes that could be measured was 0.27 and 0.48 for intra-lab and inter-lab comparison, respectively. For TNF alpha, each laboratory determined that the expression was too low to be quantified. Of the four laboratories, three laboratories were able to quantify HNF3α while the fourth lab was not. The lower limit of detection of a PCR product above background was established for the second study as an NIH image arbitrary densitometric value of 5 above background. Although the fourth laboratory observed NT and CT PCR products for HNF3 α, they were below the cut-off level of 5 and therefore not included in the analysis. A CT mix that contributed 60 molecules of nucleic acid CT (F mix) was used to detect HNF3α.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limitative sense, the scope of the invention being defined solely by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and compositions within the scope of these claims and their equivalents be covered thereby.

All publications, patents, and patent applications mentioned in this specification are herein incorporated by reference to the same extent as if each individual publication, patent or patent application was specifically and individually indicated as being incorporated by reference.

What is claimed is:

1. A method of assessing allele frequency of a first allele and a second allele of a target nucleic acid in a sample, comprising:
   co-amplifying said target nucleic acid and a known amount of a competitive template for said target nucleic acid;
   co-amplifying a reference nucleic acid and a known amount of a competitive template for said reference nucleic acid;
   obtaining a first relation, said first relation comparing amplified product of said target nucleic acid corresponding to said first allele to amplified product of said competitive template for said target nucleic acid;
   obtaining a second relation, said second relation comparing amplified product of said target nucleic acid corresponding to said second allele to amplified product of said competitive template for said target nucleic acid;
   obtaining a third relation, said third relation comparing amplified product of said reference nucleic acid to amplified product of said competitive template for said reference nucleic acid;
   comparing one of said first, second or third relations to both of said other relations, thereby assessing allele frequency of said first and said second alleles in said sample; and
   detecting false positives of said first allele by the steps of: co-amplifying a known amount of positive control for said second allele and a known amount of said competitive template for said target nucleic acid; and obtaining a fourth relation, said fourth relation comparing amplified product of said positive control for said second allele that is detectable by a detection moiety specific for said first allele to amplified product of said competitive template for said target nucleic acid,
   wherein obtaining said first, second and/or third relation comprises a use of an oligonucleotide array and wherein said amplified products of said target nucleic acid corresponding to said first allele, of said target nucleic acid corresponding to said second allele and of said competitive template for said target nucleic acid are immobilized by a first common capture moiety.

2. A method of assessing allele frequency of a first allele and a second allele of a target nucleic acid in a sample, comprising:
   co-amplifying said target nucleic acid and a known amount of a competitive template fir said target nucleic acid;
   co-amplifying a reference nucleic acid and a known amount of a competitive template for said reference nucleic acid;
   obtaining a first relation, said first relation comparing amplified product of said target nucleic acid corresponding to said first allele to amplified product of said competitive template for said target nucleic acid;
   obtaining a second relation, said second relation comparing amplified product of said target nucleic acid corresponding to said second allele to amplified product of said competitive template for said target nucleic acid;
   obtaining a third relation, said third relation comparing amplified product of said reference nucleic acid to amplified product of said competitive template for said reference nucleic acid;

comparing one of said first, second or third relations to both of said other relations, thereby assessing allele frequency of said first and said second alleles in said sample; and detecting false positives of said first allele by the steps of: co-amplifying a known amount of positive control for said second allele and a known amount of said competitive template for said target nucleic acid; and obtaining a fourth relation, said fourth relation comparing amplified product of said positive control for said second allele that is detectable by a detection moiety specific for said first allele to amplified product of said competitive template for said target nucleic acid, wherein obtaining said first, second and/or third relation comprises a use of an oligonucleotide array and wherein said amplified products of said reference nucleic acid and of said competitive template for said reference nucleic acid are immobilized by a second common capture moiety.

3. The method as recited in claim 1 or 2, wherein said target nucleic acid comprises genomic DNA.

4. The method as recited in claim 1 or 2, wherein said target nucleic acid comprises mRNA.

5. The method as recited in claim 1 or 2, wherein said target nucleic acid comprises cDNA.

6. The method as recited in claim 1 or 2, wherein said sample comprises pooled nucleic acid from different subjects.

7. The method as recited in claim 1 or 2, wherein said sample comprises nucleic acid from a disease state.

8. The method as recited in claim 1 or 2, wherein said first and said second alleles comprise single nucleotide polymorphisms.

9. The method as recited in claim 1 or 2, wherein said method does not involve real time measurements.

10. The method as recited in claim 1 or 2, wherein said method does not involve generation of a standard curve.

11. The method as recited in claim 1 or 2, wherein said method does not use two-color labeling.

12. The method as recited in claim 1 or 2, wherein said method does not use allele-specific primers.

13. The method as recited in claim 1 or 2, wherein said method does not use a universal priming sequence.

14. The method as recited in claim 1 or 2, wherein method does not detect aneuploidy.

15. The method as recited in claim 1 or 2, wherein said method does not use pyrophosphorolysis.

16. The method as recited in claim 1 or 2, wherein said method does not use gel electrophoresis.

17. The method as recited in claim 1 or 2, wherein obtaining said first, second and/or third relation comprises immobilization of said amplified products.

18. The method as recited in claim 17, wherein at least two of said immobilized amplified products are distinguished using at least two detection moieties selected from a detection moiety specific for said first allele, a detection moiety specific for said second allele, and a detection moiety specific for said competitive template for said target nucleic acid.

19. The method as recited in claim 18, wherein said immobilized amplified products are distinguished using a detection moiety specific for said reference nucleic acid and a detection moiety specific for said competitive template for said reference nucleic acid.

20. The method as recited in claim 1 or 2, further comprising detecting false negatives for said first allele by the steps of: co-amplifying a known amount of a positive control for said first allele and a known amount of said competitive template for said target nucleic acid; and obtaining a fifth relation, said fifth relation comparing amplified product of said positive control for said first allele that is detectable by a detection moiety specific for said first allele to amplified product of said competitive template for said target nucleic acid.

21. The method as recited in claim 20, wherein said positive control for said first allele is co-amplified with a substantially equal amount of said competitive template for said target nucleic acid.

22. The method as recited in claim 20, wherein said false negatives are reduced.

23. The method as recited in claim 20, wherein said false negatives are eliminated.

24. The method as recited in claim 1 or 2, wherein said positive control for said second allele is co-amplified with a substantially equal amount of said competitive template for said target nucleic acid.

25. The method as recited in claim 1 or 2, wherein said false positives are reduced.

26. The method as recited in claim 1 or 2, further comprising detecting false negatives of said second allele by the steps of: co-amplifying a known amount of a positive control for said second allele and a known amount of said competitive template for said target nucleic acid; and obtaining a sixth relation, said sixth relation comparing amplified product of said positive control for said second allele that is detectable by a detection moiety specific for said second allele to amplified product of said competitive template for said target nucleic acid.

27. The method as recited in claim 26, wherein said positive control for said second allele is co-amplified with a substantially equal amount of said competitive template for said target nucleic acid.

28. The method as recited in claim 26, wherein said false negatives are reduced.

29. The method as recited in claim 26, wherein said false negatives are eliminated.

30. The method as recited in claim 1 or 2, further comprising detecting false positives of said second allele by the steps of: co-amplifying a known amount of positive control for said first allele and a known amount of said competitive template for said target nucleic acid; and obtaining a seventh relation, said seventh relation comparing amplified product of said positive control for said first allele that is detectable by a detection moiety specific for said second allele to amplified product of said competitive template for said target nucleic acid.

31. The method as recited in claim 30, wherein said positive control for said first allele is co-amplified with a substantially equal amount of said competitive template for said target nucleic acid.

32. The method as recited in claim 30, wherein said false positives are reduced.

33. The method as recited in claim 1 or 2, wherein said first and said second relation are substantially constant beyond an exponential phase of said amplification of said target nucleic acid.

34. The method as recited in claim 1 or 2, wherein the co-amplifying of said target nucleic acid and said competitive template for said target nucleic acid employs some primers, the method further comprising, the method further comprising: diluting said co-amplified products of said target nucleic acid and of said competitive template for said target nucleic acid; and further co-amplifying said diluted amplified products using the same primers as used in the initial co-amplifying step.

35. The method as recited in claim 1 or 2, wherein less than about 100 molecules of said target nucleic acid in said sample are amplified.

36. The method as recited in claim 1 or 2, wherein said competitive templates are provided in a standardized mixture at known concentrations relative to each other.

37. The method as recited in claim 1 or 2, wherein said competitive template for said target nucleic acid is provided at a series of dilutions relative to said competitive template for said reference nucleic acid.

38. The method as recited in claim 1 or 2, wherein said method is computer implemented.

39. The method as recited in claim 2, wherein said immobilized amplified products are distinguished using a detection moiety specific for said reference nucleic acid and a detection moiety specific for said competitive template for said reference nucleic acid.

* * * * *

UNITED STATES PATENT AND TRADEMARK OFFICE
CERTIFICATE OF CORRECTION

PATENT NO. : 8,304,192 B2  
APPLICATION NO. : 11/072700  
DATED : November 6, 2012  
INVENTOR(S) : James C. Willey, Erin L. Crawford and David A. Weaver Page 1 of 1

It is certified that error appears in the above-identified patent and that said Letters Patent is hereby corrected as shown below:

Column 88, Claim 34, line 62, please remove the first occurrence of "the method further comprising,".

Signed and Sealed this
Eighteenth Day of December, 2012

David J. Kappos
*Director of the United States Patent and Trademark Office*

SEQUENCE LISTING

```
<160> NUMBER OF SEQ ID NOS: 34

<210> SEQ ID NO 1
<211> LENGTH: 20
<212> TYPE: DNA
<213> ORGANISM: Homo sapiens

<400> SEQUENCE: 1
atcctcaccc tgaagtaccc                                                   20

<210> SEQ ID NO 2
<211> LENGTH: 20
<212> TYPE: DNA
<213> ORGANISM: Homo sapiens

<400> SEQUENCE: 2
ccatctcttg ctcgaagtcc                                                   20

<210> SEQ ID NO 3
<211> LENGTH: 40
<212> TYPE: DNA
<213> ORGANISM: Homo sapiens

<400> SEQUENCE: 3
ccatctcttg ctcgaagtcc gccagccagg tccagacgca                             40

<210> SEQ ID NO 4
<211> LENGTH: 70
<212> TYPE: DNA
<213> ORGANISM: Homo sapiens

<400> SEQUENCE: 4
catcgtgatg gactccggtg acggggtcac ccacactgtg cccatctacg aggggtatgc       60
cctcccccat                                                              70

<210> SEQ ID NO 5
<211> LENGTH: 19
<212> TYPE: DNA
<213> ORGANISM: Homo sapiens

<400> SEQUENCE: 5
gcgggaaatc gtgcgtgac                                                    19

<210> SEQ ID NO 6
<211> LENGTH: 18
<212> TYPE: DNA
<213> ORGANISM: Homo sapiens

<400> SEQUENCE: 6
cctggctggc ggacttcg                                                     18

<210> SEQ ID NO 7
<211> LENGTH: 20
<212> TYPE: DNA
```

<213> ORGANISM: Homo sapiens

<400> SEQUENCE: 7
ccagaagaaa gcggtcaaga                                          20

<210> SEQ ID NO 8
<211> LENGTH: 20
<212> TYPE: DNA
<213> ORGANISM: Homo sapiens

<400> SEQUENCE: 8
aaccttcatt ttcccctggg                                          20

<210> SEQ ID NO 9
<211> LENGTH: 40
<212> TYPE: DNA
<213> ORGANISM: Homo sapiens

<400> SEQUENCE: 9
aaccttcatt ttcccctggg ccagtgatga gcgggttaca                    40

<210> SEQ ID NO 10
<211> LENGTH: 70
<212> TYPE: DNA
<213> ORGANISM: Homo sapiens

<400> SEQUENCE: 10
agtccggatc tcacttggcg gcaagggaga aggcaaatct gtgaggccgg ggccctgcac    60
ctgtgcagcg                                                     70

<210> SEQ ID NO 11
<211> LENGTH: 70
<212> TYPE: DNA
<213> ORGANISM: Homo sapiens

<400> SEQUENCE: 11
cgctgcacag gtgcagggcc ccggcctcac agatttgcct tctcccttgc cgccaagtga    60
gatccggact                                                     70

<210> SEQ ID NO 12
<211> LENGTH: 23
<212> TYPE: DNA
<213> ORGANISM: Homo sapiens

<400> SEQUENCE: 12
cctgtgctag atgtgcaaat gca                                      23

<210> SEQ ID NO 13
<211> LENGTH: 19
<212> TYPE: DNA
<213> ORGANISM: Homo sapiens

<400> SEQUENCE: 13
catcactggc ccaggggaa                                           19

<210> SEQ ID NO 14
<211> LENGTH: 19
<212> TYPE: DNA
<213> ORGANISM: Homo sapiens

<400> SEQUENCE: 14
ttcccctggg ccagtgatg                                           19

```
<210> SEQ ID NO 15
<211> LENGTH: 26
<212> TYPE: DNA
<213> ORGANISM: Homo sapiens

<400> SEQUENCE: 15
gcattaaaat tgttacacaa tctgct                                          26

<210> SEQ ID NO 16
<211> LENGTH: 26
<212> TYPE: DNA
<213> ORGANISM: Homo sapiens

<400> SEQUENCE: 16
cgtaatttta acaatgtgtt agacga                                          26

<210> SEQ ID NO 17
<211> LENGTH: 26
<212> TYPE: DNA
<213> ORGANISM: Homo sapiens

<400> SEQUENCE: 17
gcattaaaat tggtacacaa tctgct                                          26

<210> SEQ ID NO 18
<211> LENGTH: 26
<212> TYPE: DNA
<213> ORGANISM: Homo sapiens

<400> SEQUENCE: 18
cgtaatttta accatgtgtt agacga                                          26

<210> SEQ ID NO 19
<211> LENGTH: 48
<212> TYPE: DNA
<213> ORGANISM: Homo sapiens

<400> SEQUENCE: 19
aaccttcatt ttcccctggg gaaatagcat taaaattggt acacaatc                  48

<210> SEQ ID NO 20
<211> LENGTH: 20
<212> TYPE: DNA
<213> ORGANISM: Homo sapiens

<400> SEQUENCE: 20
cgcaacggca agagttacac                                                 20

<210> SEQ ID NO 21
<211> LENGTH: 20
<212> TYPE: DNA
<213> ORGANISM: Homo sapiens

<400> SEQUENCE: 21
agactgttga ctggcgtgat                                                 20

<210> SEQ ID NO 22
<211> LENGTH: 40
<212> TYPE: DNA
<213> ORGANISM: Homo sapiens

<400> SEQUENCE: 22
agactgttga ctggcgtgat cccggagctt ttcaccttta                           40
```

```
<210> SEQ ID NO 23
<211> LENGTH: 21
<212> TYPE: DNA
<213> ORGANISM: Homo sapiens

<400> SEQUENCE: 23
ggtcggagtc aacggatttg g                                              21

<210> SEQ ID NO 24
<211> LENGTH: 21
<212> TYPE: DNA
<213> ORGANISM: Homo sapiens

<400> SEQUENCE: 24
cctccgacgc ctgcttcacc a                                              21

<210> SEQ ID NO 25
<211> LENGTH: 42
<212> TYPE: DNA
<213> ORGANISM: Homo sapiens

<400> SEQUENCE: 25
cctccgacgc ctgcttcacc agaggggcca tccacagtct tc                       42

<210> SEQ ID NO 26
<211> LENGTH: 20
<212> TYPE: DNA
<213> ORGANISM: Homo sapiens

<400> SEQUENCE: 26
agggcatcct gggctacact                                                20

<210> SEQ ID NO 27
<211> LENGTH: 20
<212> TYPE: DNA
<213> ORGANISM: Homo sapiens

<400> SEQUENCE: 27
ggttgagcac agggtacttt                                                20

<210> SEQ ID NO 28
<211> LENGTH: 40
<212> TYPE: DNA
<213> ORGANISM: Homo sapiens

<400> SEQUENCE: 28
ggttgagcac agggtacttt gattcagtgt ggtgggggac                          40

<210> SEQ ID NO 29
<211> LENGTH: 20
<212> TYPE: DNA
<213> ORGANISM: Homo sapiens

<400> SEQUENCE: 29
tacgcagcgc ctccctccac                                                20

<210> SEQ ID NO 30
<211> LENGTH: 20
<212> TYPE: DNA
<213> ORGANISM: Homo sapiens

<400> SEQUENCE: 30
ctgttctcgt cgtttccgca                                                20
```

```
<210> SEQ ID NO 31
<211> LENGTH: 40
<212> TYPE: DNA
<213> ORGANISM: Homo sapiens

<400> SEQUENCE: 31
ctgttctcgt cgtttccgca accttgggg ccttttcatt                              40

<210> SEQ ID NO 32
<211> LENGTH: 24
<212> TYPE: DNA
<213> ORGANISM: Homo sapiens

<400> SEQUENCE: 32
ccatcgtgta atcaaggact tcat                                              24

<210> SEQ ID NO 33
<211> LENGTH: 22
<212> TYPE: DNA
<213> ORGANISM: Homo sapiens

<400> SEQUENCE: 33
ttgccatcca gccaggaggt ct                                                22

<210> SEQ ID NO 34
<211> LENGTH: 42
<212> TYPE: DNA
<213> ORGANISM: Homo sapiens

<400> SEQUENCE: 34
ttgccatcca gccaggaggt ctgacccagc caggcccgta gt                          42
```